US008765783B2

(12) United States Patent
Nakade et al.

(10) Patent No.: US 8,765,783 B2
(45) Date of Patent: Jul. 1, 2014

(54) PHARMACEUTICAL COMPOSITION FOR TREATMENT OF DISEASE DUE TO VASCULAR CONSTRICTION OR VASODILATION

(75) Inventors: Shinji Nakade, Tsukuba (JP); Hidehiro Suzuki, Tsukuba (JP); Hiromu Habashita, Mishima-gun (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 1624 days.

(21) Appl. No.: 10/519,113

(22) PCT Filed: Jun. 25, 2003

(86) PCT No.: PCT/JP03/08039
§ 371 (c)(1),
(2), (4) Date: Nov. 1, 2005

(87) PCT Pub. No.: WO2004/002531
PCT Pub. Date: Jan. 8, 2004

(65) Prior Publication Data
US 2006/0148844 A1 Jul. 6, 2006

(30) Foreign Application Priority Data
Jun. 26, 2002 (JP) .............................. P. 2002-185546

(51) Int. Cl.
*A61K 31/44* (2006.01)
(52) U.S. Cl.
USPC ......................................................... 514/303
(58) Field of Classification Search
None
See application file for complete search history.

(56) References Cited

U.S. PATENT DOCUMENTS

| 3,542,793 | A | 11/1970 | Alberto Rossi et al. |
| 4,612,318 | A | 9/1986 | Winters |
| 5,985,873 | A | 11/1999 | Blum et al. |
| 6,903,089 | B1 | 6/2005 | Stasch et al. |
| 7,115,750 | B1 | 10/2006 | Kato et al. |
| 2004/0067937 | A1 | 4/2004 | Stasch et al. |
| 2004/0082596 | A1 | 4/2004 | Stasch et al. |

FOREIGN PATENT DOCUMENTS

| DE | 2801187 A1 | 7/1978 | |
| DE | 100 57 751 A1 | 5/2002 | |
| DE | 100 57 754 A1 | 5/2002 | |
| DE | 101 22 895 A1 | 5/2002 | |
| EP | 0 107 619 A1 | 5/1984 | |
| JP | 8-253484 A | 10/1996 | |
| JP | 2002-003370 A | 1/2002 | |
| WO | 99-07672 A1 | 2/1999 | |
| WO | 9931267 A1 | 6/1999 | |
| WO | WO 01/03739 A1 | 1/2001 | |
| WO | 01/23389 A2 | 4/2001 | |
| WO | WO 01/69252 | * 9/2001 | ............. G01N 33/53 |
| WO | WO 01/69252 A1 | 9/2001 | |
| WO | 01/83490 A1 | 11/2001 | |
| WO | 01-97786 A2 | 12/2001 | |
| WO | WO 01/98301 A1 | 12/2001 | |
| WO | 02-05819 A1 | 1/2002 | |
| WO | WO 02/05819 | * 1/2002 | ............ A61K 31/495 |
| WO | WO 02/06229 | * 1/2002 | ............ C07D 211/00 |
| WO | 02/42301 A1 | 5/2002 | |
| WO | 03051274 A2 | 6/2003 | |
| WO | WO 03/045313 | * 6/2003 | ......... C07D 215/227 |
| WO | WO 03/049741 | * 6/2003 | ............ A61K 31/428 |
| WO | WO 03/051876 A1 | 6/2003 | |

OTHER PUBLICATIONS

STN Search Report (Accession No. 2002:72044) Jan. 2002.*
STN Search Report (Accession No. 1978:130817) containing Agrawal et al (Indian Journal of Pharmacy 39(6):139-140, 1977).*
STN Search Report (Accession No. 1978:74324) (summarizing Arya et al (Indian J Chemistry, Section B: Organic Chemistry Including Medicinal Chemistry 15B(7):635-640, 1977)).*
STN Search Report (Accession No. 2003:472390).*
STN Search Report (Accession No. 2003: 434303).*
STN Search Report (Accession No. 2002:71877).*
CAS RN 125525-94-2 (entered into STN Feb. 23, 1990).*
CAS RN 401642-16-8 (entered into STN Apr. 18, 2002).*
Anderson (Chem and Biol 10:787-797, 2003).*
Thiel (Nature Biotechnol 2:513-519, 2004).*
Kim et al (Bioorg Med Chem 16:3.937-3942, 2006).*
Tsukasa Ohmori et al. "Sphingosine 1-phosphate induces contraction of coronary artery smooth muscle cells via $SIP_2$", Cardiovascular Research (2003) vol. 58, No. 1, pp. 170-177.
Hiroshi Okazaki et al., "Molecular Cloning of a Novel Putative G. Protein-Coupled Receptor Expressed in the Cardiovascular System", Biochem., Biophys. Res. Comm. (1993) vol. 190, No. 3, pp. 1104-1109.
International Search Report dated Oct. 14, 2003.
Okazaki, H., 'Molecular cloning of a novel putative G protein-coupledreceptor expressed in the cardiovascular system. ', Biochem . Biophys. Res. Commun ., Feb. 15, 1993, vol. 190, No. 3, p. 1104-1109.

(Continued)

Primary Examiner — Craig Ricci
(74) Attorney, Agent, or Firm — Sughrue Mion, PLLC

(57) ABSTRACT

A therapeutic and/or preventing agent for a disease due to vascular constriction or vasodilation comprising a EDG-5 modulator. Since EDG-5 modulator specifically binds EDG-5 and shows antagonistic or agonistic action, EDG-5 antagonist is useful for treating and/or preventing for a disease due to vascular constriction, for example, cerebrovascular spasmodic disorder after subarachnoid hemorrhage or stroke, cardiovasucular spasmodic disorder, hypertension, renal disease, cardiac infarction, cardiac angina, arrhythmia, facilitation of the portal blood pressure involved in liver cirrhosis, varicosity involved in liver cirrhosis and the like, or EDG-5 agonist is useful for treating and/or preventing for a disease due to vasodilation of blood vessels, for example, chronic headache (such as migraine, tension-type headache, mixed-type headache thereof, or migrainous neuralgia), haemorrhoid, congestive disorder and the like.

7 Claims, 7 Drawing Sheets

(56) References Cited

OTHER PUBLICATIONS

Ohmori, T., 'Sphingosin 1-phosphate induces contraction of coronary artery smooth muscle cells via SIP$_2$, Cardiovasc . Res ., Apr. 1, 2003 , vol. 58, No. 1, p. 170-177.
Japanese Office Action for Application No. P2004-517272, dated Jul. 3, 2009.
Japanese Office Action for Application No. P2004-517272, dated Oct. 8, 2009.
Supplementary European Search Report dated Aug. 14, 2009 in EP Application No. 03761797.4.
European Office Action for Application No. 03761797.4 dated Jul. 14, 2010.
Japanese Office Action, dated Oct. 29, 2010, issued in Application No. 2004-517272.
B. Pandey, "Central Nervous System Depressant, Analgesic and Monoamine Oxidase Inhibitory Properties of Substituted Piperidines", Research Communications in Chemical Pathology and Pharmacology, 1984, Vo. 43, No. 1, pp. 173-176.
C. Wermuth, "Saishin Soyaku Kagaku" (New Drug-Creating Chemistry), vol. 1, K.K. Technomic, Aug. 15, 1998, pp. 235-271, p. 241.
Communication dated Dec. 6, 2011, issued by the European Patent Office in corresponding European Application No. 03761797.4.
Extended European Search Report, dated Nov. 12, 2012, issued by the European Patent Office in counterpart European Application No. 12005031.5.

\* cited by examiner

PHARMACEUTICAL COMPOSITION FOR TREATMENT OF DISEASE DUE TO VASCULAR CONSTRICTION OR VASODILATION

FIELD OF THE INVENTION

The present invention relates to a pharmaceutical composition for treatment and/or prevention of a disease due to constriction or vasodilation of blood vessels comprising EDG (Endothelial differentiation gene)-5 modulator which is useful as a drug, and relates to novel EDG-5 antagonists.

BACKGROUND ART

It has been supposed that Sphingosine-1-phosphate ((2S, 3R,4E)-2-amino-3-hydroxyoctadeca-4-enyl-1-phosphate; S1P) is a lipid which is synthesized by turnover of intracellular sphingolipid and activities of extracellular secretable sphingosine kinase, acts as an intercellular or intracellular messenger. First, an experimental result which suggests S1P acts as an intracellular second messenger was reported [Science, 248, 1653(1990)]. However, it has not yet been found that S1P directly acts to intracellular molecules.

In addition, it has been suggested that S1P acts through cell-surface receptors than extracellular ones, and it has been noted that it plays a role as an intercellular messenger. Recently, cloning of S1P receptor has been made progress and it has been reported that G-protein coupled receptor, EDG-1 ($S1P_1$), EDG-3 ($S1P_3$), EDG-5 (AGR16/H218/$S1P_2$), EDG-6 ($S1P_4$) and EDG-8 ($S1P_5$) are as specific S1P receptors.

It has been disclosed that these S1P receptors also have high homology to lysophosphatidic acid (LPA) receptor, EDG-2, 4, 7. Now, it has been considered that EDG-1-8 form S1P/LPA receptor family.

As the in vitro biological effects of S1P, cell motility inhibition of smooth muscle cells and cancer cells, platelets aggregation and the like are known. As the in vivo biological effects of S1P, vasucularization, decrease of renal blood flow, inhibition of pulmonary fibrosis and the like are known. And, it has been reported that S1P constricts canine basilar artery and renal artery [Stroke, 32, 2913(2001); British J. Pharmacol., 130, 1871(2000)].However, it has not been revealed which receptor subtypes caused such actions of S1P.

In addition, as for EDG-5, it has been reported that the mRNA expression is strongly recognized in heart, lung, stomach, and small intestine tissue. And, in arterial sclerosis model of coronary artery, mice carotid balloon injury model, it has been reported that the mRNA expression level in intima of a vessel cells significantly decrease more than in healthy ones. In EDG-5 knock-out mice, an effect on nerve system [Eur. J. Neurosci. 14, 203 (2001)], body length shortening [J. Biol. Chem. 2002] and the like have been reported.

On the other hand, WO01/03739 discloses that S1P receptor agonist or S1P inhibit various organs fibrosis. And, WO01/98301 discloses that pyrazolopyridine compounds which have an antagonistic effect to S1P receptors and those are useful in treatment for hepatic fibrosis, pulmonary fibrosis, renal fibrosis and arterial sclerosis. There is no description or suggestion about an effect on constriction of blood vessels in these both.

Besides, JP2001-261575 vaguely discloses that a therapeutic method for a improvable disease by constriction of blood vessels due to EDG-5 receptor signaling modulation or inhibition of constriction of blood vessels. However, in this specification, as EDG receptor agonist and antagonist, there is description about only EDG-3 receptor agonist and antagonist. There is no description or suggestion about function of other Edg receptor subtypes and Edg receptor subtype selective agonist or antagonist. And, as a constriction of blood vessels, there is description about constriction of arterial blood vessels, in particular cerebral artery. There is no description or suggestion about constriction of vein.

And, 4-(4-chlorophenyl)-N-(3-(2-diisopropylamino) ethoxy)-4-methoxyphenyl)-4-hydroxy-1-piperidinecarboxamide (CAS No. 391881-92-8), N-(3-chlorophenyl)-4-(4-chlorophenyl)-4-hydroxy-1-piperidinecarboxamide(CAS No. 401642-16-8), 4-(4-chlorophenyl)-N-(3,4-dichlorophenyl)-4-hydroxy-1-piperidinecarboxamide (CAS No. 401642-17-9), methyl 2-(benzyloxy)-5-(((4-(4-chlorophenyl)-4-(hydroxyl-1-pyperidinyl)carbonyl)amino)benzoate (CAS No. 508216-25-9), 4-(4-bromophenyl)-N-(4-chlorophenyl)-4-hydroxy-1-piperidinecarboxamide (Microsource. Co. Ltd. Cat. No. 9132838), 4-(4-bromophenyl)-4-hydroxyl-N-(3-(trifuloromethyl)phenyl)-1-piperidinecarboxamide (Microsource. Co. Ltd. Cat. No. 9132846), 4-(4-bromophenyl) -4-hydroxy-N-phenyl-1-piperidinecarboxamide (Microsource. Co. Ltd. Cat. No. 9132844) are known.

DISCLOSURE OF THE INVENTION

The present inventors have keenly examined in order to elucidate the role of S1P receptors and found that constriction or vasodilation of cerebral artery (for example, basilar artery, middle cerebral artery, internal carotid artery and the like), renal artery, coronary artery, pulmonary artery and vein are caused by specifically EDG-5 out of S1P receptors. In addition, they have first found that S1P is involved in constriction or vasolidation of main artery, and that action is caused through specifically EDG-5 antagonist. And, they have also disclosed that EDG-5 acts on blood pressure. These were first ascertained by them this time, though not expected from the prior art in the least. Accordingly, due to EDG-5 modulation, we can module constriction or vasodilation action in cerebral artery (for example, basilar artery, middle cerebral artery, internal carotid artery and the like), renal artery, coronary artery, pulmonary artery and vein by S1P. It has been found that we can inevitably treat and/or prevent a disease induced by constriction or vasodilation of these arteries or veins.

In addition, the present inventors have found novel selective EDG-5 antagonists and have completed the present invention based on these findings.

Thus, the present invention relates to a therapeutic and/or preventing agent for a disease due to constriction or vasodilation of blood vessels comprising EDG-5 modulator. Particularly, the present invention relates to a therapeutic and/or preventing agent for a disease due to constriction of blood vessels comprising EDG-5 antagonist, and a therapeutic and/or preventing agent for a disease due to vasodilation of blood vessels comprising EDG-5 antagonist.

In addition, the present invention relates to novel EDG-5 antagonists. Novel EDG-5 antagonists are useful for a disease other than a disease due to constriction of blood vessels, such as pulmonary fibrosis, hepatic fibrosis, renal fibrosis, bronchial asthma, nephropathy, diabetes, or hyperlipemia and the like.

The present invention relates to
1. A pharmaceutical composition for treatment and/or prevention of a disease due to constriction or vasodilation of blood vessels, which comprises an EDG-5 modulator.
2. The pharmaceutical composition for treatment and/or prevent ion of a disease according to above mentioned 1, wherein the disease due to constriction or vasodilation of blood vessels is selected from cerebrovascular spasmodic disorder, cardiovasucular spasmodic disorder, hypertension, renal disease, cardiac infarction, cardiac angina, arrhythmia, facilitation of the portal blood pressure, varicosity, chronic headache, haemorrhoid and congestive disorder.

3. The pharmaceutical composition for treatment and/or prevention of a disease according to above mentioned 2, wherein the blood vessel is cerebral artery, renal artery, coronary artery, pulmonary artery, aorta and vein.

4. The pharmaceutical composition for treatment and/or prevention of a disease due to constriction of blood vessels according to above mentioned 1, wherein the EDG-5 modulator is an EDG-5 antagonist.

5. The pharmaceutical composition for treatment and/or prevention of a disease according to above mentioned 4, wherein the disease due to constriction of blood vessels is cerebrovascular spasmodic disorder, cardiovasucular spasmodic disorder, hypertension, renal disease, cardiac infarction, cardiac angina, arrhythmia, facilitation of the portal blood pressure, varicosity, chronic headache, haemorrhoid and congestive disorder.

6. The pharmaceutical composition for treatment and/or prevention of a disease due to constriction of blood vessels according to above mentioned 4, wherein the EDG-5 antagonist is a compound represented by formula (I):

A-X—Y—Z—B     (I)

wherein A represents cyclic group optionally with a substituent(s),
X represents a single bond or a spacer of principal chain atomicities which are 1-3,
Y represents a single bond or a spacer of principal chain atomicities which are 1-3,
Z represents a single bond or a spacer of principal chain atomicities which are 1-3, and
B represents cyclic group optionally with a substituent(s), or
a pharmaceutically acceptable salt thereof 7. The pharmaceutical composition for treatment and/or prevention of a disease due to constriction of blood vessels according to above mentioned 4, wherein the EDG-5 antagonist is a pyrazolopyridine compound represented by formula (II):

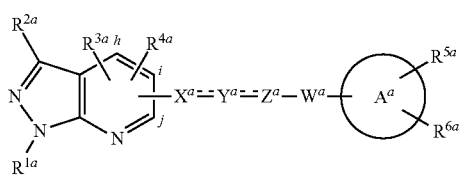

[wherein $R^{1a}$ represents hydrogen, C1-8 alkyl or —$COR^{7a}$ (wherein $R^{7a}$ represents C1-8 alkyl, optionally substituted aryl, optionally substituted aralkyl, C1-6 alkoxy, optionally substituted aryloxy or optionally substituted aralkyloxy);
$R^{2a}$ represents C1-8 alkyl or optionally substituted aryl;
$R^{3a}$ represents hydrogen, C1-8 alkyl, C1-6 alkoxy, C2-6 alkoxycarbonyl, haloalkyl, C3-7 cycloalkyl or optionally substituted aryl;
$R^{4a}$ represents hydrogen or C1-8 alkyl;

$R^{5a}$ and $R^{6a}$, each independently, represents hydrogen, C1-8 alkyl, C1-6 alkoxy, C2-6 alkoxycarbonyl, carboxyl, C2-6 alkynyl, halogen, cyano, nitro, haloalkyl, C1-8 alkylamino, di(C1-8 alkyl)amino, acyl, hydroxy, optionally substituted aryloxy, optionally substituted aralkyloxy, optionally substituted aryl, optionally substituted aralkyl, alkoxyalkyl or —$CONHR^{8a}$ (wherein $R^{8a}$ represents optionally substituted aryl or optionally substituted aralkyl);
$X^a$ represents —$N(R^{9a})$— (wherein $R^{9a}$ represents hydrogen, C1-8 alkyl or —$NHR^{10a}$ (wherein $R^{10a}$ represents carboxyl or C2-6 alkoxycarbonyl)), —O—, —N=, —CH= or —$CH(R^{11a})$— (wherein $R^{11a}$ represents hydrogen or C1-8 alkyl);
$Y^a$ represents —$N(R^{12a})$— (wherein $R^{12a}$ represents hydrogen, C1-8 alkyl, optionally substituted aralkyl, C2-6 alkoxycarbonyl, optionally substituted aryloxycarbonyl, optionally substituted aralkyloxycarbonyl or —$CONHR^{13a}$ (wherein $R^{13a}$ represents optionally substituted aryl or optionally substituted aralkyl)), =N—, —$CH_2$—, =CH—, —O—, —CO— or a single bond;
$Z^a$ represents —CO—, —CS—, —$CH_2$—, —O— or a single bond;
$W^a$ represents —$N(R^{14a})$— (wherein $R^{14a}$ represents hydrogen, C1-8 alkyl, optionally substituted aralkyloxycarbonyl, optionally substituted aryloxycarbonyl or heteroaryl-C1-8 alkyl), —O—, —CO—, —CONH— (wherein the nitrogen atom binds to ring$A^a$), —$CH_2$—, —$NHCH_2$— (wherein the carbon atom binds to ring$A^a$) or a single bond; and
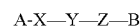 represents double bond or single bond;
Ring$A^a$ represents optionally substituted aryl, heteroaryl or C3-7 cycloalkyl.], or
a nontoxic salt thereof.

8. The pharmaceutical composition for treatment and/or prevention of a disease due to constriction of blood vessels according to above mentioned 1, wherein the EDG-5 modulator is an EDG-5 agonist.

9. The pharmaceutical composition for treatment and/or prevention of a disease according to above mentioned 8, wherein the disease due to vasodilation of blood vessels is chronic headache, haemorrhoid or congestive disorder.

10. A compound represented by formula (I):

A-X—Y—Z—B     (I)

(wherein all the symbols have the same meanings as those of above mentioned 6) or
a pharmaceutically acceptable salt thereof.

11. A compound represented by formula (I) described in above mentioned 10, or a pharmaceutically acceptable salt thereof, which excludes a compound represented by formula (II):

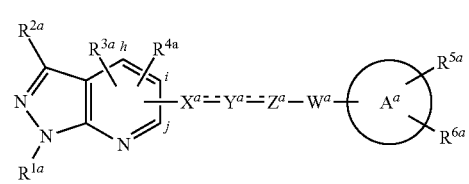

(wherein all the symbols have the same meanings as those of above mentioned 7), a nontoxic salt thereof, 4-(4- chlorophenyl)-N-(3-(2-(diisopropylamino)ethoxy)-4-methoxyphenyl)-4-hydroxy-1-piperidiniecarboxamide, N-(3-chlorophenyl)-4-(4-chlorophenyl)-4-hydroxy-1-piperidinecarboxamide, 4-(4-chlorophenyl)-N-(3,4-dichlorophenyl)-4-hydroxy-1-piperidinecarboxamide, methyl-2-(benzyloxy)-5-(((4-(4-chlorophenyl)-4-hydroxy-1-piperidinyl)carbonyl)amino)benzoate, 4-(4-bromophenyl)-N-(4-chlorophenyl)-4-hydroxy-1-piperidinecarboxamide, 4-(4-bromophenyl)-4-hydroxy-N-(3-trifluoromethyl)phenyl)-1-piperidinecarboxamide, and 4-(4-bromophenyl)-4-hydroxy-N-phenyl-1-piperidinecarboxamide.

12. The compound according to above mentioned 11, wherein X is a single bond.
13. The compound according to above mentioned 12, wherein Y is —CO— or —CS—.
14. The compound according to above mentioned 13, wherein Z is —NH—.
15. The compound according to above mentioned 14, wherein the cyclic group optionally with a substituent(s) represented by A is an optionally saturated or unsaturated 3-15 membered monocyclic aromatic heterocyclic ring containing 1-5 hetero atoms selected from an oxygen atom(s), a nitrogen atom(s), and/or a sulfur atom(s).
16. The compound according to above mentioned 14, wherein the cyclic group optionally with a substituent(s) represented by A is an optionally saturated or unsaturated 4-15 membered monocyclic aromatic heterocyclic ring containing 1-5 hetero atoms selected from an oxygen atom(s), a nitrogen atom(s), and/or a sulfur atom(s).
17. The compound according to above mentioned 15, wherein the cyclic group optionally with a substituent(s) represented by A is

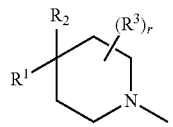

wherein $R^1$ represents a substituent,
$R^2$ represents hydrogen, hydroxy, or C1-6 alkoky,
$R^3$ represents a substituent, and
r represents 0 or an integer of 1-4.

18. The compound according to above mentioned 15, wherein the cyclic group optionally with a substituent(s) represented by A is

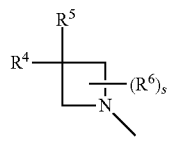

wherein $R^4$ represents a substituent,
$R^5$ represents hydrogen, hydroxy, or C1-6 alkoky,
$R^6$ represents a substituent, and
s represents 0 or an integer of 1-4.

19. The compound according to above mentioned 16, wherein the cyclic group optionally with a substituent(s) represented by A is

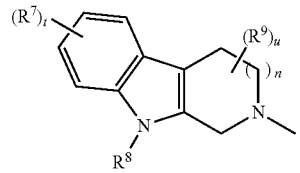

wherein $R^7$ represents a substituent,
$R^8$ represents hydrogen, or C1-6 alkyl,
$R^9$ represents a substituent,
t represents 0 or an integer of 1-4,
u represents 0 or an integer of 1-4, and
n represents 0 or an integer of 1-2.

20. The compound according to above mentioned 17, wherein $R^2$ is hydroxy.
21. The compound according to above mentioned 18, wherein $R^4$ is amino optionally with a substituent(s).
22. The compound according to above mentioned 20, wherein $R^1$ is a chain substituent.
23. The compound according to above mentioned 20, wherein $R^1$ is a cyclic substituent.
24. The compound according to above mentioned 22, wherein the chain substituent is alkyl.
25. The compound according to above mentioned 22, wherein the chain substituent is substituted alkyl.
26. The compound according to above mentioned 20, wherein $R^1$ is carbamoyl optionally with a substituent(s), carboxyl, alkoxycarbonyl, cyano, or acyl.
27. The compound according to above mentioned 24, wherein the cyclic group optionally with a substituent(s) represented by B is an aromatic ring.
28. The compound according to above mentioned 24, wherein the cyclic group optionally with a substituent(s) represented by B is a nonaromatic group.
29. The compound according to above mentioned 27, wherein the cyclic group is substituted with 1 or at least 2 substituent(s).
30. The compound according to above mentioned 29, wherein the cyclic group with at least 2 substituents is

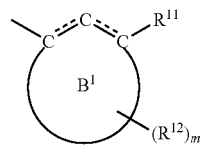

wherein $B^1$ represents a carbon ring of an aromatic ring,
$R^{11}$ and $R^{12}$ each represents a substituent,
m represents an integer of 1-4, and
the other symbols have the same meanings as those mentioned above.

31. The compound according to above mentioned 29, wherein the heterocyclic ring with at least 2 substituents is

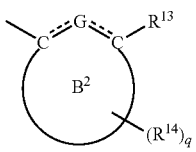

wherein $B^2$ represents a heterocyclic ring of an aromatic ring,
$R^{13}$ and $R^{14}$ each represents a substituent,
G represents carbon, nitrogen, oxygen, or sulfur,
q represents an integer of 1-4, and
the other symbols have the same meanings as those mentioned above.

32. The compound according to above mentioned 23, wherein the cyclic substituent is a saturated carbon ring.
33. The compound according to above mentioned 32, wherein the cyclic group optionally with a substituent(s) represented by B is an aromatic ring.
34. The compound according to above mentioned 32, wherein the cyclic group optionally with a substituent(s) represented by B is a nonaromatic ring.
35. The compound according to above mentioned 33, wherein the cyclic group is substituted with 1 or at least 2 substituent(s).
36. The compound according to above mentioned 35, wherein the cyclic group with more than 2 substituent is

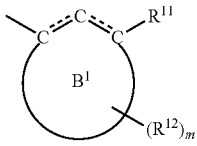

wherein $B^1$ represents a carbon ring of an aromatic ring,
$R^{11}$ and $R^{12}$ each represents a substituent,
m represents an integer of 1-4, and
the other symbols have the same meanings as those mentioned above.

37. The compound according to above mentioned 35, wherein the heterocyclic ring with at least 2 substituents is

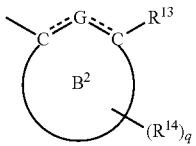

wherein $B^2$ represents a heterocyclic ring of an aromatic ring,
$R^{13}$ and $R^{14}$ each represents a substituent,
G represents carbon, nitrogen, oxygen, or sulfur,
q represents an integer of 1-4, and
the other symbols have the same meanings as those mentioned above.

38. The compound according to above mentioned 23, wherein the cyclic substituent is an unsaturated carbon ring.
39. The compound according to above mentioned 38, wherein the cyclic group optionally with a substituent(s) represented by B is an aromatic ring.

40. The compound according to above mentioned 38, wherein the cyclic group optionally with a substituent(s) represented by B is a nonaromatic ring.
41. The compound according to above mentioned 39, wherein the cyclic group is substituted with 1 or at least 2 substituent(s).
42. The compound according to above mentioned 41, wherein the cyclic group with at least 2 substituents is

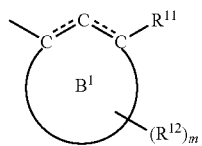

wherein $B^1$ represents a carbon ring of an aromatic ring,
$R^{11}$ and $R^{12}$ each represents a substituent,
m represents an integer of 1-4, and
the other symbols have the same meanings as those mentioned above.

43. The compound according to above mentioned 41, wherein the heterocyclic ring with at least 2 substituents is

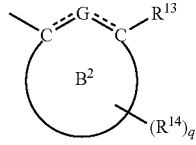

wherein $B^2$ represents a heterocyclic ring of an aromatic ring,
$R^{13}$ and $R^{14}$ each represents a substituent,
G represents carbon, nitrogen, oxygen, or sulfur,
q represents an integer of 1-4, and
the other symbols have the same meanings as those mentioned above.

44. The compound according to above mentioned 14, wherein the cyclic group optionally with a substituent(s) represented by B is an aromatic ring.
45. The compound according to above mentioned 14, wherein the cyclic group optionally with a substituent(s) represented by B is a nonaromatic ring.
46. The compound according to above mentioned 44, wherein the cyclic group is substituted with 1 or at least 2 substituent(s).
47. The compound according to above mentioned 46, wherein the cyclic group with at least 2 substituents is

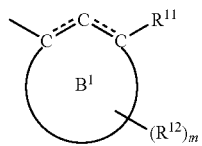

wherein $B^1$ represents a carbon ring of an aromatic ring,
$R^{11}$ and $R^{12}$ each represents a substituent
m represents an integer of 1-4, and
the other symbols have the same meanings as those mentioned above.

48. The compound according to above mentioned 46, wherein the heterocyclic ring with at least 2 substituents is

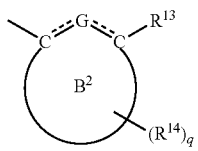

wherein B² represents a heterocyclic ring of an aromatic ring,
R¹³ and R¹⁴ each represents a substituent,
G represents carbon, nitrogen, oxygen, or sulfur,
q represents an integer of 1-4, and
the other symbols have the same meanings as those mentioned above.

49. The compound according to above mentioned 25, wherein the cyclic group optionally with a substituent(s) represented by B is an aromatic ring.

50. The compound according to above mentioned 25, wherein the cyclic group optionally with a substituent(s) represented by B is a nonaromatic ring.

51. The compound according to above mentioned 49, wherein the cyclic group is substituted with 1 or at least 2 substituent.

52. The compound according to above mentioned 51, wherein the cyclic group with at least 2 substituents is

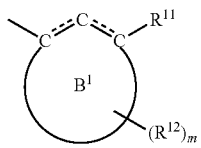

wherein B¹ represents a carbon ring of an aromatic ring,
R¹¹ and R¹² each represents a substituent,
M represents an integer of 1-4, and
the other symbols have the same meanings as those mentioned above.

53. The compound according to above mentioned 51, wherein the heterocyclic ring with at least 2 substituents is

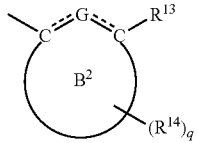

wherein B represents a heterocyclic ring of an aromatic ring,
R¹³ and R¹⁴ each represents a substituent,
G represents carbon, nitrogen, oxygen, or sulfur.
q represents an integer of 1-4, and
the other symbols have the same meanings as those mentioned above.

54. An EDG-5 antagonist comprising the compound represented by formula (I):

A-X—Y—Z—B    (I)

(wherein all the symbols have the same meanings as those of above mentioned 6), except a compound represented by formula (II):

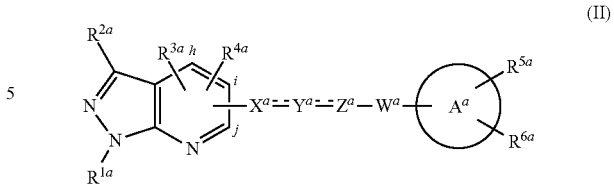

(wherein all the symbols have the same meanings as those of above mentioned 7) or
a pharmaceutically acceptable salt thereof.

55. An EDG-5 antagonist comprising the compound according to above mentioned 10, wherein the cyclic group optionally with a substituent(s) represented by A, or the cyclic group optionally with a substituent(s) represented by B is a C3-15 carbon ring, or an optionally saturated or unsaturated 3-15 membered monocyclic, bicyclic, or tricyclic aromatic heterocyclic ring (except pyrazolo[3,4-b]pyridine) containing 1-5 hetero atoms selected from an oxygen atom(s), a nitrogen atom(s), and/or a sulfur atom(s).

56. An EDG-5 antagonist comprising the compound according to above mentioned 10, wherein the cyclic group optionally with a substituent(s) represented by A and the cyclic group optionally with a substituent(s) represented by B is a monocyclic C3-15 carbon ring, or an optionally saturated or unsaturated 3-15 membered monocyclic aromatic heterocyclic ring containing 1-5 hetero atoms selected from an oxygen atom( s), a nitrogen atom(s), and/or a sulfur atom(s).

57. An EDG-5 antagonist comprising the compound according to above mentioned 10, wherein X is a single bond and the cyclic group optionally with a substituent(s) represented by B is a C3-15 carbon ring, or an optionally saturated or unsaturated 3-15 membered monocyclic aromatic heterocyclic ring containing 1-5 hetero atoms selected from an oxygen atom(s), a nitrogen atom(s), and/or a sulfur atom(s).

58. An EDG-5 antagonist comprising the compound according to above mentioned 10, wherein X binds to a nitrogen atom included in the cyclic group optionally with a substituent(s) represented by A and the cyclic group optionally with a substituent(s) represented by B is a C3-15 carbon ring, or an optionally saturated or unsaturated 3-15 membered monocyclic, bicyclic, or tricyclic aromatic heterocyclic ring containing 1-5 hetero atoms selected from 1-2 oxygen atom(s), 1-2 nitrogen atom(s), and/or 1-2 sulfur atom(s).

59. An EDG-5 antagonist comprising the compound according to above mentioned 19.

60. A prodrug of a compound represented by formula (I):

A-X—Y—Z—B    (I)

(wherein all the symbols have the same meanings as those of above mentioned 6) or
a prodrug of a pharmaceutically acceptable salt thereof.

61. A method for treatment and/or prevention of a disease due to constriction of blood vessels in a mammal, which comprises administrating to a mammal an effective dose of a compound represented by formula (I):

A-X—Y—Z—B    (I)

(wherein all the symbols have the same meanings as those of above mentioned 6) or
a pharmaceutically salt thereof.

62. A method for inhibition of EDG-5 in a mammal, which comprises administering to a mammal an effective dose of the compound according to above mentioned 10, wherein the cyclic group optionally with a substituent(s) represented by A, or the cyclic group optionally with a substituent(s) represented by B is a C3-15 carbon ring, or an optionally saturated or unsaturated 3-15 membered monocyclic, bicyclic, or tricyclic aromatic heterocyclic ring (except pyrazolo[3,4-b]pyridine) containing 1-5 hetero atoms selected from an oxygen atom(s), a nitrogen atom(s), and/or a sulfur atom(s).

63. A method for inhibition of EDG-5 in a mammal, which comprises administering to a mammal an effective dose of the compound according to above mentioned 10, wherein the cyclic group optionally with a substituent(s) represented by A, or the cyclic group optionally with a substituent(s) represented by B is a C3-15 monocyclic carbon ring, or an optionally saturated or unsaturated 3-15 membered monocyclic aromatic heterocyclic ring containing 1-5 hetero atoms selected from an oxygen atom(s), a nitrogen atom(s), and/or a sulfur atom(s).

64. A method for inhibition of EDG-5 in a mammal, which comprises administering to a mammal an effective dose of the compound according to above mentioned 10, wherein X is a single bond and the cyclic group optionally with a substituent(s) represented by B is a C3-15 monocyclic carbon ring, or an optionally saturated or unsaturated 3-15 membered monocyclic aromatic heterocyclic ring containing 1-5 hetero atoms selected from an oxygen atom(s), a nitrogen atom(s), and/or a sulfur atom(s).

65. A method for inhibition of EDG-5 in a mammal, which comprises administering to a mammal an effective dose of the compound according to above mentioned 10, wherein X binds to a nitrogen atom included in the cyclic group optionally with a substituent(s) represented b y A and the cyclic group optionally with a substituent(s) represented by B is a C3-15 carbon ring, or an optionally saturated or unsaturated 3-15 membered monocyclic, bicyclic, or tricyclic aromatic heterocyclic ring containing 1-5 hetero atoms selected from 1-2 oxygen atom(s), 1-2 nitrogen atom(s), and/or 1-2 sulfur atom(s).

66. Use of a compound represented by formula (I):

A-X—Y—Z—B     (I)

(wherein all the symbols have the same meanings as those of above mentioned 6) or
a pharmaceutically salt thereof, for producing a therapeutic and/or preventing agent of a disease due to constriction of blood vessels.

67. Use of the compound according to above mentioned 10, for producing an EDG-5 antagonist, wherein the cyclic group with optionally a substituent(s) represented by A, or the cyclic group optionally with a substituent(s) represented by B is a C3-15 carbon ring, or an optionally saturated or unsaturated 3-15 membered monocyclic, bicyclic, or tricyclic aromatic heterocyclic ring (except pyrazolo[3, 4-b]pyridine) containing 1-5 hetero atoms selected from an oxygen atom(s), a nitrogen atom(s), and/or a sulfur atom(s).

68. Use of the compound according to above mentioned 10, for producing an EDG-5 antagonist, wherein the cyclic group optionally with a substituent(s) represented by A, and the cyclic group optionally with a substituent(s) represented by B is a C3-15 monocyclic carbon ring, or an optionally saturated or unsaturated 3-15 membered monocyclic aromatic heterocyclic ring containing 1-5 hetero atoms selected from an oxygen atom(s), a nitrogen atom(s), and/or a sulfur atom(s).

69. Use of the compound according to above mentioned 10, for producing an EDG-5 antagonist, wherein X is a single bond and the cyclic group optionally with a substituent(s) represented by B is a C3-15 monocyclic carbon ring, or an optionally saturated or unsaturated 3-15 membered monocyclic aromatic heterocyclic ring containing 1-5 hetero atoms selected from an oxygen atom(s), a nitrogen atom(s), and/or a sulfur atom(s).

70. Use of the compound according to above mentioned 10, for producing an EDG-5 antagonist, wherein X binds to a nitrogen atom included in the cyclic group optionally with a substituent(s) represented by A and the cyclic group optionally with a substituent(s) represented by B is a C3-15 carbon ring, or an optionally saturated or unsaturated 3-15 membered monocyclic, bicyclic, or tricyclic aromatic heterocyclic ring containing 1-5 hetero atoms selected from an oxygen atom(s), a nitrogen atom(s), and/or a sulfur atom(s).

In the present specification, "cyclic group" in the cyclic group optionally with a substituent(s) represented by A means C3-15 carbon ring, or optionally saturated or unsaturated 3-15 membered monocyclic, bicyclic, or tricyclic aromatic heterocyclic ring containing 1-5 hetero atoms selected from an oxygen atom(s), a nitrogen atom(s), and/or a sulfur atom(s).

C3-15 carbocyclic ring used in the present specification includes monocyclic, bicyclic or tricyclic aromatic carbocyclic ring having carbon numbers of 3 to 15, unsaturated or saturated carbocyclic ring, spiro linked bicyclic carbocyclic ring and bridged bicyclic carbocyclic ring. Concretely, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphtene, fluorene, phenalene, phenanthrene, anthracene, spiro[4.4]nonane, spiro[4.5]decane, spiro [5.5]undecane, bicyclo[2.2.1]heptane, bicyclo[2.2.1]hept-2-ene, bicyclo[3.1.1]heptane, bicyclo[3.1.1]hept -2-ene, bicyclo[2.2.2]octane, bicyclo[2.2.2]oct-2-ene, adamantane, noradamantane and the like. In the present specification, optionally saturated or unsaturated 3-15 membered monocyclic, bicyclic, or tricyclic aromatic heterocyclic ring containing 1-5 hetero atoms selected from 1-2 oxygen atom(s), 1-2 nitrogen atom(s), and/or 1-2 sulfur atom(s) means, concretely, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzoazepin, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrazolopyridine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydro pyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisohenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophtlialazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro [5.5]undecane, dioxaspiro[5.5]undecane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, tetrahydro-beta-carboline, hexahydroazepinoindole, oxazaspiro[2.5]octane, hexahydroazepinoindazole, hexahydropyrazolopyridoazepine, tetrahydropyrazoloisoquinoline, tetrahydropyrazolonaphthyridine and the like.

In the specification, "substituent" in the cyclic group optionally with a substituent(s) represented by A means, concretely, (1) alkyl optionally with a substituent(s), (2) alkenyl optionally with a substituent(s), (3) alkynyl optionally with a substituent(s), (4) carbocyclic ring optionally with a substituent(s), (5) heterocyclic ring optionally with a substituent(s), (6) hydroxyl optionally with a substituent(s), (7) thiol optionally with a substituent(s), (8) amino optionally with a substituent(s), (9) carbamoyl optionally with a substituent(s), (10) sulfamoyl optionally with a substituent(s), (11) carboxyl, (12) alkoxycarbonyl (C1-6 alkoxycarbonyl, such as methoxycarbonyl, ethoxycarbonyl, tert-butoxycarbonyl and the like), (13) sulfo (—$SO_3H$), (14) sulfino, (15) phosphono, (16) nitro, (17) cyano, (18) amidino, (19) imino, (20) —$B(OH)_2$, (21) halogen (such as fluorine, chlorine, bromine, iodine and the like), (22) alkylsulfinyl (C1-4 alkylsulfinyl such as methylsulfinyl, ethylsulfinyl and the like), (23) aromatic ring sulfinyl (C6-10 aromatic ring sulfinyl, such as phenylsulfinyl), (24) alkylsulfonyl (C1-4 alkylsulfonyl, such as methylsulfonyl, ethylsulfonyl and the like), (25) aromatic ring sulfonyl (C6-10 aromatic ring sulfonyl, such as phenylsulfonyl and the like), (26) acyl (C1-6 alkanoyl, such as formyl, acetyl, propanoyl, pivaloyl and the like. C6-10 aromatic ring carbonyl, such as benzoyl and the like), (27) oxo, (28) thioxo, (29) (C1-6 alkoxyimino)methyl (such as (methoxyimino)methyl and the like) and the like. One to five out of these optional substituents may substitute to the replaceable position. Alkyl in the "alkyl optionally with a substituent(s)" as the substituent means, concretely, methyl, ethyl, n -propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and straight-chain or branched-chain C1-20 alkyl. Here, substituent of alkyl means, concretely, hydroxyl, amino, carboxyl, nitro, mono- or di-C1-6 alkylamino (such as methylamino, ethylamino, propylamino, dimethylamino, diethylamino and the like), N-aromatic ring amino (such as N-phenylamino and the like), N-aromatic ring-N-alkylamino (such as N-phenyl-N-methylamino, N-phenyl-N-ethylamino, N-phenyl-N-propylamino, N-phenyl-N-butylamino, N-phenyl-N-pentylamino, N-phenyl-N-hexylamino and the like), acylamino, N-acyl-N-alkylamino, C1-6 alkoxy (such as methoxy, ethoxy, propoxy, isopropoxy, hexyloxy and the like), C3-7 cycloalkyl-C1-6-alkoxy (such as cyclohexylmethyloxy, cyclopentylethyloxy and the like), C3-7 cycloalkyloxy (such as cyclohexyloxy and the like), C7-15 aralkyloxy (such as benzyloxy, phenethyloxy, phenylpropyloxy, naphthylmethyloxy, naphthylethyloxy and the like), phenoxy, C1-6 alkoxycarbonyl (such as methoxycarbonyl, ethoxycarbonyl, tert-butoxycarbonyl and the like), C1-6 alkylcarbonyloxy (such as acetoxy, ethylcarbonyloxy and the like), C1-4 alkylthio (such as methylthio, ethylthio, propylthio, butylthio and the like), halogen atom (fluorine, chlorine, bromine, iodine), alkylsulfonyl (C1-4 alkylsulfonyl, such as methylsulfonyl, ethylsulfonyl and the like), aromatic ring sulfonyl (C6-10 aromatic ring sulfonyl, such as phenylsulfonyl and the like), acyl (C1-6 alkanoyl, such as formyl, acetyl, propanoyl, pivaloyl and the like, and C6-10 aromatic ring carbonyl, such as benzoyl and the like), carbocyclic ring optionally with a substituent(s), heterocyclic ring optionally with a substituent(s) and the like. One to four out of these optional substituents may substitute to the replaceable position. Here, acylamino as substituent of alkyl and acyl in N-acyl-N—(C1-6 alkyl) amino have the same meaning as "hydroxyl optionally with a substituent(s)" as the substituent, acyl as the substituent in "thiol optionally with a substituent(s)" and "amino optionally with a substituent(s)" as described later. "alkyl" in the N-acyl-N-alkylamino means, concretely, methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and straight-chain or branched-chain C1-20 alkyl. Carbocyclic ring as the alkyl substituent means optionally saturated or unsaturated 3-15 membered monocyclic, bicyclic, or tricyclic aromatic carbocyclic ring and the like. Optionally saturated or unsaturated 3-15 membered monocyclic, bicyclic, or tricyclic aromatic carbocyclic ring means, concretely, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphtene, fluorene, phenalene, phenanthrene, anthracene and the like. In addition, optionally saturated or unsaturated 3-15 membered monocyclic, bicyclic, or tricyclic aromatic heterocyclic ring includes spiro linked bicyclic carbocyclic ring and bridged bicyclic carbocyclic ring. Concretely, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane and the like. Here, substituent of carbocyclic ring as alkyl substituent means C1-8 alkyl (such as methyl, ethyl, n-propyl, isopropyl, n-butyl, isobutyl, sec-butyl, tert-butyl, pentyl, hexyl, heptyl, octyl and the like), hydroxyl, amino, carboxyl, nitro, mono- or di-C1-6 alkylamino (such as methylamino, ethylamino, propylamino, dimethylamino, diethylamino and the like), C1-6 alkoxy (such as methoxy, ethoxy, propoxy, hexyloxy and the like), C1-6 alkoxycarbonyl (such as methoxycarbonyl, ethoxycarbonyl, tert-butoxycarbonyl and the like), C1-6 alkylcarbonyloxy (such as acetoxy, ethylcarbonyloxy and the like), C1-4 alkylthio (such as methylthio, ethylthio, propylthio, butylthio and the like), halogen atom (such as fluorine, chlorine, bromine, iodine), trihalomethyl (such as trifuloromethyl and the like) and the like. One to four out of these optional substituents may substitute to the replaceable position. Heterocyclic ring as alkyl substituent means optionally saturated or unsaturated 3-15 membered monocyclic aromatic heterocyclic ring containing 1-5 hetero atoms selected from oxygen atoms, nitrogen atoms, or sulfur atoms. 3-15 membered monocyclic aromatic heterocyclic ring containing 1-5 hetero atoms selected from oxygen atoms, nitrogen atoms, or sulfur atoms out of optionally saturated or unsaturated 3-15 membered monocyclic aromatic heterocyclic ring containing 1-5 hetero atoms selected from oxygen atoms, nitrogen atoms, or sulfur atoms means, concretely, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofiuran, isobenzofuran, benzothiophene, isobenzoihiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine and the like. Saturated or unsaturated 3-15 membered monocyclic aromatic heterocyclic ring containing 1-5 hetero atoms selected from oxygen atoms, nitrogen atoms, or sulfur atoms out of optionally saturated or unsaturated 3-15 membered monocyclic aromatic heterocyclic ring containing 1-5 hetero atoms selected from oxygen atoms, nitrogen atoms, or sulfur atoms means, concretely, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), di hydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane and the like. Here, substituent of heterocyclic ring as the alkyl substituent means C1-8 alkyl (such as methyl, ethyl, n-propyl, isopropyl, n-butyl, isobutyl, sec-butyl, tert-butyl, pentyl, hexyl, heptyl, octyl and the like), hydroxyl, amino, carboxyl, nitro, mono- or di-C1-6 alkylamino (such as methylamino, ethylamino, propylamino, dimethylamino, diethylamino and the like), C1-6 alkoxy (such as methoxy, ethoxy, propoxy, hexyloxy and the like), C1-6 alkoxycarbonyl (such as methoxycarbonyl, ethoxycarbonyl, tert-butoxycarbonyl and the like), C1-6 alkylcarbonyloxy (such as acetoxy, ethylcarbonyloxy and the like), C1-4 alkylthio (such as methylthio, ethylthio, propylthio, butylthio and the like), halogen atom (such as fluorine, chlorine, bromine, iodine) and the like. One to four out of these optional substituents may substitute to the replaceable position. Alkenyl in the "alkenyl optionally with a substituent(s)" as substituent means straight-chain or branched-chain C2-6 alkenyl, such as ethenyl, propenyl, butenyl, pentenyl, hexenyl and the like. Here, substituents of alkenyl have the same meaning as above-mentioned substituents in "alkenyl optionally with a substituent(s)". Alkynyl in the "alkynyl optionally with a substituent(s)" as substituent means straight-chain or branched-chain C2-6 alkynyl, such as ethynyl, propynyl, butynyl, pentynyl, hexynyl and the like. Here, substituents of alkynyl have the same meaning as above-mentioned substituents in "alkenyl optionally with a substituent(s)". Carbocyclic ring in "carbocyclic ring optionally with a substituent(s)" as substituent means optionally saturated or unsaturated 3-15 membered monocyclic, bicyclic, or tricyclic aromatic carbocyclic ring and the like. Optionally saturated or unsaturated 3-15 membered monocyclic, bicyclic, or tricyclic aromatic carbocyclic ring means cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadierie, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphtene, fluorene, phenalene, phenanthrene, anthracene and the like. In addition, optionally saturated or unsaturated 3-15 membered monocyclic, bicyclic, or tricyclic aromatic carbocyclic ring includes spiro linked bicyclic carbocyclic ring and bridged bicyclic carbocyclic ring. Concretely, spiro[4.4]nonane, spiro [4.5]decane, spiro[5.5]undecane, bicyclo[2.2.1]heptane, bicyclo[2.2.1]hept-2-ene, bicyclo[3.1.1]heptane, bicyclo [3.1.1]hept-2-ene, bicyclo[2.2.2]octane, bicyclo[2.2.2]oct-2-ene, adamantane, noradamantane and the like. Here, substituent of carbocyclic ring means C1-4 alkyl (such as methyl, ethyl, propyl, butyl and the like), C2-4 alkenyl (such as ethenyl, propenyl, butenyl and the like), C2-4 alkynyl (such as ethynyl, propynyl, butynyl and the like), hydroxyl, C1-4 alkoxy (such as methoxy, ethoxy, propoxy, butoxy and the like), C1-6 alkoxycarbonyl (such as methoxycarbonyl, ethoxycarbonyl, tert-butoxycarbonyl and the like), thiol, C1-4 alkylthio (such as methylthio, ethylthio, propylthio, butylthio and the like), amino, mono- or di-C1-4 alkylamino (such as methylamino, ethylamino, propylamino, dimethylamino, diethylamino and the like), halogen atom (such as fluorine, chlorine, bromine, iodine), trihalomethyl (such as trifuloromethyl and the like), trihalomethoxy (such as trifuloromethoxy and the like), trihalomethylthio (such as trifuloromethylthio and the like), dihalomethylthio (such as difuloromethylthio and the like), cyclic group optionally with a substituent(s), cyano, nitro and the like. One to four out of these optional substituents may substitute to the replaceable position. Here, cyclic group optionally with a substituent(s) as substituent of carbocyclic ring in "carbocyclic ring optionally with a substituent(s)" as substituent has the same meaning as above mentioned "cyclic group" in cyclic ring optionally with a substituent(s) represented by A. Substituent of cyclic group optionally with a substituent(s) as substituent of carbocyclic ring in "carbocyclic ring optionally with a substituent(s)" as substituent have the same meaning as above mentioned substituent of carbocyclic ring as substituent of "alkyl optionally with a substituent(s)" as substituent. One to four out of these optional substituents may substitute to the replaceable position. Heterocyclic ring in "heterocyclic ring optionally with a substituent(s)" as substituent means optionally saturated or unsaturated 3-15 membered monocyclic aromatic heterocyclic ring containing 1-5 hetero atoms selected from oxygen atoms, nitrogen atoms, or sulfur atoms. 3-15 membered monocyclic aromatic heterocyclic ring containing 1-5 hetero atoms selected from oxygen atoms, nitrogen atoms, or sulfur atoms out of optionally saturated or unsaturated 3-15 membered monocyclic aromatic heterocyclic ring containing 1-5 hetero atoms selected from oxygen atoms, nitrogen atoms, or sulfur atoms means, concretely, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine and the like. Saturated or unsaturated 3-15 membered monocyclic aromatic heterocyclic ring containing 1-5 hetero atoms selected from oxygen atoms, nitrogen atoms, or sulfur atoms out of optionally saturated or unsaturated 3-15 membered monocyclic aromatic heterocyclic ring containing 1-5 hetero atoms selected from oxygen atoms, nitrogen atoms, or sulfur atoms means, concretely, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophcne, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, ben zodioxane, chroman, benzodithiolane, benzodithiane and the like. Here, substituent of heterocyclic ring has the same meaning as the above mentioned substituent in "carbocyclic ring optionally with a substituent(s)". One to four out of these optional substituents may substitute to the replaceable position. Substituent in "hydroxyl optionally with a substituent(s)", "thiol optionally with a substituent(s)" and "amino optionally with a substituent(s)" as substituent mean alkyl optionally with a substituent(s) (it has the same meaning as the above mentioned "alkyl optionally with a substituent(s)"), carbocyclic ring optionally with a substituent(s) (it has the same meaning as the above mentioned "carbocyclic ring optionally with a substituent(s)"), heterocyclic ring optionally with a substituent(s) (it has the same meaning as the above mentioned "heterocyclic ring optionally with a substituent(s)"), alkylsulfonyl (C1-4 alkylsulfonyl, such as methylsulfonyl, ethylsulfonyl and the like), heterocyclic ring sulfonyl (C6-10 heterocyclic ring sulfonyl, such as phenylsulfonyl and the like), acyl and the like. Here, acyl means (1) alkylcarbonyl optionally with a substituent(s), (2) alkenylcarbonyl optionally with a substituent(s), (3) alkynylcarbonyl optionally with a substituent(s), (4) carbocyclic ring carbonyl optionally with a substituent(s), (5) heterocyclic ring carbonyl optionally with a substituent(s) and the like. One to four out of these optional substituents may substitute to the replaceable position. Alkyl optionally with a substituent(s) in "alkylcarbonyl optionally with a substituent(s)" has the same meaning as the above mentioned "alkyl optionally with a substituent(s)". Alkenyl optionally with a substituent(s) in "alkenylcarbonyl optionally with a substituent(s)" has the same meaning as the above mentioned "alkenyl optionally with a substituent(s)". Alkynyl optionally with a substituent(s) in "alkynylcarbonyl optionally with a substituent(s)" has the same meaning as the above mentioned "alkynyl option ally with a substituent(s)". Carbocyclic ring optionally with a substituent(s) in "carbocyclic ring carbonyl optionally with a substituent(s)" has the same meaning as the above mentioned "carbocyclic ring optionally with a substituent(s)". Heterocyclic ring optionally with a substituent(s) in "heterocyclic ring carbonyl optionally with a substituent(s)" has the same meaning as the above mentioned "heterocyclic ring optionally with a substituent(s)". "Carbamoyl optionally with a substituent(s)" as substituent means, concretely, carbamoyl with no substituent, N-mono-C1-4 alkylcarbamoyl (such as N-methylcarbamoyl, N-ethylcarbamoyl, N-propylcarbamoyl, N-isopropylcarbamoyl, N-butylcarbamoyl and the like), N,N-diC1-4 alkylcarbamoyl (such as N,N-dimethylcarbamoyl, N,N-diethylcarbamoyl, N,N-dipropylcarbamoyl, N,N-dibutylcarbamoyl and the like), 1-pyperidylcarbonyl and the like. "Sulfamoyl optionally with a substituent(s)" as substituent means, concretely, sulfamoyl with no substituent, N-mono-C1-4 alkylsulfamoyl (such as N-methylsulfamoyl, N-ethylsulfamoyl, N-propylsulfamoyl, N-isopropylsulfamoyl, N-butylsulfamoyl and the like), N,N-di-C1-4 alkylsulfamoyl (such as N,N-dimethylsulfamoyl, N,N-diethylsulfamoyl, N,N-dipropylsulfamoyl, N,N-dibutylsulfamoyl and the like) and the like.

In the specification, "cyclic group" in cyclic group optionally with a substituent(s) represented by B means the same meaning as the above mentioned cyclic group in "cyclic group optionally with a substituent(s) represented by A".

In the specification, "substituent" in cyclic group optionally with a substituent(s) represented by B means the same meaning as the above mentioned substituent in "cyclic group optionally with a substituent(s) represented by A".

In the specification, "spacers of principal chain atomicity are 1-3" represented by X means the interval which 1-3 principal chain atoms continue into. Here, "principal chain atomicity" can be counted so that principal chain atoms come to be minimized. "Spacers of principal chain atomicity are 1-3" means bivalent group consisted of 1-3 selected from, such as methylene ($-CH_2-$) optionally with 1 or 2 substituent, nitrogen atom ($-NH-$) optionally with a substituent(s), $-CO-$, $-O-$, $-S-$, $-SO-$, $-SO_2-$. Here, substituent of methylene and substituent of nitrogen atom have the same meaning as the above mentioned "substituent" in cyclic group optionally with a substituent(s) represented by A. Concretely, $-CH_2-$, $-CHR^{101}-$, $-CR^{101}R^{102}-$, $-NH-$, $-NR^{103}-$, $-CO-$, $-O-$, $-S-$, $-NHCO-$, $-NR^{103}CO-$, $-CONH-$, $-CONR^{103}-$, $-NR^{103}COCR^{101}R^{102}-$, $-CONR^{103}CR^{101}R^{102}-$ and the like (wherein $R^{101}$—$R^{103}$ have the same meaning as the above mentioned "substituent" in cyclic group optionally with a substituent(s) represented by A).

In the specification, "spacers of principal chain atomicity are 1-3" represented by Y have the same meaning as the above mentioned "spacers of principal chain atomicity are 1-3" represented by X.

In the specification, "spacers of principal chain atomicity are 1-3" represented by Z have the same meaning as the above mentioned "spacers of principal chain atomicity are 1-3" represented by X.

In the specification, C3-15 monocyclic carbon ring means, concretely cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene and the like.

In the specification, saturated or unsaturated 3-15 membered monocyclic aromatic heterocyclic ring containing 1-5 hetero atoms selected from oxygen atoms, nitrogen atoms and/or sulfur atoms means, concretely, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane and the like. In the specification, saturated or unsaturated 4-15 membered bicyclic or tricyclic aromatic heterocyclic ring containing 1-5 hetero atoms selected from oxygen atoms, nitrogen atoms and/or sulfur atoms means, concretely, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenz othiophene, dioxaindan, benzodioxane, chroman, benzodithiolane, benzodithiane, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, tetrahydro-beta-carboline, hexahydroazepino[3.4-b]indole, hexahydroazepinoindazole, hexahydropyrazolopyridoazepine, tetrahydropyrazoloisoquinoline, leirahydropyrazolonaphthyridine and the like.

In the specification, optionally saturated or unsaturated 3-15 membered monocyclic, bicyclic, or tricyclic aromatic heterocyclic ring containing 1-5 hetero atoms selected from 1-2 oxygen atom(s), 1-2 nitrogen atom(s), and/or 1-2 sulfur atom(s) means, concretely, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, phthalazine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, pyrazoline, pyrazolidine, dihydropyri dine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhoydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, tetrahydro-beta-carboline, hexahydroazepino[3,4-b]indole and the like.

In the specification, saturated carbocyclic ring means, concretely, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, perhydropentalene, azulene, perhydroazulene, perhydroindene, perhydronaphthalene, perhydroheptalene, spiro[4.4]nonane, spiro[4.5]decane, spiro[5.5]undecane, bicyclo[2.2.1]heptane, bicyclo[3.1.1]heptane, bicyclo[2.2.2]octane, adamantane, noradamantane and the like.

In the specification, unsaturated carbocyclic ring means, concretely, cyclopentene, cyclohexene, cycloheptene, cyclooctene, cyclopentadiene, cyclohexadiene, cycloheptadiene, cyclooctadiene, benzene, pentalene, azulene, indene, indane, naphthalene, dihydronaphthalene, tetrahydronaphthalene, heptalene, biphenylene, as-indacene, s-indacene, acenaphthylene, acenaphtene, fluorene, phenalene, phenanthrene, anthracene, bicyclo[2.2.1]hept-2-ene, bicyclo[3.1.1]hept-2-ene, bicyclo[2.2.2]oct-2-ene and the like.

In the specification, aromatic ring means, concretely, benzene, azulene, naphthalene, phenanthrene, anthracene, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, beta-carboline, acridine, phenazine, dibenzofuran, dibenzothiophene, phenanthridine, phenanthroline, perimidine and the like.

In the specification, nonaromatic ring means, concretely, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, pentalene, perhydropentalene, perhydroazulene, indene, perhydroindene, indane, dihydronaphthalene, tetrahydronaphthalene, perhydronaphthalene, heptalene, perhydroheptalene, biphenylene, as-indacene, s-indacene, acenaphthylene, acenaphtene, fluorene, phenalene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane, azepine, diazepine, pyran, oxepine, thiopyran, thiepine, oxazine, oxadiazine, oxazepine, oxadiazepine, thiazine, thiadiazine, thiazepine, thiadiazepine, indolizine, dithianaphthalene, quinolizine, chromene, benzoxepine, benzoxazepine, benzoxadiazepine, benzothiepine, benzothiazepine, benzothiadiazepine, benzazepine, benzodiazepine, xanthene, phenothiazine, phenoxazine, phenoxathiin, thianthrene, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, azaspiro[4.4]nonane, oxazaspiro[4.4]nonane, dioxaspiro[4.4]nonane, azaspiro[4.5]decane, thiaspiro[4.5]decane, dithiaspiro [4.5]decane, dioxaspiro[4.5]decane, oxazaspiro[4.5]decane, azaspiro[5.5]undecane, oxaspiro[5.5]undecane, dioxaspiro[5.5]undecane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, tetrahydro-beta-carboline, hexahydroazepinoindole, hexahydroazepinoindazole, hexahydropyrazolopyridoazepine, tetrahydropyrazoloisoquinoline, tetrahydropyrazolonaphthyridine and the like.

In the specification, carbocyclic ring of aromatic ring means benzene, azulene, naphthalene, phenanthrene, anthracene and the like.

In the specification, heterocyclic ring of aromatic ring means, concretely, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, beta-carboline, acridine, phenazine, dibenzofuran, dibenzothiophene, phenanthridine, phenanthroline, perimidine and the like.

The substituents represented by $R^1, R^3, R^4, R^6, R^7, R^9, R^{11}, R^{12}, R^{13}, R^{14}, R^{15}$ and $R^{16}$ have the same meaning as the "substituent" in cyclic group optionally with a substituent(s) represented by A.

The substituent represented by $R^{17}$, $R^{18}$, $R^{19}$ and $R^{20}$ means, concretely, (1) alkyl optionally with a substituent(s), (2) alkenyl optionally with a substituent(s), (3) alkynyl optionally with a substituent(s), (4) carbocyclic ring optionally with a substituent(s), (5) heterocyclic ring optionally with a substituent(s), (6) hydroxyl optionally with a substituent(s), (7) thiol optionally with a substituent(s), (8) amino optionally with a substituent(s), (9) carbamoyl optionally with a substituent(s), (10) sulfamoyl optionally with a substituent(s), (11) carboxyl, (12) alkoxycarbonyl (C1-6 alkoxycarbonyl, such as methoxycarbonyl, ethoxycarbonyl, tert-butoxycarbonyl and the like), (13) sulfo (—SO$_3$H), (14) sulfino, (15) phosphono, (16) nitro, (17) cyano, (18) amidino, (19) imino group, (20) —B(OH)$_2$, (21) alkylsulfynyl (C1-4 alkylsulfynyl such as methylsulfynyl, ethylsulfynyl and the like), (22) aromatic ring sulfynyl (C6-10 aromatic ring sulfynyl such as phenylsulfynyl and the like), (23) alkylsulfonyl (C1-4 alkylsulfonyl such as methylsulfonyl, ethylsulfonyl and the like), (24) aromatic ring sulfonyl (C6-10 aromatic ring sulfonyl such as phenylsulfonyl and the like), (25) acyl (C1-6 alkanoyl, such as formyl, acetyl, propanoyl, pivaloyl and the like. C6-10 aromatic ring carbonyl, such as benzoyl and the like), (26) oxo, (27) thioxo, (28) (C1-6 alkoxyimino) methyl (such as (methoxyimino)methyl and the like) and the like. One to five out of these optional substituents may substitute to the replaceable position. Alkyl in the "alkyl optionally with a substituent(s)" as the substituent means, concretely, methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and straight-chain or branched-chain C1-20 alkyl. Here, substituent of alkyl means, concretely, hydroxyl, amino, carboxyl, nitro, mono- or di-C1-6 alkylamino (such as methylamino, ethylamino, propylamino, dimethylamino, diethylamino and the like), N-aromatic ring amino (such as N-phenylamino and the like), N-aromatic ring-N-alkylamino (such as N-phenyl-N-methylamino, N-phenyl-N-ethylamino, N-phenyl-N-propylamino, N-phenyl-N-butylamino, N-phenyl-N-pentylamino, N-phenyl-N-hexylamino and the like), acylamino, N-acyl-N-alkylamino, C1-6 alkoxy (such as methoxy, ethoxy, propoxy, isopropoxy, hexyloxy and the like), C3-7 cycloalkyl-C1-6-alkoxy (such as cyclohexylmethyloxy, cyclopentylethyloxy and the like), C3-7 cycloalkyloxy (such as cyclohexyloxy and the like), C7-15 aralkyloxy (such as benzyloxy, phenethyloxy, phenylpropyloxy, naphthylmethyloxy, naphthylethyloxy and the like), phenoxy, C1-6 alkoxycarbonyl (such as methoxycarbonyl, ethoxycarbonyl, tert-butoxycarbonyl and the like), C1-6 alkylcarbonyloxy (such as acetoxy, ethylcarbonyloxy and the like), C1-4 alkylthio (such as methylthio, ethylthio, propylthio, butylthio and the like), alkylsulfonyl (C1-4 alkylsulfonyl, such as methylsulfonyl, ethylsulfonyl and the like), aromatic ring sulfonyl (C6-10 aromatic ring sulfonyl, such as phenylsulfonyl and the like), oxo, carbocyclic ring optionally with a substituent(s), heterocyclic ring optionally with a substituent(s) and the like. One to four out of these optional substituents may substitute to the replaceable position. Here, acylamino and acyl in N-acyl-N—(C1-6 alkyl) amino as a substituent of alkyl have the same meaning as the after mentioned "hydroxyl optionally with a substituent(s)" as substituent, acyl in "thiol optionally with a substituent(s)" and "amino optionally with a substituent(s)" as substituent. "alkyl" in N-acyl-N-alkylamino means, concretely, methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and linear or branched C1-20 alkyl. Carbocyclic ring as substituent of alkyl means optionally saturated or unsaturated C3-15 membered monocyclic, bicyclic, or tricyclic aromatic carbocyclic ring. Optionally saturated or unsaturated C3-15 membered monocyclic, bicyclic, or tricyclic aromatic carbocyclic ring means, concretely, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphtene, fluorene, phenalene, phenanthrene, anthracene and the like. In addition, optionally saturated or unsaturated C3-15 monocyclic, bicyclic or tricyclic aromatic carbocyclic ring including spiro linked bicyclic carbocyclic ring and bridged bicyclic carbocyclic ring means, concretely, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane and the like. Here, substituent of carbocyclic ring as substituent of alkyl means, concretely, C1-8 alkyl (such as methyl, ethyl, n-propyl, isopropyl, n-butyl, isobutyl, sec-butyl, tert-butyl, pentyl, hexyl, heptyl, octyl and the like), hydroxyl, amino, carboxyl, nitro, mono- or di-C1-6-alkylamino (such as methylamino, ethylamino, propylamino, dimethylamino, diethylamino and the like), C1-6 alkoxy (such as methoxy, ethoxy, propoxy, hexyloxy and the like), C1-6 alkoxycarbonyl (such as methoxycarbonyl, ethoxycarbonyl, tert-butoxycarbonyl and the like), C1-6 alkylcarbonyloxy (such as acetoxy, ethylcarbonyloxy and the like), C1-4 alkylthio (such as methylthio, ethylthio, propylthio, butylthio and the like), halogen atom (fluorine, chlorine, bromine, iodine), trihalomethyl (such as trifuloromethyl and the like) and the like. One to four out of these optional substituents may substitute to the replaceable position. Heterocyclic ring as substituent of alkyl means optionally saturated or unsaturated 3-15 membered monocyclic, bicyclic or tricyclic aromatic heterocyclic ring containing 1-5 hetero atoms selected from an oxygen atom(s), a nitrogen atom(s), and/or a sulfur atom(s). 3-15 membered monocyclic, bicyclic or tricyclic aromatic heterocyclic ring containing 1-5 hetero atoms selected from an oxygen atom(s), a nitrogen atom(s), and/or a sulfur atom(s) of optionally saturated or unsaturated 3-15 membered monocyclic, bicyclic or tricyclic aromatic heterocyclic ring containing 1-5 hetero atoms selected from an oxygen atom(s), a nitrogen atom(s), and/or a sulfur atom(s) means, concretely, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine and the like. Saturated or unsaturated 3-15 membered monocyclic, bicyclic or tricyclic aromatic heterocyclic ring containing 1-5 hetero atoms selected from an oxygen atom(s), a nitrogen atom(s), and/or a sulfur atom(s) of optionally saturated or unsaturated 3-15 membered monocyclic, bicyclic or tricyclic aromatic heterocyclic ring containing 1-5 hetero atoms selected from an oxygen atom(s), a nitrogen atom(s), and/or a sulfur atom(s) means, concretely, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane and the like. Here, the substituent of heterocyclic ring as substituent of alkyl means C1-8 alkyl (such as methyl, ethyl, n-propyl, isopropyl, n-butyl, isobutyl, sec-butyl, tert-butyl, pentyl, hexyl, heptyl, octyl and the like), hydroxyl, amino, carboxyl, nitro, mono-or di-C1-C6 alkylamino (such as methylamino, ethylamino, propylamino, dimethylamino, diethylamino and the like), C1-6 alkoxy (such as methoxy, ethoxy, propoxy, hexyloxy and the like), C1-6 alkoxycarbonyl (such as methoxycarbonyl, ethoxycarbonyl, tert -butoxycarbonyl and the like), C1-6 alkylcarbonyloxy (such as acetoxy, ethylcarbonyloxy and the like), C1-4 alkylthio (such as methylthio, ethylthio, propylthio, butylthio and the like), halogen atom (such as fluorine, chlorine, bromine, iodine and the like) and the like. One to four of these optional substituents may substitute to the replaceable position. Alkenyl in "alkenyl optionally with a substituent(s)" as substituent means straight-chain or branched-chain C2-6 alkenyl, such as ethenyl, propenyl, butenyl, pentenyl, hexenyl and the like. Here, substituents of alkenyl have the same meaning as the above mentioned substituent in "alkyl optionally with a substituent(s)". Alkynyl in "alkynyl optionally with a substituent(s)" as substituent means straight-chain or branched-chain C2-6 alkynyl, such as ethynyl, propynyl, butynyl, pentynyl, hexynyl and the like. Here, substituents of alkynyl have the same meaning as the above mentioned substituent in "alkyl optionally with a substituent(s)". Carbocyclic ring in "carbocyclic ring optionally with a substituent(s)" as substituent means optionally saturated or unsaturated C3-15 membered monocyclic, bicyclic, or tricyclic carbocyclic ring and the like. Optionally saturated or unsaturated C3-15 membered monocyclic, bicyclic, or tricyclic aromatic carbocyclic ring means, concretely, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, heptalene, perhydroheptalene, biphenylene, as-indacene, s-indacene, acenaphthylene, acenaphtene, fluorene, phenalene, phenanthrene, anthracene and the like. In addition, optionally saturated or unsaturated 3-15 membered monocyclic, bicyclic, or tricyclic aromatic carbocyclic ring includes spiro linked bicyclic carbocyclic ring and bridged bicyclic carbocyclic ring. Concretely, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane, noradamantane and the like. Here, substituent of carbocyclic ring means, concretely, C1-4 alkyl (such as methyl, ethyl, propyl, butyl and the like), C2-4 alkenyl (such as ethenyl, propenyl, butenyl and the like), C2-4 alkynyl (such as ethynyl, propynyl, butynyl and the like), hydroxyl, C1-4 alkoxy (such as methoxy, ethoxy, propoxy, butoxy and the like), C1-6 alkoxycarbonyl (such as methoxycarbonyl, ethoxycarbonyl, tert-butoxycarbonyl and the like), thiol, C1-4 alkylthio (such as methylthio, ethylthio, propylthio, butylthio and the like), amino, mono-or di-C1-4 alkylamino (such as methylamino, ethyl amino, propylamino, dimethylamino, diethylamino and the like), halogen atom (such as fluorine, chlorine, bromine, iodine and the like), trihalomethyl (such as trifluoromethyl and the like), trihalomethoxy (such as trifuloromethoxy and the like), trihalomethylthio (such as trifuloromethylthio and the like), dihalomethylthio (such as difuloromethylthio and the like), cyano, nitro and the like. One to four of these optional substituents may substitute to the replaceable position. Heterocyclic ring in "heterocyclic ring optionally with a substituent(s)" as substituent means optionally saturated or unsaturated 3-15 membered monocyclic, bicyclic or tricyclic aromatic heterocyclic ring containing 1-5 hetero atoms selected from an oxygen atom(s), a nitrogen atom(s), and/or a sulfur atom(s) and the like. 3-15 membered monocyclic, bicyclic or tricyclic aromatic heterocyclic ring containing 1-5 hetero atoms selected from an oxygen atom(s), a nitrogen atom(s), and/or a sulfur atom(s) of optionally saturated or unsaturated 3-15 membered monocyclic, bicyclic or tricyclic aromatic heterocyclic ring containing 1-5 hetero atoms selected from an oxygen atom(s), a nitrogen atom(s), and/or a sulfur atom(s) means, concretely, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine and the like. Saturated or unsaturated 3-15 membered monocyclic, bicyclic or tricyclic aromatic heterocyclic ring containing 1-5 hetero atoms selected from an oxygen atom(s), a nitrogen atom(s), and/or a sulfur atom(s) of optionally saturated or unsaturated 3-15 membered monocyclic, bicyclic or tricyclic aromatic heterocyclic ring containing 1-5 hetero atoms selected from an oxygen atom(s), a nitrogen atom(s), and/or a sulfur atom(s) means, concretely, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxatbiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane and the like. Here, substituents of heterocyclic ring have the same meaning as the above mentioned substituent in "carbocyclic ring optionally with a substituent(s)". One to four of these optional substituents may substitute to the replaceable position. Substituent in "hydroxyl optionally with a substituent(s)", "thiol optionally with a substituent(s)" and "amino optionally with a substituent(s)" as substituent means alkyl optionally with a substituent(s) (it has the same meanings as the above mentioned "alkyl optionally with a substituent(s)"), carbocyclic ring optionally with a substituent(s) (it has the same meanings as the above mentioned "carbocyclic ring optionally with a substituent(s)"), heterocyclic ring optionally with a substituent(s) (it has the same meanings as the above mentioned heterocyclic ring optionally with a substituent(s)), alkylsulfonyl (C1-4 alkylsulfonyl, such as methylsulfonyl, ethylsulfonyl and the like), heterocyclic ring sulfonyl (C6-10 heterocyclic ring sulfonyl, such as phenylsulfonyl and the like), acyl and the like. Here, acyl means (1) alkylcarbonyl optionally with a substituent(s), (2) alkenylcarbonyl alkylcarbonyl optionally with a substituent(s), (3) alkynylcarbonyl alkylcarbonyl optionally with a substituent(s), (4) carbocyclic ring carbonyl alkylcarbonyl optionally with a substituent(s), (5) heterocyclic ring carbonyl alkylcarbonyl optionally with a substituent(s) and the like. One to four out of these optional substituents may substitute to the replaceable position. Alkyl optionally with a substituent(s) in "alkylcarbonyl optionally with a substituent(s)" has the same meanings as the above mentioned "alkyl optionally with a substituent(s)". Alkenyl optionally with a substituent(s) in "alkenylcarbonyl optionally with a substituent(s)" has the same meanings as the above mentioned "alkenyl optionally with a substituent(s)". Alkynyl optionally with a substituent(s) in "alkynylcarbonyl optionally with a substituent(s)" has the same meanings as the above mentioned "alkynylcarbonyl optionally with a substituent(s)". Carbocyclic ring optionally with a substituent(s) in "carbocyclic carbonyl optionally with a substituent(s)" has the same meanings as the above mentioned "carbocyclic carbonyl optionally with a substituent(s)". Heterocyclic ring optionally with a substituent(s) in "heterocyclic ring carbonyl optionally with a substituent(s)" has the same meanings as the above mentioned "heterocyclic ring carbonyl optionally with a substituent(s)". "Carbamoyl optionally with a substituent(s)" as substituent means carbamoyl without substituent, N-mono-C1-4 alkylcarbamoyl (such as N-methylcarbamoyl, N-ethylcarbamoyl, N-propylcarbamoyl, N-isopropylcarbamoyl, N-butylcarbamoyl and the like), N,N-di-C1-4 alkylcarbamoyl (such as N,N-dimethylcarbamoyl, N,N-diethylcarbamoyl, N,N-dipropylcarbamoyl, N,N-dibutylcarbamoyl and the like), 1-piperidylcarbonyl and the like. "Sulfamoyl optionally with a substituent(s)" as substituent means sulfamoyl without substituent, N-mono-C1-4 alkylsulfamoyl (such as N-methylsulfamoyl, N-ethylsulfamoyl, N-propylsulfamoyl, N-isopropylsulfamoyl, N-butylsulfamoyl and the like), N,N-di-C1-4 alkylsulfamoyl (such as N,N-dimethylsulfamoyl, N,N-diethylsulfamoyl, N,N-dipropylsulfamoyl, N,N-dibutylsulfamoyl and the like) and the like.

In the specification, chain substituent means alkyl optionally with a substituent(s), alkenyl optionally with a substituent(s), alkynyl optionally with a substituent(s). Concretely, alkyl optionally with a substituent(s), or alkenyl optionally with a substituent(s), alkynyl optionally with a substituent(s) indicated as "substituent" in cyclic ring optionally with a substituent(s) represented by A.

In the specification, ring substituent means carbocyclic ring optionally with a substituent(s), or heterocyclic ring optionally with a substituent(s). Concretely, carbocyclic ring optionally with a substituent(s), or heterocyclic ring optionally with a substituent(s) indicated as "substituent" in cyclic ring optionally with a substituent(s) represented by A.

A is preferably a optionally saturated or unsaturated 3-15 membered monocyclic aromatic heterocyclic ring containing 1-5 hetero atoms selected from an oxygen atom(s), a nitrogen atom(s), and/or a sulfur atom(s), or optionally saturated or unsaturated 4-15 membered bicyclic or tricyclic aromatic heterocyclic ring containing 1-5 hetero atoms selected from an oxygen atom(s), a nitrogen atom(s), and/or a sulfur atom(s), more preferably pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxa diazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxaindan, benzodioxane, chroman, benzodithiolane, benzodithiane, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, tetrahydro-beta-carboline, hexahydroazepino[3,4-b]indole, 1,5,6,7,8,9-hexahydroazepino[4,3-f]indole, 1,5,6,7,8,9-hexahydropylazolo[4',3':5,6]pyrido[2,3-c]azepine, 5,6,7,8-tetrahydro-1H-pylazolo[4,3-g]isoquinoline, or 5,6,7,8-tetrahydro-1H-pylazolo[3,4-b]-1,7-naphthyridine, and most, and most preferably

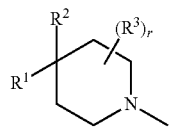

(wherein all the symbols have the same meanings as above mentioned)

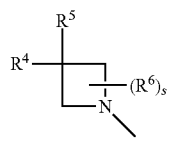

(wherein all the symbols have the same meanings as above mentioned), or

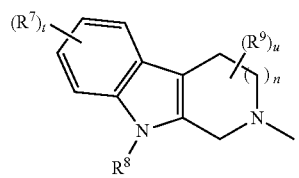

(wherein all the symbols have the same meanings as above mentioned).

B is preferably an aromatic ring, and more preferably benzene, azulene, naphthalene, phenanthrene, anthracene, pyrrole, imidazole, triazole, tetrazole, pyrazole, pyridine, pyrazine, pyrimidine, pyridazine, furan, thiophene, oxazole, isoxazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, beta-carboline, acridine, phenazine, dibenzofuran, dibenzothiophene, phenanthridine, phenanthroline, or perimidine, still more preferably benzene, pyridine, oxazole, thiophene, furan, or pyrimidine, and most preferably benzene, or pyridine.

Carbocyclic ring B is preferably a carbocyclic ring with at least 2 substituents, and more preferably

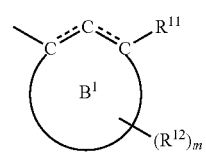

(wherein all the symbols have the same meanings as above mentioned). Additionally preferably

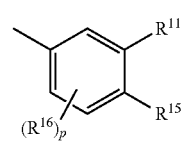

(wherein all the symbols have the same meanings as above mentioned),

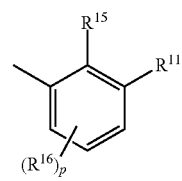

(wherein all the symbols have the same meanings as above mentioned),

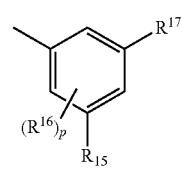

(wherein all the symbols have the same meanings as above mentioned),

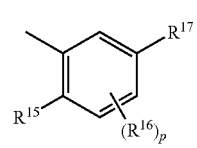

(wherein all the symbols have the same meanings as above mentioned), or

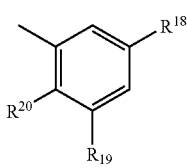

(wherein all the symbols have the same meanings as above mentioned).

Heterocyclic ring B is preferably a heterocyclic ring with at least 2 substituents, and more preferably

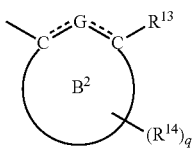

(wherein all the symbols have the same meanings as above mentioned).

X is preferably a single bond, a C1-6 alkylene optionally with a substituent(s), oxygen atom, sulfur atom, or nitrogen atom optionally with a substituent(s), more preferably a single bond, carbonyl, thiocarbonyl, oxygen atom, or nitrogen atom optionally with a substituent(s) of C1-6 alkyl, still more preferably a single bond, carbonyl, thiocarbonyl, or —NH—, and most preferably a single bond.

Y is preferably a single bond, a C1-6 alkylene optionally with substituent, oxygen atom, sulfur atom, or nitrogen atom optionally wit h a substituent(s), more preferably a sing bond, carbonyl, thiocarbonyl, oxygen atom, or nitrogen atom optionally with a substituent(s) of C1-6 alkyl, still more preferably a single bond, carbonyl, thiocarbonyl, or —NH—, and most preferably carbonyl or thiocarbonyl.

Z is preferably a single bond, a C1-6 alkylene optionally with a substituent(s), oxygen atom, sulfur atom, or nitrogen atom optionally with a substituent(s), more preferably a single bond, carbonyl, thiocarbonyl, oxygen atom, or nitrogen atom optionally with a substituent(s) of C1-6 alkyl, still more preferably a single bond, carbonyl, thiocarbonyl, or —NH—, and most preferably —NH—.

$R^1$ as substituent of A is preferably an alkyl optionally with a substituent(s), a carbocyclic ring optionally with a substituent(s), a heterocyclic ring optionally with a substituent(s), or an amino optionally with a substituent(s), more preferably an alkyl optionally with a substituent(s), or a carbocyclic ring optionally with a substituent(s), and most preferably methyl substituted by heterocyclic ring, ethoxymethyl, isopropyl, n-butyl, 3-methylbutyl, 1-ethylpropyl, 2-ethylbutyl, cyclopentylmethyl, cyclohexylmethyl, cyclopentyl, cyclohexyl, tetrahydropyranyl, phenyl, fluorophenyl, chlorophenyl, bromophenyl, toluyl, methoxyphenyl, or naphthyl.

$R^2$ is preferably hydroxyl.

$R^4$ is preferably cyclic ring optionally with a substituent(s), or an amino optionally with a substituent(s), an d more preferably heterocyclic ring optionally with a substituent(s).

$R^5$ is preferably hydrogen.

$R^8$ is preferably hydrogen, methyl, or ethyl.

$R^{11}$ is preferably alkyl optionally with a substituent(s), hydroxyl optionally with a substituent(s), amino optionally with a substituent(s), alkoxycarbonyl, cyano, or halogen atom, and more preferably trifuloromethyl, phenoxy optionally with a substituent(s), cyclohexyloxy, cyano, fluorine atom, or chlorine atom.

$R^{12}$ is preferably alkyl optionally with a substituent(s), hydroxyl optionally with a substituent(s), amino optionally with a substituent(s), alkoxycarbonyl, cyano, or halogen atom, and more preferably trifuloromethyl, phenoxy optionally with a substituent(s), cyclohexyloxy, cyano, fluorine atom, or chlorine atom.

$R^{13}$ is preferably alkyl optionally with a substituent(s), hydroxyl optionally with a substituent(s), amino optionally with a substituent(s), alkoxycarbonyl, cyano, or halogen atom, and more preferably trifuloromethyl, phenoxy optionally with a substituent(s), cyclohexyloxy, cyano, fluorine atom, or chlorine atom.

$R^{14}$ is preferably alkyl optionally with a substituent(s), hydroxyl optionally with a substituent(s), amino optionally with a substituent(s), alkoxycarbonyl, cyano, or halogen atom, and more preferably trifuloromethyl, phenoxy optionally with a substituent(s), cyclohexyloxy, cyano, fluorine atom, or chlorine atom.

$R^{15}$ is preferably alkyl optionally with a substituent(s), hydroxyl optionally with a substituent(s), amino optionally with a substituent(s), alkoxycarbonyl, cyano, or halogen atom, and more preferably trifuloromethyl, phenoxy optionally with a substituent(s), cyclohexyloxy, cyano, fluorine atom, or chlorine atom.

$R^{16}$ is preferably alkyl optionally with a substituent(s), hydroxyl optionally with a substituent(s), amino optionally with a substituent(s), alkoxycarbonyl, cyano, or halogen atom, and more preferably trifuloromethyl, phenoxy optionally with a substituent(s), cyclohexyloxy, cyano, fluorine atom, or chlorine atom.

$R^{17}$ is preferably hydroxyl optionally with a substituent(s), amino optionally with a substituent(s), alkoxycarbonyl, or cyano, and more preferably phenoxy optionally with a substituent(s), cyclohexyloxy, or cyano.

$R^{18}$ is preferably hydroxyl optionally with a substituent(s), amino optionally with a substituent(s), alkoxycarbonyl, or cyano, and more preferably phenoxy optionally with a substituent(s), cyclohexyloxy, or cyano.

$R^{19}$ is preferably hydroxyl optionally with a substituent(s), amino optionally with a substituent(s), alkoxycarbonyl, or cyano, and more preferably phenoxy optionally with a substituent(s), cyclohexyloxy, or cyano.

$R^{20}$ is preferably hydroxyl optionally with a substituent(s), amino optionally with a substituent(s), alkoxycarbonyl, or cyano, and more preferably phenoxy optionally with a substituent(s), cyclohexyloxy, or cyano.

r is preferably 0 or an integer of 1 to 2, and more preferably 0.

s is preferably 0 or an integer of 1 to 2, and more preferably 0.

t is preferably 0 or an integer of 1 to 2, and more preferably 0.

u is preferably 0 or an integer of 1 to 2, and more preferably 0.

n is preferably 1.

m is preferably 0 or an integer of 1 to 2, and more preferably 0.

G is preferably carbon atom, nitrogen atom, or oxygen atom, and more preferably carbon atom, or nitrogen atom.

p is preferably 0 or 1, and more preferably 0.

q is preferably an integer of 1 to 2, and more preferably 1.

The definition of each group in formula of a compound represented by formula (II) is described in detail in WO01/98301.

As the EDG-5 antagonist used in the present invention, whatever acts EDG-5 and inactivates EDG-5 is allowed. For example, a compound represented by formula (I) is preferably used. Concretely, all of compounds described in example is preferable. Or, the compounds preferably used in the present invention means the compounds described in WO01/98301. In particular, N-(1H-1,3,4-trimethylpyrazolo[3,4-b]pyridin-6-yl)amino-N'-(3-chlorophenyl)urea, N-(2,6-dichloro -4-pyridinyl)-2-(4-isopropyl-1,3-dimethyl-1H-pyrazolo[3,4-b]pyridin-6-yl)hydrazinecarboxamide are preferred.

As the EDG-5 agonist used in the present invention, whatever acts EDG-5 and activates EDG-5 is allowed.

In the present invention, all isomers are included unless otherwise specified. For example, alkyl, alkenyl, alkynyl, alkoxy, alkylthio, alkylene, alkenylene, alkynylene includes straight or branched one. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomer (D-, L-, d-, l-isomer), polar compounds generated by chromatographic separation (more polar compound, less polar compound), equilibrium compounds, rotational isomer, mixtures thereof at voluntary ratio and racemic mixtures are also included in the present invention.

The compounds represented by formula (I) may be converted into the pharmaceutically acceptable salts by conventional means. As pharmaceutically acceptable salts, water-soluble salts are preferred.

Pharmaceutically acceptable salts in the compound of the present invention, for example, include; salts of alkali metals (such as potassium, sodium, lithium, and the like), salts of alkaline earth metals (such as calcium, magnesium, and the like), ammonium salts (such as tetraethylammonium salts, tetrabutylammonium salts, and the like), salts of organic amines (such as triethylamine, methylamine, dimethylamine, cyclopentylamine, benzylamine, phenethylamine, piperidine, monoethanolamine, diethanolamine, tris(hydroxylmethyl)methylamine, lysine, arginine, N-methyl-D-glucamine, and the like), acid addition salts, (for example, salts of inorganic acid (such as hydrochloride, hydrobromide, hydroiodide, sulfate, phosphate, nitrate, and the like), salts of organic acid (such as acetate, trifuloroacetate, lactate, tartrate, oxalate, fumarate, maleate, benzoate, citrate, methansulfonate, ethansulfonate, benzenesulfonate, toluenesulfonate, isethionate, gulcuronate, gluconate and the like), and the like).

In the present invention, the pharmaceutically acceptable salts include solvate, or solvates of salts of alkali metals, salts of alkaline earth metals, ammonium salts, salts of organic amine, or acid addition salts in the above mentioned compounds in the present invention.

Non-toxic and water soluble solvents are preferred. Suitable solvents include, for example, hydrates, solvents of the alcohols (such as ethanol and the like) and the like.

In addition, the prodrugs of compounds represented by formula (I) mean the compounds converted into the compounds represented by formula (I) by reaction of oxygen or gastric acid within an organism. As the prodrugs of compounds represented by formula (I), when the compounds represented by formula (I) have amino, the amino of the compounds is acylated, alkylated, or phosphorylated, (such as the amino of the compounds represented by formula (I) are eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, and the like); when the compounds represented by formula (I) have hydroxyl, the hydroxyl of the compounds are acylated, alkylated, phosphorylated, borated (such as the hydroxyl of the compounds represented by formula (I) are acetylated, palmitoylated, propanoylated, pivaloylated, succinylated, fumarylated, alanylated, dimethylaminomethylcarbonylated and the like); when the compounds represented by formula (I) have carboxyl, the carboxyl of the compounds are ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, methylamidated and the like); and the like. These compounds can be manufactured by the conventional methods. In addition, the prodrugs of the compounds represented by formula (I) may be either hydrates or non-hydrates.

Processes for the Preparation of the Compound of the Present Invention:

The compound of the present invention represented by formula (I) can be prepared by the following processes, the pursuant these processes, and the processes shown in Examples. Still, ingredients may be used as salts in the following each processes for the preparation. As these salts, the salts described as pharmaceutically acceptable salts in the above mentioned formula (I) are used.

a) Among the compounds represented by formula (I), a compound wherein A is a heterocyclic ring containing nitrogen atoms, X is a single bond, Y is —CO— or —CS—, Z is a —NR$^{103}$— or a —NH—, B is a cyclic ring optionally with a substituent(s), i.e., a compound represented by formula (I-1):

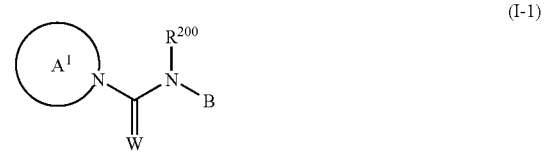

(wherein A$^1$ is a heterocyclic ring containing nitrogen(s); W is oxygen or sulfur; R$^{200}$ is hydrogen; or R$^{103}$ and other symbols have the same meanings as the above mentioned.) can be prepared by the following processes.

A compound represented by formula (I-1) can be prepared by subjecting to a reaction a compound represented by formula (III);

(wherein A$^{I-1}$ has the same meanings as A$^1$, and carboxyl, hydroxyl, amino, or thiol comprising the groups represented by A$^{I-1}$, if necessary, are protected with a protecting group.) with a compound represented by formula (IV);

(wherein L is a leaving group (such as halogen or imidazolyl and the like.), B$^1$ and R$^{200-1}$ have the same meanings as B and $R^{200}$, and carboxyl, hydroxyl, amino, or thiol containing the groups represented by $B^1$ and $R^{200-1}$, if necessary, are protected with a protecting group. Other symbols have the same meanings as the above mentioned.), followed by optionally a deprotection reaction.

A reaction of a compound represented by formula (III) with a compound represented by formula (IV) is carried out by the following processes. For example, a compound represented by formula (III) is reacted with a compound represented by formula (IV) in an organic solvent (such as chloroform, dichloromethane, diethylether, tetrahydrofuran and the like) in the presence of a base (such as pyridine, triethylamine, dimethylaniline, dimethylaminopyridine, diisopropylethylamine and the like) at a temperature of 0° C. to reflux temperature.

In addition, a compound represented by formula (III) is reacted with a compound represented by formula (IV) in an organic solvent (such as dioxane, tetrahydorfuran, diethylether and the like) using an aqueous alkaline solution (such as aqueous sodium bicarbonate solution or sodium hydroxide solution and the like) at a temperature of 0° C. to reflux temperature.

The deprotection reaction of a protective group for carboxyl, hydroxyl, amino, or thiol is known, and it includes;
(1) alkaline hydrolysis,
(2) deprotection reaction under acidic conditions,
(3) deprotection reaction by hydrogenolysis,
(4) deprotection reaction of a silyl group,
(5) deprotection reaction using metals,
(6) deprotection reaction using metal complexes, and the like.

These methods are described concretely as follows.
(1) The deprotection reaction by alkaline hydrolysis is, for example, carried out in an organic solvent (such as methanol, tetrahydrofuran, or dioxane and the like) using a hydroxide of an alkali metal (such as sodium hydroxide, potassium hydroxide, or lithium hydroxide, and the like), a hydroxide alkaline earth metal (such as barium hydroxide, or calcium hydroxide and the like), a carbonate (such as sodium carbonate or potassium carbonate, and the like), an aqueous solution thereof, or a mixture thereof at a temperature of 0 to 40° C.
(2) The deprotection reaction under acidic conditions is carried out, for example, in an organic solvent (such as dichloromethane, chloroform, dioxane, ethyl acetate, or anisole and the like) in the presence or absence of 2,2,2-trifluoroethanol in an organic acid (such as acetic acid, trifuluoroacetic acid, methanesulfonic acid, or p-tosylate, and the like), an inorganic acid (such as hydrochloric acid, or sulfuric acid, and the like) or a mixture thereof (such as hydrogen bromide/acetic acid, and the like) at a temperature of 0 to 100° C.
(3) The deprotection reaction by hydrogenolysis is carried out, for example, in a solvent (such as ethers (such as tetrahydrofuran, dioxane, dimethoxyethane, or diethylether, and the like), alcohols (such as methanol, or ethanol, and the like), benzenes (such as benzene, or toluene and the like), ketones (such as acetone, or methyl ethyl ketone, and the like), nitrites (such as actetonitrile and the like), amides (such as dimethylformamide and the like), water, ethyl acetate, acetic acid, or a mixed solvent of at least two of these and the like) in the presence of a catalyst (such as palladium-carbon, palladium black, palladium hydroxide-carbon, platinum oxide, or Raney nickel, and the like) under the hydrogenosphere at normal pressure or under pressurization, or in the presence of ammonium formate at a temperature of 0 to 200° C.

(4) The deprotection reaction of a silyl group is carried out, for example, in a water-miscible organic solvent (such as tetrahydrofuran, or acetonitrile, and the like) using tetrabutylammonium fluoride at a temperature of 0 to 40° C.
(5) The deprotection reaction using metals is carried out, for example, in an acidic solvent (acetic acid, pH4.2-7.2 buffer solution, or a mixture of a solution thereof and an organic solvent of tetrahydrofran and the like) in the presence of zinc powder, if necessary sonicating, at the temperature of 0 to 40° C.
(6) The deprotection reaction using metal complexes is carried out, for example, in an organic solvent (such as dichloromethane, dimethylformamide, tetrahydrofran, ethyl acetate, acetonitrile, dioxane, ethanol and the like), water, or a mixture thereof in the presence of a trap reagent (such as tributyltine hydride, triethylsilane, dimedone, morpholine, diethylamine, pyrrolidine, and the like), an organic acid (acetic acid, formic acid, 2-ethyl hexanoic acid, and the like) and/or salts of organic acid (such as sodium 2-ethylhexanoate, potassium 2-ethylhexanoate and the like), in the presence or absence of a phosphine reagent (such as triphenylphosphine and the like), using metal complexes (such as tetrakistriphenylphosphinepalladium(0), dichlorobis(triphenylphosphine)palladium(II), palladium acetate(II), tris(triphenylphosphine)rhodium(II) chloride and the like) at the temperature of 0 to 40° C.

In addition, the deprotection reaction except the above mentioned processes can be carried out, for example, by the process described in T. W. Greene, Protective Groups in Organic Synthesis, Wiley, N.Y., 1999.

The protection group for carboxyl includes methyl, ethyl, allyl, t-butyl, trichloroethyl, benzyl (Bn), phenacyl, p-methoxybenzyl, trytyl, 2-chlorotrytyl, or a solid phase carrier bound of a structure thereof and the like.

The protection group for hydroxyl includes methyl, ethyl, methoxymethyl (MOM), 1-ethoxymethyl (EE), methoxyethoxymethyl (MEM), 2-tetrahydropyranyl(THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), 2,2,2-trichloroethoxycarbonyl (Troc), and the like.

The protection group of amino includes benzyloxycarbonyl, t-butoxycarbonyl, allyloxycarbonyl (Alloc), 1-methyl-1-(4-biphenyl) ethoxycarbonyl (Bpoc), trifluoroacetyl, 9-fluorenylmethoxycarbonyl, benzyl (Bn), p-methoxybenzyl, benzyloxymethyl (BOM), 2-(trimethylsilyl) ethoxymethyl (SEM) and the like.

The protection group of thiol includes benzyl, methoxybenzyl, methoxymethyl (MOM), 2-tetrahydropyranyl (THP), diphenylmethyl, acetyl (Ac) and the like.

The protective group for carboxyl, hydroxyl, amino or thiol is not particularly limited to the above mentioned groups, so long as it can be easily and selectively left. For example, those described in T. W. Greene, Protective Groups in Organic Synthesis, Wiley, N.Y., 1999 can be used.

As is easily understood by those skilled in the art, an object compound of the present invention can be produced easily by using a different deprotection reaction depending on usage.

The compound represented by formula (I-1) can also be produced by subjecting a compound represented by formula (V):

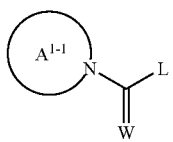

(wherein all the symbols have the same meanings as the above mentioned) and a compound represented by formula (VI):

(wherein all the symbols have the same meanings as the above mentioned) to a reaction, followed by deprotection reaction of a protective group, if necessary.

A reaction of a compound represented by formula (V) with a compound represented by formula (VI) is carried out by the following process. For example, a compound represented by formula (V) is reacted with a compound represented by formula (VI) in the presence of a base (such as pyridine, triethylamine, dimethylaniline, dimethylaminopyridine, diisopropylethylamine and the like) in an organic solvent (such as chloroform, dichloromethane, diethylether, tetrahydorfuran and the like) at the temperature of 0° C. to reflux temperature.

Or, a compound represented by formula (V) can be reacted with a compound represented by formula (VI) in an organic solvent (such as dioxane, tetrahydrofuran, diethylether and the like) using an aqueous alkaline solution (such as aqueous sodium bicarbonate solution or sodium hydroxide solution and the like) at the temperature of 0° C. to reflux temperature.

The deprotection reaction of a protective group can be carried out in the same manner as the above mentioned.

The compound represented by formula (I-1) can also be produced by subjecting a compound represented by formula (III), a compound represented by formula (VI) and a compound represented by formula (VII):

(wherein all the symbols have the same meanings as the above mentioned) to a reaction, followed by deprotection reaction of a protective group, if necessary.

A reaction of a compound represented by formula (III), a compound represented by formula (VI) with a compound represented by formula (VII) is carried out, for example, in an organic solvent (such as ethyl acetate, chloroform, dichloromethane, diethylether, tetrahydrofuran, benzene, toluene and the like), or without a solvent, in the presence of a compound represented by formula (III), a compound represented by formula (VI) and a compound represented by formula (VII) (such as a phosgene compound (such as phosgene, thiophosgene, triphosgene (bis(trichloromethyl) carbonate) and the like), a imidazole compound (such as CDI (carbonyldiimidazole), TCDI (thiocarbonyldiimidazole) and the like) and a base (such as pyridine, triethylamine, dimethylaniline, dimethylaminopyridine, diisopropylethylamine and the like) at the temperature of −20° C. to reflux temperature.

This reaction is preferred to be carried out in the presence of an inert gas under the condition of anhydrous.

The deprotection reaction of a protective group can be carried out in the same manner as the above mentioned.

b) Among the compounds represented by formula (I), a compound wherein A is a heterocyclic ring containing nitrogen atom(s), X is a single bond, Y is a —CO— or —CS—, Z is a —NH—, B is a cyclic group optionally with a substituent(s), i.e., a compound represented by formula (I-2);

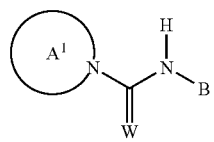

(wherein all the symbols have the same meanings as the above mentioned.) can also be produced by subjecting a compound represented by formula (III) and a compound represented by formula (VIII);

to a reaction, followed by deprotection reaction of a protective group, if necessary.

A reaction of a compound represented by formula (III) with a compound represented by formula (VIII) can be carried out in an organic solvent (such as toluene, benzene, xylene, tetrahydrofuran, methylene chloride, diethylether, 1,2-dichloroethane and the like) at the temperature of 0° C. to reflux temperature.

This reaction is preferred to be carried out in the presence of an inert gas under the condition of anhydrous.

The deprotection reaction of a protective group can be carried out in the same manner as the above mentioned.

c) Among the compounds represented by formula (I), a compound wherein A is a heterocyclic ring containing nitrogen atom(s), X is a single bond, Y is —CO— or —CS—, Z is methylene optionally with one or two substituent(s), B is a cyclic group optionally with a substituent(s), i.e., a compound represented by formula (I-3);

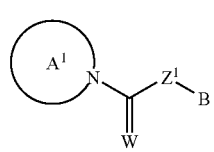

(wherein $Z^1$ is —$CH_2$—, —$CHR^{101}$—, or —$CR^{101}R^{102}$—, other symbols have the same meanings as the above mentioned) can also be produced by subjecting a compound represented by formula (III) and a compound represented by formula (IX);

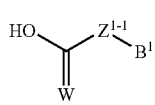

(wherein $Z^{1-1}$ has the same meanings as $Z^1$ and a group represented by $Z^{1-1}$ containing carboxyl, hydroxyl, amino or thiol shall be protected, if necessary. Other symbols have the same meanings as the above mentioned.) to a reaction, followed by deprotection reaction of a protective group, if necessary.

The reaction of a compound represented by formula (III) with a compound represented by formula (IX) includes, for example,
(1) a method using an acid halide,
(2) a method using a mixed acid anhydride
(3) a method using a condensing agent and the like.

These methods are described specifically as follows.
(1) The method using an acid halide is carried out, for example, by reacting a compound represented by formula (IX) in an organic solvent (such as chloroform, dichloromethane, diethylether, tetrahydrofuran, dimethoxyethane and the like) or a without a solvent, with an acid halogenation (such as oxalyl chloride, thionyl chloride and the like) at a temperature of −20° C. to the reflux temperature, and by reacting the obtained acid halide in the presence of a base (such as pyridine, triethylamine, dimethylaniline, dimethylaminopyridine, diisopropylethylamine and the like) with a compound represented by formula (III) in an organic solvent (such as chloroform, dichloromethane, diethylether, tetrahydrofuran, acetonitrile, ethyl acetate and the like) at a temperature 0 to 40° C. Further, this method can also be carried out by reacting the obtained acid in an organic solvent (such as dioxane, tetrahydrofuran, dichloromethane and the like) in the presence or in the absence of a phase-transfer catalyst (quaternary ammonium salts and the like, such as tetrabutylammonium chloride, triethylbenzylammonium chloride, tri n-octylmethylammonium chloride, trimethyldecylammonium chloride, tetramethylammonium bromide and the like) using an aqueous alkaline solution (aqueous sodium bicarbonate solution, sodium hydroxide solution and the like) with a compound represented by formula (III) at a temperature of 0 to 40° C.
(2) The method using a mixed acid anhydride is carried out, for example, by reacting a compound represented by formula (IX) in an organic solvent (such as chloroform, dichloromethane, diethylether, tetrahydrofuran and the like) or without a solvent in the presence of a base (such as pyridine, triethylamine, dimethylaniline, dimethylaminopyridine, diisopropylethylamine and the like) with an acid halide (such as pivaloyl chloride, tosyl chloride, mesyl chloride and the like) or an acid derivative (such as ethyl chloroformate, isobutyl chloroformate and the like) with a compound represented by formula (III) at a temperature of 0 to 40° C.
(3) The method using a condensing agent is carried out, for example, by reacting a compound represented by formula (IX) and a compound represented by formula (III) in an organic solvent (chloroform, dichloromethane, dimethylformamide, diethylether, tetrahydrofuran and the like) or without a solvent in the presence or in the absence of a base (such as pyridine, triethylamine, dimethylaniline, dimethylaminopyridine, and the like) using a condensing agent (1,3-dicyclohexylcarbodiimide (DCC)), 1-ethyl-3-[3-(dimethylamino)propyl]carbodiimide (EDC), 1,1'-carbonyldiimidazole (CDI), 2-chloro-1-methylpyridinium iodine, 1-propyl-phosphonic acid cyclic anhydride (PPA), and the like) with or without 1-hydroxylbenoztriazole (HOBt) at a temperature of 0 to 40° C.

These (1), (2) and (3) reactions are preferably carried out under the inactive gas (such as argon, nitrogen, and the like) atmosphere and anhydrous conditions.

The deprotection reaction of a protective group can be carried out in the same manner as the above mentioned.

The compounds represented by formula (III), (IV), (V), (VI), (VII), (VIII) and (IX) are known per se or can be easily produced by known methods, for example, those described in Richard C. Larock, Comprehensive Organic Transformations: A Guide to Functional Group Preparations.

Among the compounds represented by formula (I), the compounds except the above mentioned can be produced by using examples described in the present specification, or by using known methods, for example, the combined methods described in Richard C. Larock, Comprehensive Organic Transformations: A Guide to Functional Group Preparations.

In each reaction in the present specification, as it is clear for those skilled in the art, a reaction under heating can be carried out using water bath, oil bath, sand bath, or microwave.

In each reaction in the present specification, a reaction may be carried out by using a solid-phase supported reagent supported in the high polymer (such as polystyrene, polyacrylamide, polypropylene, polyethylene glycol and the like).

In each reaction in the present specification, a reaction product can be purified by a general purification method, for example, distillation under normal or reduced pressure, high speed liquid chromatography using silica gel or magnesium silicate, thin layer chromatography, ion exchange resin, scavenger resin or column chromatography, washing, re-crystallization or the like. Purification may be carried out at each reaction or after completion of several reactions.

A reaction represented by formula (II) can be produced by the method described in WO01/98301.

EDG-5 modulator is useful for a therapeutic and/or prevention agent for a disease due to constriction or vasodilation of blood vessels. For more detail, EDG-5 antagonist among EDG-5 modulator is useful for a therapeutic and/or prevention agent for a disease due to constriction of blood vessels, for example, cerebrovascular spasmodic disorder after subarachnoid hemorrhage or stroke, cardiovasucular spasmodic disorder, hypertension, renal disease, cardiac infarction, cardiac angina, arrhythmia, facilitation of the portal blood pressure involved in liver cirrhosis, varicosity involved in liver cirrhosis and the like. Further, EDG-5 agonist is useful for a therapeutic and/or prevention agent for a disease due to vasodilation of blood vessels, for example, chronic headache (such as migraine, tension-type headache, mixed-type headache thereof, or migrainous neuralgia), haemorrhoid, congestive disorder and the like. In addition, hypertension includes, for example, cardiac failure, hypertension involved in complication of diabetes, nephropathy or the like, secondary hypertension and the like.

[Toxicity]

Toxicity of the compound used in the present invention is low, and it was confirmed to be safe enough for use as a pharmaceutical agent.

Industrial Availability

[Application for Pharmaceuticals]

The EDG-5 modulator used in the present invention binds specifically to EDG-5 and indicates antagonist or agonist action, therefore it is expected to be useful in the treatment and/or prevention of a disease due to constriction or vasodilation of blood vessels caused through EDG-5 by S1P. In particular, EDG-5 antagonist is useful for a therapeutic and/or prevention agent for a disease due to constriction of blood vessels, for example, cerebrovascular spasmodic disorder after subarachnoid hemorrhage or stroke, cardiovasucular spasmodic disorder, hypertension, renal disease, cardiac infarction, cardiac angina, arrhythmia, facilitation of the portal blood pressure involved in liver cirrhosis, varicosity involved in liver cirrhosis and the like. Further, EDG-5 agonist is useful for a therapeutic and/or prevention agent for a disease due to vasodilation of blood vessels, for example, chronic headache (such as migraine, tension-type headache, mixed-type headache thereof, or migrainous neuralgia), haemorrhoid, congestive disorder and the like. In addition, hypertension includes, for example, cardiac failure, hypertension involved in complication of diabetes, nephropathy or the like, secondary hypertension and the like.

Or, EDG-5 antagonist is useful in the treatment and/or prevention for except a disease due to constriction of blood vessels, for example, lung fibrosis, hepatic fibrosis, renal fibrosis, asthma, nephropathy, diabetes, hyperlipemia or t he like.

To use EDG-5 modulator, or the combination drug with EDG-5 modulator and the other drug for the purpose of the above mentioned, it is normally administered to the entire or local part of human body orally or parenterally.

Further, in the present invention, EDG-5 modulator may be administered in combination with other drugs for the purpose of;
(1) complement and/or enhancement of preventing and/or treating effect of the compound,
(2) improvement of dynamics and absorption of the compound, and lowering of dose, and/or
(3) alleviation of side effect of the compound.

The combination drug with EDG-5 modulator and the other drug may be administered in combination with other drugs as a composition in one drug product comprising these components, or may be administered separately. When they are administered independently, they may be administered simultaneously or with time lag. Administering with time lag includes the method of administering the EDG-5 antagonist before other drugs and vice versa; they may be administered in the same route or not.

The above combination drugs take effect on whichever disease preventing and/or treatment effect of EDG-5 modulator is complemented and/or enhanced.

Other agents to compensating and/or enhancing the preventive and/or treatment effect of the EDG-5 modulator on hypertension include a calcium antagonist, an angiotensin II antagonist, an angiotensin converting enzyme inhibitor, a diuretic, a phosphodiesterase 4 inhibitor, prostaglandins (hereinafter referred as "PG"), an aldosterone antagonist or the like.

Other agents to compensating and/or enhancing the preventive and/or treatment effect of the EDG-5 modulator on renal disease include a steroid, a phospodiesterase 4 inhibitor, a non-steroidal anti-inflammatory drug, a thromboxane synthetase inhibitor, a leukotoriene receptor antagonist, an angiotensin II antagonist, an angiotensin converting enzyme inhibitor, a diuretic, PGs or the like.

Other agents to compensating and/or enhancing the preventive and/or treatment effect of the EDG-5 modulator on cerebrovascular spasmodic disorder, cardiovasucular spasmodic disorder or the like after subarachnoid hemorrhage or stroke include a calcium antagonist, a thrombolytic agent, a leukotoriene receptor antagonist, an endthelin antagonist, an antioxidant substance, a radical scavenger, a PARP inhibitor, an astrocyte functional improvement agent, a vasodilator or the like.

Other agents to compensating and/or enhancing the preventive and/or treatment effect of the EDG-5 modulator on migraine include a non-steroidal anti-inflammatory drug, an ergotamine preparation, a calcium antagonist, a serotonin agonist or the like.

Other agents to compensating and/or enhancing the preventive and/or treatment effect of the EDG-5 modulator on fibrosis include a steroid, a retinoid, a pirfenidone or the like.

The calcium antagonist includes nifedipine, benidipine hydrochloride, diltiazem hydrochloride, verapamil hydrochloride, nisoldipine, nitrendipine, bepridil hydrochloride, amlodipine besilate, lomerizine hydrochloride and the like.

The angiotensin II antagonist includes losartan, candesartan, valsartan, irbesartan, olmesartan, telmesartan and the like.

The angiotensin converting enzyme inhibitor includes alacepril, imidapril hydrochloride, quinapril hydrochloride, temocapril hydrochloride, delapril hydrochloride, benazepril hydrochloride, captoril, trandolapril, perindopril erubumine, enalapril maleate, lisinopril and the like.

The diuretic drug includes mannitol, furosemide, acetazolamide, diclofenamide, methazolamide, trichlormethiazide, mefruside, spironolactone, aminophylline and the like.

The phospodiesterase 4 inhibitor includes rolipram, cilomilast, Bay19-8004, NIK-616, roflumilast (BY-217), cipamfylline (BRL-61063), atizoram (CP-80633), SCH-351591, YM-976, V-11294A, PD-168787, D-4396, IC-485 and the like.

The PGs include a PG receptor agonist, a PG receptor antagonist and the like.

The PG receptor includes a PGE receptor (EP1, EP2, EP3, EP4), a PGD receptor (DP, CRTH2), a PGF receptor (FP), a PGI recptor (IP), a TX recptor (TP) and the like.

The aldosterone antagonist includes drospirenon, metyrapone, potassium canrenoate, canrenone, eplerenone, ZK-91857 and the like.

The thromboxane synthetase inhibitor includes ozagrel hydrochloride, imitrodast sodium and the like.

The thrombolytic agent includes alteplase, urokinase, tisokinase, nasaruplase, tissue plasminogen activator, pamiteplase, monteplase and the like.

The steroid includes as an internal medicine or an injectable solution, for example, cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone and the like.

The non-steroidal anti-inflammatory drug includes sasapyrine, sodium salicylic acid, aspirin, aspirin dialminate combinations, diflunisal, indomethacin, suprofen, ufenamate, dimethyl-isopropyl-azulene, bufexamac, felbinac, diclofenac, tolmetin sodium, clinoril, fenbufen, napumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranopofen, loxoprofen sodium, alminoprofen, zaltoprofen, mefenamic acid, aluminum mefenamic acid, tolfenamic acid, floctafenine, ketophenylbutazone, oxyphenbutazone, pyroxicam, tenoxicam, ampiroxicam, Napageln ointment, epirizole, tiaramide hydroclorid e, tinoridine hydrochloride, emorfazone, sulpyrine, migrenin, Saridon, Sedes G, Amipylo N, sorbone, pilin derivatives for cough and cold preparations, acetaminophene, phenacetin, dimetotiazine mesilate, simetride combinations, non-pilin derivatives for cough and cold preparations and the like.

The ergotamine preparation includes dihydroergotamine mesilate, ergotamine tartrate and the like.

The serotonin agonist includes sumatriptan, zolmitriptan, naratriptan, rizatriptan, eletriptan, almotriptan, frovatriptan and the like.

The radical scavenger includes radicut.

The astrocyte functional improvement agete includes ONO-2506.

The weight proportion of the EDG-5 modulator and other drugs is not particularly limited.

Arbitrary two or more of other drugs may be administered in combination.

Further, the other drugs to compemsating and/or enhancing the preventive and/or treatment effect of the EDG-5 modulator include not only those which have so far been found but also those which will be found on the basis of the above mentioned mechanism.

To use EDG-5 modulator, or the combination drug with EDG-5 modulator and the other drug for the purpose of the above mentioned, it is normally administered to the entire or local part of human body orally or parenterally.

The dose of the EDG-5 modulator depends on the age, weight and symptom of the patient, the remedial value, the administration method, the treatment time and the like. In practice, however, EDG-5 modulator is administered orally once or several times per day each in an amount of from 100μg to 1000 mg per adult, parenterally once or several times pre day each in an amount of from 50 μg to 50 mg pre adult or continuously administered into vein for 1 hour to 24 hours per day.

It goes without saying that the dose of EDG-5 modulator may be less than the above mentioned value or need to exceed the above mentioned range because the dose varies under various conditions as mentioned above.

The EDG-5 modulator, or the combination drug with EDG-5 modulator and the other drug may be administered in the composition of, for example, solid compositions or liquid compositions each for oral administration, or injections, compositions for external use, suppositories, ophthalmic solutions, inhalers and the like.

Solid compositions for oral administration include compressed tablets, pills, capsules, powders and granules. Capsules include hard capsules and soft capsules.

In such solid compositions, one or more of the active substance(s) is/are used as is, or used to be prepared by the law of the art mixed with, for example, diluents (such as lactose, mannitol, glucose, microcrystalline cellulose, starch and the like), binder (such as hydroxypropyl cellulose, polyvinyl pyrrolidone, magnesium metasilicate aluminate and the like), disintegrating agents (such as cellulose calcium glycolate and the like), lubricating agents (such as magnesium stearate and the like), stabilizers, assisting agents for dissolving (such as glutamic acid, asparatic acid and the like). The tablets or pills may, if necessary, be coated with coating agents (such as sugar, gelatin, hydroxypropyl cellulose, hydroxypropyl cellulose phthalate and the like), or be coated with two or more films. Furthermore, capsules of absorbable materials such as gelatin are included Liquid compositions for oral administration include pharmaceutically acceptable emulsions, solutions, syrups and elixirs. In such compositions, one or more active compound(s) is/are dissolved, suspended or emulsified in an inert diluent commonly used (e.g., purified water, ethanol and mixed solution thereof). Furthermore, such liquid compositions may also contain wetting agents or suspending agents, emulsifying agent S, sweetening agents, flavoring agents, perfuming agents, buffering agents and preserving agents.

The formulations of external use for parental administration include, for example, ointments, gel agents, cream agents, poultices, adhesive agents, liniments, air spray agents, inhalers, spray agents, airzol agents, ophthalmic solutions, collnariums and the like. These include one or more active compound(s) and are prepared by known methods or by prescription normally used.

The ointments are prepared by known methods or by prescription normally used. For example, one or more of the active substance(s) may be mixed, or dissolved in the base and prepared. The ointment bases are selected from those which are known or are normally used. They are used only or mixed two or more those which are selected from, for example, higher fatty acid or higher fatty acid ester (such as adipic acid, myristic acid, palmitic acid, stearic acid, oleic acid, adipic ester, myristic ester, palmitic ester, stearic ester, ollec ester and the like), waxes (such as, bees wax, whale wax, ceresin and the like), surfactant (such as polyoxyethylenealkylether phosphate and the like), higher alcohol (such as cetanol, stearyl alcohol, cetostearyl alcohol and the like), silicon oil (such as dimethylpolysiloxane and the like), hydrocarbons (such as hydrophilic vaseline, white vaseline, purified lanoline, petrolatum and the like), glycols (such as ethylene glycol, diethylene glycol, propylene glycol, polyethylene glycol, macrogol and the like), vegetable oil (such as castor oil, olive oil, sesame oil, turpentine and the like), animal oil (such as mink oil, yolk oil, squalane, squalene and the like), water, absorption promoter, irritation inhibitor and the like. Further, they may include humectant, preservative, stabilizer, antioxidant substance, flavoring agent and the like.

The gels are prepared by known methods or by prescription normally used. For example, one or more of the active substance(s) may be dissolved in the base and prepared. The gel bases are selected from those which are known or are normally used. They are used only or mixed two or more those which are selected from, for example, lower alcohol (such as ethanol, isopropylalcohol and the like), gelatinizing agent (such as carboxymethyl cellulose, hydroxyethyl cellulose, hydroxypropyl cellulose, ethyl cellulose and the like), neutralizing agent (such as triethanolamine, diisopropanolamine and the like), surfactant (such as polyoxyethylenealkylether phosphate and the like), gums, water, absorption promoter, irritation inhibitor and the like. Further, they may include preservative, antioxidant substance, flavoring agent and the like.

The cream agents are prepared by known methods or by prescription normally used. For example, one or more of the active substance(s) may be dissolved or emulsified in the base and prepared. The cream agent bases are selected from those which are known or are normally used. They are used only or mixed two or more those which are selected from, for example, higher fatty acid ester, lower alcohol, hydrocarbons, polyhydric alcohol (such as propylene glycol, 1,3-butylene glycol and the like), higher alcohol (such as 2-hexyldecanol, cetanol and the like), emulsifying agent (such as polyoxyethylene alkyl ethers, fatty acid esters and the like), water, absorption promoter, irritation inhibitor and the like. Further, they may include preservative, antioxidant substance, flavoring agent and the like.

The poultices are prepared by known methods or by prescription normally used. For example, one or more of the active substance(s) may be dissolved in the base to be pastes, flatted and coated on the supports, and prepared. The poultices bases are selected from those which are known or are normally used. They are used only or mixed two or more those which are selected from, for example, thickener (such as polyacrylic acid, polyvinyl pyrrolidone, gum arabic, starch, gelatin, methyl cellulose and the like), humectant (such as urea, glycerin, propylene glycol and the like), filler (such as kaolin, zinc oxide, talc, calcium, magnesium and the like), water, solubilizing agent, adhesive, irritation inhibitor and the like. Further, they may include preservative, antioxidant substance, flavoring agent and the like.

The adhesive agents are prepared by known methods or by prescription normally used. For example, one or more of the active substance(s) may be dissolved in the base to be pastes, flatted and coated on the supports, and prepared. The bases for adhesive agents are selected from those which are known or are normally used. They are used only or mixed two or more those which are selected from, for example, polymer base, fat, higher fatty acid, adhesive, irritation inhibitor and the like. Further, they may include preservative, antioxidant substance, flavoring agent and the like.

The liniments are prepared by known methods or by prescription normally used. For example, one or more of the active substance(s) may be dissolved, suspended or emulsified in only or mixed two or more those which are selected from water, alcohol (ethanol, polyethylene glycol and the like), higher fatty acid, glycerin, soap, emulsifying agent, suspending agent and the like, and prepared.

The air spray agents, inhalers, or spray agents may comprise in addition to a generally used diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355.

Injection for parental administration includes solid injection used to be dissolved or suspended into the solutions, suspensions, emulsions, or needed fluxing materials. For injection, one or more of the active substance(s) may be dissolved, suspended or emulsified in the fluxing materials and used. The fluxing materials use, for example, distilled water for injection, physiological salt solution, vegetable oil, propylene glycol, polyethylene glycol, alcohols (such as ethanol and the like) and combinations thereof. Further such injections may include stabilizer, solubilizing agent (such as glutamic acid, aspartic acid, POLYSORBATE80 (registered trade mark) and the like), suspending agent, emulsifying agent, soothing agent, buffering agent, preservative and the like. These are prepared by sterilizing or aseptic manipulation on the final process. Further, these sterilized solid formulations, for example, freeze -dried products are prepared, and these can also be used by dissolve to the asepticized or sterile distilled water for injection, or other solvents before use.

The ophthalmic solutions for parental administration include eye drop, suspended eye drop, emulsified eye drop, in time dissolved eye drop, or eye ointment and the like.

These ophthalmic solutions are prepared according to known methods. For example, one or more of the active substance(s) may be dissolved, suspended or emulsified in the fluxing materials and used. The fluxing materials for ophthalmic solution include sterile purified water, physiological salt solution, the other aqueous fluxing materials, non-aqueous fluxing materials for injection (such as vegetable oil and the like) and the like, and the combinations thereof. The ophthalmic solutions may include those which are accordingly selected from isotonic agent (such as sodium chloride, concentrated glycerin and the like), buffering agent (such as sodium phosphate, sodium acetate and the like), surfactant (such as POLYSORBATE80 (registered trade mark), polyoxyl stearate 40, polyoxyethylene hardening castor oil and the like), stabilizing agent (such as sodium citrate, edentate sodium and the like), antiseptic agent (such as benzalkonium chloride, paraben and the like) and the like. These are prepared by sterilizing or aseptic manipulation on the final process. Further, these sterilized solid formulations, for example, freeze-dried products are prepared, and these can also be used by dissolve to the asepticized or sterile distilled water for injection, or other fluxing materials before use.

The inhalers for parental administration include aerosol agent, powder medicine for inhalation or liquid medicine for inhalation. Such inhalers may be used to be accordingly dissolved or suspended to water or other suitable vehicle.

These inhalers are prepared according to known methods.

The liquid medicines for inhalation are prepared to be accordingly selected from, for example, antiseptic agent (such as benzalkonium chloride, paraben and the like), coloring agent, buffering agent (such as sodium phosphate, sodium acetate and the like), isotonic agent (such as sodium chloride, concentrated glycerin and the like), thickener (such as carboxyvinyl polymer and the like), absorption promoter and the like.

The powder medicines for inhalation are prepared to be accordingly selected from, for example, lubricating agent (such as stearic acid and salt thereof and the like), binding agent (such as starch, dextrin and the like), coloring agent, antiseptic agent (such as benzalkonium chloride, paraben and the like), absorption promoter and the like.

The normal fogger (atomizer, nebulizer) is used in the administration of the liquid medicines for inhalation, and the inhaler for powder medicines is used in the administration of powder medicines for inhalation.

The other compositions for parental administration include suppositories for rectal administration and pessaries for vaginal administration and the like which comprise one or more of the active substance(s) and ma be prepared by methods known per se.

BEST MODE FOR CARRYING OUT THE INVENTION

Figure 1:
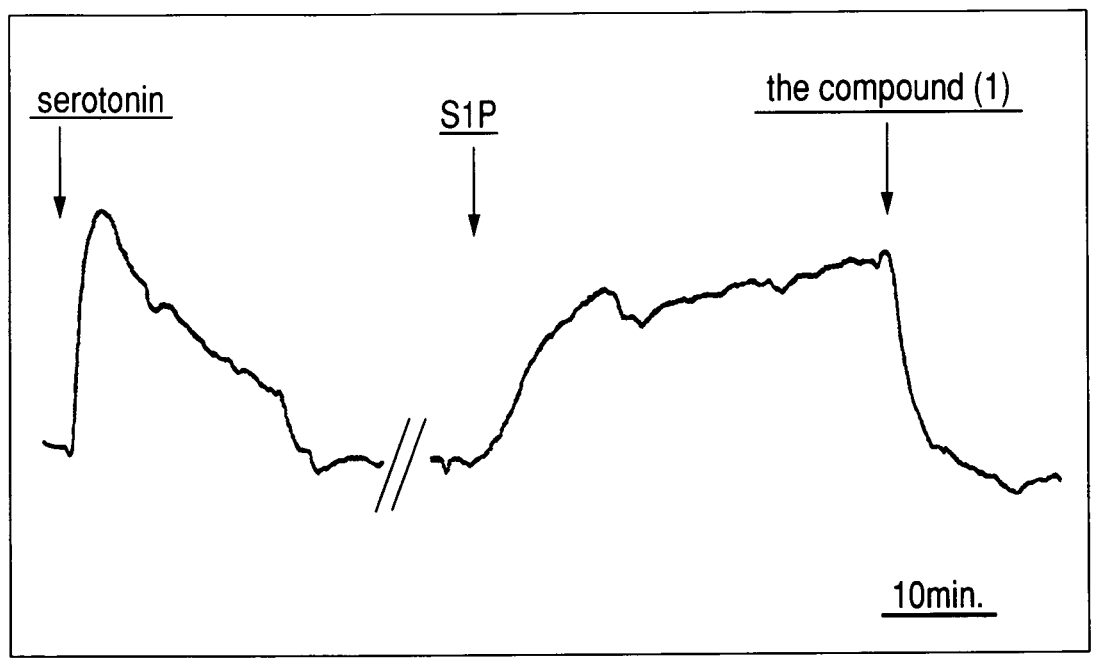
FIG. 1 is a graph showing the suppression of vasoconstrictor action of canine removed basilar artery by S1P by 10 μM of the compound (1) of the present invention.

The present invention is explained below in detail base on Reference Examples, Examples and Biological Examples, however, the present invention is not limited thereto.

The solvents in the parentheses show the developing or eluting solvents and the ratios of the solvents used are by volume in chromatographic separations or TLC. The solvents in the parentheses in NMR show the solvents for measurement.

In addition, HPLC condition shows as follows.
In addition, HPLC condition shows as follows
Used equipment: Waters LC/MS
Column: Xterra (Registered trade mark) MS $C_{18}$ 5 um, 4.6×50 mm I.D.
Flow rate: 3 mL/min
Eluting solvent: A solvent: 0.1% trifuloroacetic acid aqueous solution
B solvent: 0.1% trifuloroacetic acid-acetonitrile solution
The time course of mixed ratio of eluting solvent shows as follows;

| time(min) | A solvent | B solvent |
| --- | --- | --- |
| 0 | 95 | 5 |
| 0.5 | 95 | 5 |
| 3 | 0 | 100 |
| 3.5 | 0 | 100 |
| 3.51 | 95 | 5 |
| 5 | 95 | 5 |

Further, the compound names showed in Reference Examples and Examples are named by ACD/Name (version 6.00, manufactured by Advanced Chemistry Development Inc.).

REFERENCE EXAMPLE 1

Ethyl 4-butyl-4-hydroxy-1-piperidinecarboxylate

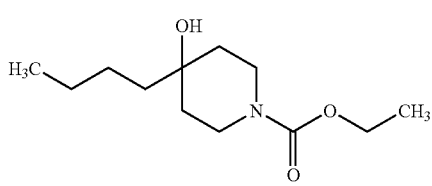 [SMILES: CCCCC1(O)CCN(C(=O)OCC)CC1]

Under an atmosphere of argon, to a solution of ethyl 4-oxo-1-piperidinecarboxylate (1.00 g) in anhydrous tetrahydrofuran (5 mL) was added n-butyl lithium (1.56M hexane solution, 5.62 mL) at −40° C. The reaction mixture was stirred at 0° C. for 2 hours. The reaction mixture was poured in saturated ammonium chloride aqueous solution and extracted with ethyl acetate. The organic layer was washed with a saturated saline solution and dried over anhydrous magnesium sulfate. The solvent was evaporated and the obtained residue was purified with column chromatography on silica gel (hexane:ethyl acetate=7:3) to give the title compound (269 mg) having the following physical data.

TLC: Rf 0.45 (hexane:ethyl acetate=7:3);
$^1$H-NMR (CDCl$_3$): δ 0.91 (m, 3 H), 1.15 (s, 1 H), 1.26 (t, J=7.14 Hz, 3 H), 1.33 (m, 4 H), 1.49 (m, 6 H), 3.20 (m, 2 H), 3.87 (m, 2 H), 4.13 (q, J=7.14 Hz, 2 H)

REFERENCE EXAMPLE 2

4-butyl-4-piperidinol

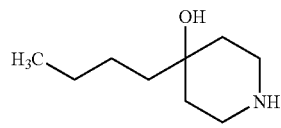

The compound prepared in Reference Example 1 (259 mg) was dissolved in a mixed solvent of dioxane and ethanol (1:1, 12 mL) and thereto was added 5N sodium hydrate aqueous solution (4.0 mL) at room temperature. The reaction mixture was refluxed for 48 hours. The reaction mixture was cooled to room temperature and the solvent was evaporated under reduced pressure. The residue was dissolved with ethylene glycol (3 mL) and was stirred at 100° C. for 64 hours. The reaction mixture was cooled to room temperature, was acidified with 1N hydrochloric acid and then was washed with diethylether. The aqueous layer was alkalified with 1N sodium hydrate and extracted with chloroform. The organic layer was dried over anhydrous magnesium sulfate, then evaporated under reduced pressure to give the title compound (104 mg) having the following physical data.

TLC: Rf 0.15 (chloroform:methanol:28% ammonia water=80:20:4);
$^1$H-NMR (CDCl$_3$): δ 0.91 (m, 3 H), 1.34 (m, 4 H), 1.51 (m, 8 H), 2.83 (m, 2 H), 2.94 (m, 2 H)

EXAMPLE 1

4-butyl-4-hydroxy-N-(3-phenoxyphenyl)-1-piperidinecarboxamide

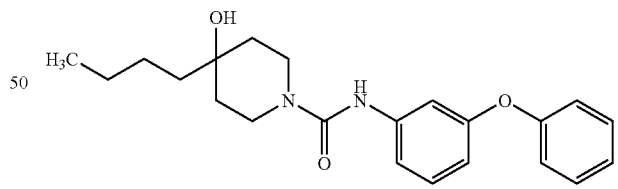

A solution of the compound prepared in Reference Example 2 (43 mg) in 1,2-dichloroethane (2 mL) was added 3-phenoxyphenylisocyanate. The reaction solution was stirred at room temperature for 18 hours. The reaction mixture was purified by column chromatography on silica gel (hexane:ethyl acetate=1:2) to give the title compound (47 mg) having the following physical data.

TLC: Rf 0.35 (hexane:ethyl acetate=1:2);
$^1$H-NMR (CDCl$_3$): δ 0.93 (m, 3 H), 1.33 (m, 5 H), 1.48 (m, 2 H), 1.60 (m, 4 H), 3.31 (m, 2 H), 3.78 (m, 2 H), 6.46 (s, 1 H), 6.68 (m, 1 H), 7.01 (m, 2 H), 7.05 (m, 1 H), 7.11 (m, 2 H), 7.23 (t, J=8.15 Hz, 1 H), 7.32 (m, 2 H)

EXAMPLE 1(1)-1(87)

By the same procedure as described in Example 1 using the corresponding amine instead of amine prepared in Reference Example 2 and the corresponding isocyanate instead of 3-phenoxyphenylisocyanate, the following compounds of the present invention were obtained.

EXAMPLE 1(1)

4-(4-bromophenyl)-N-(3,5-dichlorophenyl)-4-hydroxy-1-piperidinecarboxamide

HPLC retention time: 4.11 min;
MS (ESI, Pos. 20 V):447, 445 (M+H)$^+$, 429, 427

EXAMPLE 1(2)

4-(4-chlorophenyl)-4-hydroxy-N-(3-phenoxyphenyl)-1-piperidinecarboxamide

HPLC retention time: 3.98 min;
MS (ESI, Pos. 20 V): 425, 423 (M+H)$^+$, 407, 405

EXAMPLE 1(3)

4-(4-chlorophenyl)-N-(3,5-dichlorophenyl)-4-hydroxy-1-piperidinecarboxamide

HPLC retention time: 4.03 min;
MS (ESI, Pos. 20 V): 401, 399 (M+H)$^+$, 383, 381

EXAMPLE 1(4)

4-(4-fluorophenyl)-4-hydroxy-N-(3-phenoxyphenyl)-1-piperidinecarboxamide

HPLC retention time: 3.89 min;
MS (ESI, Pos. 20 V): 407 (M+H)$^+$, 389

EXAMPLE 1(5)

N-(3,5-dichlorophenyl)-4-(4-fluorophenyl)-4-hydroxy-1-piperidinecarboxamide

HPLC retention time: 3.93 min;
MS (ESI, Pos. 20 V): 385, 383 (M+H)$^+$, 367, 365

EXAMPLE 1(6)

4-hydroxy-N-(3-phenoxyphenyl)-4-phenyl-1-piperidinecarboxamide

HPLC retention time: 3.86 min;
MS (ESI, Pos. 20 V): 389 (M+H)$^+$, 371

EXAMPLE 1(7)

N-(3,5-dichlorophenyl)-4-hydroxy-4-phenyl-1-piperidinecarboxamide

HPLC retention time: 3.91 min;
MS (ESI, Pos. 20 V): 367, 365 (M+H)$^+$, 348

EXAMPLE 1(8)

4-(2-ethylbutyl)-4-hydroxy-N-(3-(trifluoromethyl)phenyl)-1-piperidinecarboxamide HPLC retention time: 4.00 min;
MS (ESI, Pos. 20 V): 745 (2M+H)$^+$, 373 (M+H)$^+$

EXAMPLE 1(9)

N-(2,6-dichloro-4-pyridinyl)-4-(2-ethylbutyl)-4-hydroxy-1-piperidinecarboxamide

HPLC retention time: 3.95 min;
MS (ESI, Pos. 20 V): 376, 374 (M+H)$^+$

EXAMPLE 1(10)

4-(4-bromophenyl)-4-hydroxy-N-(3-(((2E)-3-phenyl-2-propenoyl)amino)phenyl)-1-piperidinecarboxamide HPLC retention time: 3.79 min;
MS (ESI, Pos. 20 V): 522, 520 (M+H)$^+$, 504, 502

EXAMPLE 1(11)

4-(4-bromophenyl)-4-hydroxy-N-(3-((3-methylbutanoyl)amino)phenyl)-1-piperidinecarboxamide HPLC retention time: 3.64 min;
MS (ESI, Pos. 20 V): 949, 947 (2M+H)$^+$, 476, 474 (M+H)$^+$, 458, 456

EXAMPLE 1(12)

4-(4-bromophenyl)-N-(3-(((2E)-3-(2-chlorophenyl)-2-propenoyl)amino)phenyl)-4-hydroxy-1-piperidinecarboxamide HPLC retention time: 3.89 min;
MS (ESI, Pos. 20 V): 556, 554 (M+H)$^+$, 538, 536

EXAMPLE 1(14)

N-(3-fluorophenyl)-4-hydroxy-4-isopropyl-1-piperidinecarboxamide

HPLC retention time: 3.42 min;
MS (ESI, Pos. 20 V): 281 (M+H)$^+$

EXAMPLE 1(15)

4-(cyclohexylmethyl)-4-hydroxy-N-(3-phenoxyphenyl)-1-piperidinecarboxamide

HPLC retention time: 4.13 min;
MS (ESI, Pos. 20 V): 409 (M+H)$^+$

EXAMPLE 1(16)

4-cyclopentyl-4-hydroxy-N-(3-phenoxyphenyl)-1-piperidinecarboxamide

HPLC retention time: 3.91 min;
MS (ESI, Pos. 20 V): 761 (2M+H)$^+$, 381 (M+H)$^+$

EXAMPLE 1(17)

4-cyclopentyl-N-(3,5-dichlorophenyl)-4-hydroxy-1-piperidinecarboxamide

HPLC retention time: 4.00 min;
MS (ESI, Pos. 20 V): 359, 357 (M+H)+, 339

EXAMPLE 1(18)

ethyl 3-(((4-hydroxy-4-(5-methyl-2-pyridinyl)-1-piperidinyl)carbonyl)amino)benzoate HPLC retention time: 3.08 min;
MS (ESI, Pos. 20 V): 767 (2M+H)+, 384 (M+H)+, 193

EXAMPLE 1(19)

N-(3,5-bis(trifluoromethyl)phenyl)-4-hydroxy-4-phenyl-1-piperidinecarboxamide

HPLC retention time: 4.03 min;
MS (ESI, Pos. 20 V): 865 (2M+H)+, 433 (M+H)+, 415

EXAMPLE 1(21)

N-(3,5-bis(trifluoromethyl)phenyl)-4-(4-fluorophenyl)-4-hydroxy-1-piperidinecarboxamide HPLC retention time: 4.04 min;
MS (ESI, Pos. 20 V): 901 (2M+H)+, 451 (M+H)+, 433

EXAMPLE 1(22)

4-cyclohexyl-4-hydroxy-N-(3-(trifluoromethyl)phenyl)-1-piperidinecarboxamide

HPLC retention time: 3.91 min;
MS (ESI, Pos. 20 V): 741 (2M+H)+, 371 (M+H)+

EXAMPLE 1(23)

N-(3-chlorophenyl)-4-cyclohexyl-4-hydroxy-1-piperidinecarboxamide

HPLC retention time: 3.82 min;
MS (ESI, Pos. 20 V): 673 (2M+H)+, 339, 337 (M+H)+

EXAMPLE 1(24)

4-hydroxy-4-(3-methylbutyl)-N-(3-phenoxyphenyl)-1-piperidinecarboxamide

HPLC retention time: 4.00 min;
MS (ESI, Pos. 20 V): 765 (2M+H)+, 383 (M+H)+

EXAMPLE 1(25)

4-hydroxy-4-(3-methylbutyl)-N-(3-(trifluoromethyl)phenyl)-1-piperidinecarboxamide HPLC retention time: 3.91 min;
MS (ESI, Pos. 20 V): 717 (2M+H)+, 359 (M+H)+

EXAMPLE 1(26)

N-(3,5-bis(trifluoromethyl)phenyl)-4-hydroxy-4-(3-methylbutyl)-1-piperidinecarboxamide HPLC retention time: 4.20 min;
MS (ESI, Pos. 20 V): 853 (2M+H)+, 427 (M+H)+, 409

EXAMPLE 1(27)

N-(3,5-dichlorophenyl)-4-hydroxy-4-(3-methylbutyl)-1-piperidinecarboxamide

HPLC retention time: 4.07 min;
MS (ESI, Pos. 20 V): 719, 717 (2M+H)+, 361, 359 (M+H)+, 343, 341

EXAMPLE 1(28)

4-cyclobutyl-4-hydroxy-N-(3-phenoxyphenyl)-1-piperidinecarboxamide

HPLC retention time: 3.82 min;
MS (ESI, Pos. 20 V): 733 (2M+H)+, 367 (M+H)+

EXAMPLE 1(29)

4-cyclobutyl-N-(3,5-dichlorophenyl)-4-hydroxy-1-piperidinecarboxamide

HPLC retention time: 3.88 min;
MS (ESI, Pos. 20 V): 687, 685 (2M+H)+, 345, 343 (M+H)+

EXAMPLE 1(30)

N-(3,5-bis(trifluoromethyl)phenyl)-4-hydroxy-4-(2-naphthyl)-1-piperidinecarboxamide HPLC retention time: 4.18 min;
MS (ESI, Pos. 20 V): 965 (2M+H)+, 483 (M+H)+, 465

EXAMPLE 1(31)

N-(3-fluoro-5-(trifluoromethyl)phenyl)-4-hydroxy-4-phenyl-1-piperidinecarboxamide HPLC retention time: 3.83 min;
MS (ESI, Pos. 20 V): 765 (2M+H)+, 383 (M+H)+, 365

EXAMPLE 1(32)

4-(4-bromophenyl)-N-(3-fluoro-5-(trifluoromethyl)phenyl)-4-hydroxy-1-piperidinecarboxamide HPLC retention time: 4.01 min;
MS (ESI, Pos. 20 V): 923, 921 (2M+H)+, 463, 461 (M+H)+, 445, 443

EXAMPLE 1(33)

4-cyclobutyl-N-(3-fluoro-5-(trifluoromethyl)phenyl)-4-hydroxy-1-piperidinecarboxamide HPLC retention time: 3.84 min;
MS (ESI, Pos. 20 V): 721 (2M+H)+, 361 (M+H)+

EXAMPLE 1(34)

4-cyclopentyl-N-(3-fluoro-5-(trifluoromethyl)phenyl)-4-hydroxy-1-piperidinecarboxamide HPLC retention time: 3.94 min;
MS (ESI, Pos. 20 V): 749 (2M+H)$^+$, 375 (M+H)$^+$

EXAMPLE 1(35)

4-tert-butyl-N-(3-fluoro-5-(trifluoromethyl)phenyl)-4-hydroxy-1-piperidinecarboxamide HPLC retention time: 3.87 min;
MS (ESI, Pos. 20 V): 725 (2M+H)$^+$, 363 (M+H)$^+$

EXAMPLE 1(36)

4-butyl-N-(3-fluoro-5-(trifluoromethyl)phenyl)-4-hydroxy-1-piperidinecarboxamide HPLC retention time: 3.91 min;
MS (ESI, Pos. 20 V): 725 (2M+H)$^+$, 363 (M+H)$^+$, 345

EXAMPLE 1(37)

N-(3-fluoro-5-(trifluoromethyl)phenyl)-4-hydroxy-4-(3-methylbutyl)-1-piperidinecarboxamide HPLC retention time: 4.01 min;
MS (ESI, Pos. 20 V): 753 (2M+H)$^+$, 377 (M+H)$^+$, 359

EXAMPLE 1(38)

4-cyclohexyl-N-(3-(cyclohexyloxy)phenyl)-4-hydroxy-1-piperidinecarboxamide

HPLC retention time: 4.11 min;
MS (ESI, Pos. 20 V): 801 (2M+H)$^+$, 401 (M+H)$^+$, 383

EXAMPLE 1(39)

N-(3-(cyclohexyloxy)phenyl)-4-(2-ethylbutyl)-4-hydroxy-1-piperidinecarboxamide

HPLC retention time: 4.21 min;
MS (ESI, Pos. 20 V): 805 (2M+H)$^+$, 403 (M+H)$^+$

EXAMPLE 1(40)

4-(cyclopentylmethyl)-4-hydroxy-N-(3-phenoxyphenyl)-1-piperidinecarboxamide

HPLC retention time: 4.02 min;
MS (ESI, Pos. 20 V): 789 (2M+H)$^+$, 395 (M+H)$^+$

EXAMPLE 1(41)

4-(cyclopentylmethyl)-4-hydroxy-N-(3-(trifluoromethyl)phenyl)-1-piperidinecarboxamide HPLC retention time: 3.95 min;
MS (ESI, Pos. 20 V): 741 (2M+H)$^+$, 371 (M+H)$^+$

EXAMPLE 1(43)

4-(cyclopentylmethyl)-N-(3,5-dichlorophenyl)-4-hydroxy-1-piperidinecarboxamide

HPLC retention time: 4.11 min;
MS (ESI, Pos. 20 V): 743, 741 (2M+H)$^+$, 373, 371 (M+H)$^+$

EXAMPLE 1(44)

4-(1-ethylpropyl)-4-hydroxy-N-(3-(trifluoromethyl)phenyl)-1-piperidinecarboxamide HPLC retention time: 3.73 min;
MS (ESI, Pos. 20 V): 717 (2M+H)$^+$, 359 (M+H)$^+$

EXAMPLE 1(45)

N-(3,5-dichlorophenyl)-4-(1-ethylpropyl)-4-hydroxy-1-piperidinecarboxamide

HPLC retention time: 3.93 min;
MS (ESI, Pos. 20 V): 719, 717 (2M+H)$^+$, 361, 359 (M+H)$^+$, 343, 341

EXAMPLE 1(46)

N-(3,5-bis(trifluoromethyl)phenyl)-4-hydroxy-4-(3-methylphenyl)-1-piperidinecarboxamide HPLC retention time: 3.96 min;
MS (ESI, Pos. 20 V): 893 (2M+H)$^+$, 447 (M+H)$^+$, 429

EXAMPLE 1(47)

N-(3-fluoro-5-(trifluoromethyl)phenyl)-4-hydroxy-4-(3-methylphenyl)-1-piperidinecarboxamide HPLC retention time: 3.79 min;
MS (ESI, Pos. 20 V): 793 (2M+H)$^+$, 397 (M+H)$^+$, 379

EXAMPLE 1(48)

N-(3,5-bis(trifluoromethyl)phenyl)-4-hydroxy-4-(4-methylphenyl)-1-piperidinecarboxamide HPLC retention time: 3.96 min;
MS (ESI, Pos. 20 V): 893 (2M+H)$^+$, 447 (M+H)$^+$, 429

EXAMPLE 1(49)

N-(3-fluoro-5-(trifluoromethyl)phenyl)-4-hydroxy-4-(4-methylphenyl)-1-piperidinecarboxamide HPLC retention time: 3.79 min;
MS (ESI, Pos. 20 V): 793 (2M+H)$^+$, 397 (M+H)$^+$, 379

EXAMPLE 1(50)

4-(4-bromophenyl)-N-(3-chloro-5-fluorophenyl)-4-hydroxy-1-piperidinecarboxamide

HPLC retention time: 3.79 min;
MS (ESI, Pos. 20 V): 855, 853 (2M+H)$^+$, 429, 427 (M+H)$^+$, 411, 409

EXAMPLE 1(51)

N-(3-chloro-5-fluorophenyl)-4-(4-chlorophenyl)-4-hydroxy-1-piperidinecarboxamide HPLC retention time: 3.76 min;
MS (ESI, Pos. 20 V): 767, 765 (2M+H)$^+$, 385, 383 (M+H)$^+$, 367, 365

EXAMPLE 1(52)

N-(3-chloro-5-fluorophenyl)-4-(4-fluorophenyl)-4-hydroxy-1-piperidinecarboxamide HPLC retention time: 3.65 min;
MS (ESI, Pos. 20 V): 733 (2M+H)$^+$, 369, 367 (M+H)$^+$, 351, 349

EXAMPLE 1(53)

N-(3-chloro-5-fluorophenyl)-4-cyclohexyl-4-hydroxy-1-piperidinecarboxamide

HPLC retention time: 3.81 min;
MS (ESI, Pos. 20 V): 709 (2M+H)$^+$, 357, 355 (M+H)$^+$

EXAMPLE 1(54)

N-(3-chloro-5-fluorophenyl)-4-(2-ethylbutyl)-4-hydroxy-1-piperidinecarboxamide

HPLC retention time: 3.91 min;
MS (ESI, Pos. 20 V): 713 (2M+H)$^+$, 359, 357 (M+H)$^+$, 341, 339

EXAMPLE 1(55)

N-(3-chloro-5-fluorophenyl)-4-(1-ethylpropyl)-4-hydroxy-1-piperidinecarboxamide

HPLC retention time: 3.79 min;
MS (ESI, Pos. 20 V): 685 (2M+H)$^+$, 345, 343 (M+H)$^+$, 327, 325

EXAMPLE 1(56)

N-(3-chloro-5-fluorophenyl)-4-(cyclopentylmethyl)-4-hydroxy-1-piperidinecarboxamide HPLC retention time: 3.85 min;
MS (ESI, Pos. 20 V): 709 (2M+H)$^+$, 357, 355 (M+H)$^+$

EXAMPLE 1(57)

4-(4-bromophenyl)-4-hydroxy-N-(3-(trifluoromethyl)phenyl)-1-piperidinecarboxamide TLC: Rf 0.38 (hexane:ethyl acetate=1:1)
$^1$H-NMR (CDCl$_3$): δ 7.66 (br-s, 1 H), 7.56 (br-d, J=8.4 Hz, 2 H), 7.49 (m, 2 H), 7.39 (t, J=7.8 Hz, 1 H), 7.35 (m, 2 H), 7.28 (br-d, J=8.7 Hz, 1 H), 6.63 (s, 1 H), 4.00 (m, 2 H), 3.42 (m, 2 H), 2.04 (dt, J=4.7, 13.4 Hz, 2 H), 1.79 (m, 2 H)

EXAMPLE 1(58)

4-butyl-N-(3,5-dichlorophenyl)-4-hydroxy-1-piperidinecarboxamide

TLC: Rf 0.32 (hexane:ethyl acetate=1:1);
$^1$H-NMR (DMSO-d$_6$): δ 0.88 (t, J=6.00 Hz, 3 H), 1.35 (m, 10 H), 3.15 (m, 2 H), 3.79 (m, 2 H), 4.18 (s, 1 H), 7.07 (t, J=1.83 Hz, 1 H), 7.59 (d, J=1.83 Hz, 2 H), 8.76 (s, 1 H)

EXAMPLE 1(60)

N-(3,5-bis(trifluoromethyl)phenyl)-4-(4-bromophenyl)-4-hydroxy-1-piperidinecarboxamide TLC: Rf 0.39 (hexane:ethyl acetate=1:1);
$^1$H-NMR (DMSO-d$_6$): δ 1.63 (m, 2 H), 1.89 (m, 2 H), 3.23 (m, 2 H), 4.04 (m, 2 H), 5.24 (s, 1 H), 7.45 (d, J=8.50 Hz, 2 H), 7.50 (d, J=8.50 Hz, 2 H), 7.57 (s, 1 H), 8.24 (s, 2 H), 9.16 (s, 1 H)

EXAMPLE 1(61)

4-(2-ethylbutyl)-4-hydroxy-N-(3-phenoxyphenyl)-1-piperidinecarboxamide

TLC: Rf 0.29 (hexane:ethyl acetate=1:1);
$^1$H-NMR (DMSO-d$_6$): δ 0.79 (t, J=7.50 Hz, 6 H), 1.33 (m, 11 H), 3.10 (m, 2 H), 3.73 (m, 2 H), 4.09 (s, 1 H), 6.55 (m, 1 H), 6.99 (m, 2 H), 7.11 (t, J=7.50 Hz, 1 H), 7.20 (m, 3 H), 7.37 (m, 2 H), 8.48 (s, 1 H)

EXAMPLE 1(62)

N-(3,5-dichlorophenyl)-4-(2-ethylbutyl)-4-hydroxy-1-piperidinecarboxamide

TLC: Rf 0.44 (hexane:ethyl acetate=1:1)
$^1$H-NMR (DMSO-d$_6$): δ 0.80 (t, J=7.00 Hz, 6 H), 1.35 (m, 11 H), 3.12 (m, 2 H), 3.77 (m, 2 H), 4.13 (s, 1 H), 7.07 (t, J=2.00 Hz, 1 H), 7.58 (d, J=2.00 Hz, 2 H), 8.75 (s, 1 H)

EXAMPLE 1(63)

N-(3,5-bis(trifluoromethyl)phenyl)-4-(2-ethylbutyl)-4-hydroxy-1-piperidinecarboxamide TLC: Rf 0.51 (hexane:ethyl acetate=1:1);
$^1$H-NMR (DMSO-d$_6$): δ 0.80 (t, J=7.00 Hz, 6 H), 1.33 (m, 11 H), 3.18 (m, 2 H), 3.81 (m, 2 H), 4.15 (s, 1 H), 7.55 (s, 1 H), 8.21 (s, 2 H), 9.09 (s, 1 H)

EXAMPLE 1(64)

4-(2-ethylbutyl)-N-(3-fluoro-5-(trifluoromethyl)phenyl)-4-hydroxy-1-piperidinecarboxamide TLC: Rf 0.46 (hexane:ethyl acetate=1:1);
$^1$H-NMR (DMSO-d$_6$): δ 0.80 (t, J=7.00 Hz, 6 H), 1.34 (m, 11 H), 3.12 (m, 2 H), 3.81 (m, 2 H), 4.14 (s, 1 H), 7.13 (d, J=8.50 Hz, 1 H), 7.70 (m, 2 H), 8.95 (s, 1 H)

EXAMPLE 1(65)

4-(4-fluorophenyl)-N-(3-fluoro-5-(trifluoromethyl)phenyl)-4-hydroxy-1-piperidinecarboxamide TLC: Rf 0.43 (hexane:ethyl acetate=1:1);
$^1$H-NMR (DMSO-d$_6$): δ 1.62 (m, 2 H), 1.87 (m, 2 H), 3.23 (m, 2 H), 4.02 (m, 2 H), 5.18 (s, 1 H), 7.12 (m, 3 H), 7.52 (dd, J=9.00, 5.50 Hz, 2 H), 7.74 (m, 2 H), 9.02 (s, 1 H)

EXAMPLE 1(66)

4-(4-chlorophenyl)-N-(3-fluoro-5-(trifluoromethyl) phenyl)-4-hydroxy-1-piperidinecarboxamide TLC: Rf 0.43 (hexane:ethyl acetate=1:1);
$^1$H-NMR (DMSO-d$_6$): δ 1.63 (m, 2 H), 1.88 (m, 2 H), 3.23 (m, 2 H), 4.02 (m, 2 H), 5.23 (s, 1 H), 7.15 (d, J=8.50 Hz, 1 H), 7.36 (d, J=8.50 Hz, 2 H), 7.51 (d, J=8.50 Hz, 2 H), 7.74 (m, 2 H), 9.02 (s, 1 H)

EXAMPLE 1(67)

4-cyclohexyl-4-hydroxy-N-(3-phenoxyphenyl)-1-piperidinecarboxamide

TLC: Rf 0.28 (hexane: ethyl acetate=1:1);
$^1$H-NMR (CDCl$_3$): δ 1.07 (m, 2 H), 1.22 (m, 4 H), 1.60 (m, 6 H), 1.82 (m, 4 H), 3.26 (m, 2 H), 3.84 (m, 2 H), 6.35 (s, 1 H), 6.68 (m, 1 H), 7.03 (m, 3 H), 7.11 (m, 2 H), 7.29 (m, 3 H)

EXAMPLE 1(68)

N-(3,5-bis(trifluoromethyl)phenyl)-4-cyclohexyl-4-hydroxy-1-piperidinecarboxamide TLC: Rf 0.61 (hexane:ethyl acetate=1:1)
$^1$H-NMR (CDCl$_3$): δ 1.01 (m, 2 H), 1.22 (m, 4 H), 1.63 (m, 6 H), 1.83 (m, 4 H), 3.27 (m, 2 H), 3.88 (m, 2 H), 6.95 (s, 1 H), 7.48 (s, 1 H), 7.87 (s, 2 H)

EXAMPLE 1(69)

4-cyclohexyl-N-(3-fluoro-5-(trifluoromethyl)phenyl)-4-hydroxy-1-piperidinecarboxamide TLC: Rf 0.48 (hexane:ethyl acetate=1:1);
$^1$H-NMR (CDCl$_3$): δ 1.04 (m, 2 H), 1.24 (m, 4 H), 1.62 (m, 6 H), 1.84 (m, 4 H), 3.30 (m, 2 H), 3.88 (m, 2 H), 6.62 (s, 1 H), 6.96 (d, J=8.24 Hz, 1 H), 7.31 (s, 1 H), 7.55 (m, 1 H)

EXAMPLE 1(70)

4-cyclohexyl-N-(3,5-dichlorophenyl)-4-hydroxy-1-piperidinecarboxamide

TLC: Rf 0.49 (hexane:ethyl acetate=1:1);
$^1$H-NMR (CDCl$_3$): δ 1.02 (m, 2 H), 1.22 (m, 4 H), 1.62 (m, 6 H), 1.81 (m, 4 H), 3.25 (m, 2 H), 3.86 (m, 2 H), 6.61 (s, 1 H), 6.99 (t, J=1.83 Hz, 1 H), 7.33 (d, J=1.83 Hz, 2 H)

EXAMPLE 1(71)

N-(3,5-bis(trifluoromethyl)phenyl)-4-(cyclopentylmethyl)-4-hydroxy-1-piperidinecarboxamide TLC: Rf 0.57 (hexane:ethyl acetate=1:1);
$^1$H-NMR (CDCl$_3$): δ 1.14 (m, 2 H), 1.17 (s, 1 H), 1.59 (m, 10 H), 1.90 (m, 3 H), 3.35 (m, 2 H), 3.84 (m, 2 H), 6.75 (s, 1 H), 7.50 (s, 1 H), 7.88 (s, 2 H)

EXAMPLE 1(72)

N-(3,5-bis(trifluoromethyl)phenyl)-4-(1-ethylpropyl)-4-hydroxy-1-piperidinecarboxamide TLC: Rf 0.25 (hexane:ethyl acetate=2:1);
$^1$H-NMR (DMSO-d$_6$): δ 0.91 (m, 7 H), 1.12 (m, 2 H), 1.51 (m, 6 H), 3.13 (m, 2 H), 3.92 (m, 2 H), 4.10 (s, 1 H), 7.55 (s, 1 H), 8.21 (s, 2 H), 9.09 (s, 1 H)

EXAMPLE 1(73)

4-(1-ethylpropyl)-N-(3-fluoro-5-(trifluoromethyl)phenyl)-4-hydroxy-1-piperidinecarboxamide TLC: Rf 0.17 (hexane:ethyl acetate=2:1);
$^1$H-NMR (DMSO-d$_6$): δ 0.89 (m, 7 H), 1.10 (m, 2 H), 1.51 (m, 6 H), 3.11 (m, 2 H), 3.88 (m, 2 H), 4.09 (s, 1 H), 7.13 (d, J=8.00 Hz, 1 H), 7.71 (m, 2 H), 8.94 (s, 1 H)

EXAMPLE 1(74)

4-(1-ethylpropyl)-4-hydroxy-N-(3-phenoxyphenyl)-1-piperidinecarboxamide

TLC: Rf 0.28 (hexane:ethyl acetate=1:1);
$^1$H-NMR (DMSO-d$_6$): δ 0.89 (m, 7 H), 1.09 (m, 2 H), 1.49 (m, 6 H), 3.05 (m, 2 H), 3.83 (m, 2 H), 4.03 (s, 1 H), 6.55 (m, 1 H), 6.98 (d, J=8.00 Hz, 2 H), 7.11 (t, J=8.00 Hz, 1 H), 7.20 (m, 3 H), 7.38 (t, J=8.00 Hz, 2 H), 8.48 (s, 1 H)

EXAMPLE 1(75)

N-(3,5-bis(trifluoromethyl)phenyl)-4-cyclopropyl-4-hydroxy-1-piperidinecarboxamide TLC: Rf 0.35 (hexane:ethyl acetate=1:1);
$^1$H-NMR (DMSO-d$_6$): δ 0.19 (m, 2 H), 0.33 (m, 2 H), 0.84 (m, 1 H), 1.48 (m, 4 H), 3.15 (m, 2 H), 3.86 (m, 2 H), 3.98 (s, 1 H), 7.56 (s, 1 H), 8.22 (s, 2 H), 9.11 (s, 1 H)

EXAMPLE 1(76)

N-(3,5-bis(trifluoromethyl)phenyl)-4-cyclobutyl-4-hydroxy-1-piperidinecarboxamide TLC: Rf 0.38 (hexane:ethyl acetate=1:1);
$^1$H-NMR (DMSO-d$_6$): δ 1.25 (m, 2 H), 1.36 (m, 2 H), 1.71 (m, 4 H), 1.95 (m, 2 H), 2.26 (m, 1 H), 3.15 (m, 2 H), 3.83 (m, 2 H), 4.19 (s, 1 H), 7.56 (s, 1 H), 8.21 (s, 2 H), 9.09 (s, 1 H)

EXAMPLE 1(78)

N-(3,5-bis(trifluoromethyl)phenyl)-4-hydroxy-4-(4-methoxyphenyl)-1-piperidinecarboxamide TLC: Rf 0.37 (hexane:ethyl acetate=1:1);
$^1$H-NMR (DMSO-d$_6$): δ 1.64 (m, 2 H), 1.85 (m, 2 H), 3.23 (m, 2 H), 3.72 (s, 3 H), 4.02 (m, 2 H), 5.03 (s, 1 H), 6.87 (d, J=9.00 Hz, 2 H), 7.40 (d, J=9.00 Hz, 2 H), 7.57 (s, 1 H), 8.24 (s, 2 H), 9.16 (s, 1 H)

EXAMPLE 1(79)

N-(3,5-bis(trifluoromethyl)phenyl)-4-hydroxy-4-(3-methoxyphenyl)-1-piperidinecarboxamide TLC: Rf 0.40 (hexane:ethyl acetate=1:1);
$^1$H-NMR (DMSO-d$_6$): δ 1.64 (m, 2 H), 1.90 (m, 2 H), 3.25 (m, 2 H), 3.74 (s, 3 H), 4.04 (m, 2 H), 5.13 (s, 1 H), 6.78 (m, 1 H), 7.05 (m, 2 H), 7.23 (t, J=8.00 Hz, 1 H), 7.57 (s, 1 H), 8.24 (s, 2 H) 9.16 (s, 1 H)

EXAMPLE 1(80)

4-(2-ethylbutyl)-4-hydroxy-N-(3-(tetrahydro-2H-pyran-4-yloxy)phenyl)-1-piperidinecarboxamide TLC: Rf 0.23 (hexane:ethyl acetate=1:2);
$^1$H-NMR (DMSO-d$_6$): δ 0.80 (t, J=7.50 Hz, 6 H) 1.44 (m, 13 H) 1.94 (m, 2 H) 3.11 (m, 2 H) 3.44 (m, 2 H) 3.81 (m, 4 H) 4.10 (s, 1 H) 4.44 (m, 1 H) 6.51 (d, J=8.00 Hz, 1 H) 7.01 (d, J=8.00 Hz, 1 H) 7.07 (t, J=8.00 Hz, 1 H) 7.16 (s, 1 H) 8.35 (s, 1 H)

EXAMPLE 1(81)

4-(2-ethylbutyl)-4-hydroxy-N-[3-(4-methylphenoxy)phenyl]piperidine-1-carboxamide TLC: Rf 0.33 (hexane:ethyl acetate=1:1);
$^1$H-NMR (DMSO-$d_6$): δ 0.79 (t, J=7.00 Hz, 6 H), 1.27 (m, 11 H), 2.27 (s, 3 H), 3.10 (m, 2 H), 3.74 (m, 2 H), 4.09 (s, 1 H), 6.51 (m, 1 H), 6.89 (d, J=8.50 Hz, 2 H), 7.17 (m, 5 H), 8.45 (m, 1 H)

EXAMPLE 1(82)

4-(2-ethylbutyl)-4-hydroxy-N-[3-(2-methylphenoxy)phenyl]piperidine-1-carboxamide TLC: Rf 0.33 (hexane:ethyl acetate=1:1);
$^1$H-NMR (DMSO-$d_6$): δ 0.79 (t, J=7.00 Hz, 6 H), 1.33 (m, 11 H), 2.15 (s, 3 H), 3.09 (m, 2 H), 3.75 (m, 2 H), 4.09 (s, 1 H), 6.45 (m, 1 H), 6.87 (d, J=8.00 Hz, 1 H), 7.12 (m, 5 H), 7.30 (d, J=8.00 Hz, 1 H), 8.44 (s, 1 H)

EXAMPLE 1(83)

4-(2-ethylbutyl)-4-hydroxy-N-[3-(2-methoxyphenoxy)phenyl]piperidine-1-carboxamide TLC: Rf 0.17 (hexane:ethyl acetate=1:1);
$^1$H-NMR (DMSO-$d_6$): δ 0.79 (t, J=7.50 Hz, 6 H), 1.33 (m, 11 H), 3.09 (m, 2 H), 3.73 (s, 3 H), 3.75 (m, 2 H), 4.08 (s, 1 H), 6.38 (dt, J=7.00, 2.50 Hz, 1 H), 7.05 (m, 7 H), 8.41 (s, 1 H)

EXAMPLE 1(84)

4-(2-ethylbutyl)-4-hydroxy-N-[3-(4-methoxyphenoxy)phenyl]piperidine-1-carboxamide TLC: Rf 0.21 (hexane:ethyl acetate=1:1);
$^1$H-NMR (DMSO-$d_6$): δ 0.79 (t, J=7.50 Hz, 6 H), 1.32 (m, 11 H), 3.09 (m, 2 H), 3.73 (s, 3 H), 3.75 (m, 2 H), 4.08 (s, 1 H), 6.47 (m, 1 H), 6.96 (m. 4 H), 7.14 (m, 3 H), 8.43 (s, 1 H)

EXAMPLE 1(85)

4-(2-ethylbutyl)-N-[3-(4-fluorophenoxy)phenyl]-4-hydroxypiperidine-1-carboxamide TLC: Rf 0.26 (hexane:ethyl acetate=1:1);
$^1$H-NMR (DMSO-$d_6$): δ 0.79 (t, J=7.50 Hz, 6 H), 1.31 (m, 11 H), 3.10 (m, 2 H), 3.73 (m, 2 H), 4.09 (s, 1 H), 6.53 (m, 1 H), 7.03 (dd, J=9.00, 4.50 Hz, 2 H), 7.21 (m, 5 H), 8.47 (s, 1 H)

EXAMPLE 1(86)

4-(2-ethylbutyl)-4-hydroxy-N-{3-[4-(trifuloromethyl)phenoxy]phenyl}piperidine-1-carboxamide TLC: Rf 0.31 (hexane:ethyl acetate=1:1);
$^1$H-NMR (DMSO-$d_6$): δ 0.79 (t, J=7.50 Hz, 6 H), 1.31 (m, 11 H), 3.12 (m, 2 H), 3.77 (m, 2 H), 4.10 (s, 1 H), 6.67 (m, 1 H), 7.13 (d, J=8.50 Hz, 2 H), 7.29 (m, 3 H), 7.72 (d, J=8.50 Hz, 2 H), 8.55 (s, 1 H)

EXAMPLE 1(87)

N-[3,5-bis(trifuloromethyl)phenyl]-3-{4-[4-(trifuloromethoxy)phenyl]piperazin-1-yl}azetidine-1-carboxamide TLC: Rf 0.48 (hexane:ethyl acetate=3:7);
$^1$H-NMR (CDCl$_3$): δ 2.56 (t, J=4.95 Hz, 4 H), 3.21 (t, J=4.95 Hz, 4 H), 3.32 (m, 1 H), 4.03 (dd, J=8.32, 5.13 Hz, 2 H), 4.14 (t, J=8.32 Hz, 2 H), 6.37 (s, 1 H), 6.89 (d, J=9.15 Hz, 2 H), 7.12 (d, J=9.15 Hz, 2 H) 7.51 (s, 1 H) 7.92 (s, 2 H)

EXAMPLE 2(1) -2(73)

By the same procedure as described in Example 1 using the corresponding amine instead of amine prepared in Reference Example 2 and the corresponding isocyanate or isothiocyanate instead of 3-phenoxyphenylisocyanate, the following compounds of the present invention were obtained.

EXAMPLE 2(1)

4-(4-bromophenyl)-N-(3-chlorophenyl)-4-hydroxy-1-piperidinecarboxamide

HPLC retention time: 3.82 min;
MS (ESI, Pos. 20V): 817 (2M+H)$^+$, 409 (M+H)$^+$, 391

EXAMPLE 2(2)

4-(4-bromophenyl)-4-hydroxy-N-(3-(methylthio)phenyl)-1-piperidinecarboxamide

HPLC retention time: 3.75 min;
MS (ESI, Pos. 20V): 841 (2M+H)$^+$, 421 (M+H)$^+$, 403

EXAMPLE 2(3)

4-hydroxy-4-phenyl-N-(3-(trifluoromethyl)phenyl)-1-piperidinecarboxamide

HPLC retention time: 3.73 min;
MS (ESI, Pos. 20V): 729 (2M+H)$^+$, 365 (M+H)$^+$, 347

EXAMPLE 2(4)

4-(4-chlorophenyl)-4-hydroxy-N-(3-(trifluoromethyl)phenyl)-1-piperidinecarboxamide HPLC retention time: 3.91 min;
MS (ESI, Pos. 20 V): 401, 399 (M+H)$^+$, 383, 381

EXAMPLE 2(5)

4-(4-fluorophenyl)-4-hydroxy-N-(3-(trifluoromethyl)phenyl)-1-piperidinecarboxamide HPLC retention time: 3.78 min;
MS (ESI, Pos. 20 V): 383 (M+H)$^+$, 365

EXAMPLE 2(6)

N-(3,5-dichlorophenyl)-4-hydroxy-4-(4-methylphenyl)-1-piperidinecarboxamide

HPLC retention time: 4.06 min;
MS (ESI, Pos. 20V): 757 (2M+H)$^+$, 379 (M+H)$^+$, 361

EXAMPLE 2(7)

N-(3,5-dichlorophenyl)-4-hydroxy-4-(1,3-thiazolidin-3-ylmethyl)-1-piperidinecarboxamide HPLC retention time: 3.18 min;
MS (ESI, Pos. 20 V): 392, 390 (M+H)$^+$

EXAMPLE 2(8)

4-hydroxy-4-pentyl-N-(3-(trifluoromethyl)phenyl)-1-piperidinecarboxamide

HPLC retention time: 3.91 min;
MS (ESI, Pos. 20 V): 717 (2M+H)$^+$, 359 (M+H)$^+$

EXAMPLE 2(9)

4-hexyl-4-hydroxy-N-(3-(trifluoromethyl)phenyl)-1-piperidinecarboxamide

HPLC retention time: 4.02 min;
MS (ESI, Pos. 20 V): 745 (2M+H)$^+$, 373 (M+H)$^+$

EXAMPLE 2(10)

N-(3,4-dichlorophenyl)-4-hydroxy-4-pentyl-1-piperidinecarboxamide

HPLC retention time 3.99 min;
MS (ESI, Pos. 20 V): 719, 717 (2M+H)$^+$, 361, 359 (M+H)$^+$

EXAMPLE 2(11)

N-(3,4-dichlorophenyl)-4-hexyl-4-hydroxy-1-piperidinecarboxamide

HPLC retention time: 4.13 min;
MS (ESI, Pos. 20 V): 747, 745 (2M+H)$^+$, 375, 373 (M+H)$^+$, 355

EXAMPLE 2(12)

N-(3,5-dichlorophenyl)-4-((ethyl(2-fluoro-3-(trifluoromethyl)benzoyl)amino)methyl)-4-hydroxy-1-piperidinecarboxamide HPLC retention time: 3.97 min;
MS (ESI, Pos. 20 V): 538, 536 (M+H)$^+$

EXAMPLE 2(13)

N-(3,5-dichlorophenyl)-4-((ethylthio)methyl)-4-hydroxy-1-piperidinecarboxamide

HPLC retention time: 3.82 min;
MS (ESI, Pos. 20 V): 365, 363 (M+H)$^+$, 345

EXAMPLE 2(14)

N-(3,4-dichlorophenyl)-4-((ethylthio)methyl)-4-hydroxy-1-piperidinecarboxamide

HPLC retention time: 3.73 min;
MS (ESI, Pos. 20 V): 365, 363 (M+H)$^+$, 345

EXAMPLE 2(15)

4-tert-butyl-4-hydroxy-N-(3-phenoxyphenyl)-1-piperidinecarboxamide

HPLC retention time: 3.86 min;
MS (ESI, Pos. 20 V): 737 (2M+H)$^+$, 369 (M+H)$^+$

EXAMPLE 2(16)

N-(3-bromophenyl)-4-cyclopentyl-4-hydroxy-1-piperidinecarboxamide

HPLC retention time: 3.77 min;
MS (ESI, Pos. 20 V): 369, 367 (M+H)$^+$

EXAMPLE 2(17)

4-cyclopentyl-4-hydroxy-N-(3-(trifluoromethyl)phenyl)-1-piperidinecarboxamide

HPLC retention time: 3.82 min;
MS (ESI, Pos. 20 V): 357 (M+H)$^+$

EXAMPLE 2(18)

N-(3-chlorophenyl)-4-cyclopentyl-4-hydroxy-1-piperidinecarboxamide

HPLC retention time: 3.73 min;
MS (ESI, Pos. 20 V): 645 (2M+H)$^+$, 325, 323 (M+H)$^+$

EXAMPLE 2(19)

4-cyclopentyl-N-(3-ethylphenyl)-4-hydroxy-1-piperidinecarboxamide

HPLC retention time: 3.75 min;
MS (ESI, Pos. 20 V): 317 (M+H)$^+$

EXAMPLE 2(20)

4-cyclopentyl-N-(3,5-dimethylphenyl)-4-hydroxy-1-piperidinecarboxamide

HPLC retention time: 3.75 min;
MS (ESI, Pos. 20 V): 317 (M+H)$^+$

EXAMPLE 2(21)

4-cyclopentyl-N-(3,4-dichlorophenyl)-4-hydroxy-1-piperidinecarboxamide

HPLC retention time: 3.91 min;
MS (ESI, Pos. 20 V): 359, 357 (M+H)$^+$, 339

EXAMPLE 2(22)

4-cyclopentyl-N-(2,6-dichloro-4-pyridinyl)-4-hydroxy-1-piperidinecarboxamide

HPLC 3.78 min;
MS (ESI, Pos. 20 V): 360, 358 (M+H)$^+$

EXAMPLE 2(23)

4-cyclohexyl-N-(2,6-dichloro-4-pyridinyl)-4-hydroxy-1-piperidinecarboxamide

HPLC retention time: 3.86 min;
MS (ESI, Pos. 20 V): 374, 372 (M+H)$^+$

EXAMPLE 2(24)

N-(2,6-dichloro-4-pyridinyl)-4-hydroxy-4-(3-methylbutyl)-1-piperidinecarboxamide HPLC retention time: 3.86 min;
MS (ESI, Pos. 20 V): 362, 360 (M+H)$^+$

EXAMPLE 2(25)

4-cyclopropyl-4-hydroxy-N-(3-phenoxyphenyl)-1-piperidinecarboxamide

HPLC retention time: 3.71 min;
MS (ESI, Pos. 20 V): 705 (2M+H)$^+$, 353 (M+H)$^+$

EXAMPLE 2(26)

4-cyclopropyl-N-(3,5-dichlorophenyl)-4-hydroxy-1-piperidinecarboxamide

HPLC retention time: 3.73 min;
MS (ESI, Pos. 20 V): 659, 657 (2M+H)$^+$, 331, 329 (M+H)$^+$

EXAMPLE 2(27)

4-cyclobutyl-4-hydroxy-N-(3-(trifluoromethyl)phenyl)-1-piperidinecarboxamide

HPLC retention time: 3.70 min;
MS (ESI, Pos. 20 V): 685 (2M+H)$^+$, 343 (M+H)$^+$

EXAMPLE 2(28)

N-(3,5-dichlorophenyl)-4-hydroxy-4-(2-naphthyl)-1-piperidinecarboxamide

HPLC retention time: 4.08 min;
MS (ESI, Pos. 20 V): 831, 829 (2M+H)$^+$, 417, 415 (M+H)$^+$, 399, 397

EXAMPLE 2(29)

4-cyclohexyl-N-(3-(cyclopentyloxy)phenyl)-4-hydroxy-1-piperidinecarboxamide

HPLC retention time: 4.03 min;
MS (ESI, Pos. 20 V): 773 (2M+H)$^+$, 387 (M+H)$^+$

EXAMPLE 2(30)

N-(3-(cyclopentyloxy)phenyl)-4-hydroxy-4-(3-methylbutyl)-1-piperidinecarboxamide HPLC retention time: 4.00 min;
MS (ESI, Pos. 20 V): 749 (2M+H)$^+$, 375 (M+H)$^+$

EXAMPLE 2(31)

N-(3-(cyclopentyloxy)phenyl)-4-(2-ethylbutyl)-4-hydroxy-1-piperidinecarboxamide

HPLC retention time: 4.12 min;
MS (ESI, Pos. 20 V): 777 (2M+H)$^+$, 389 (M+H)$^+$

EXAMPLE 2(32)

N-(3-(cyclohexyloxy)phenyl)-4-hydroxy-4-phenyl-1-piperidinecarboxamide

HPLC retention time: 3.92 min;
MS (ESI, Pos. 20 V): 789 (2M+H)$^+$, 395 (M+H)$^+$

EXAMPLE 2(33)

N-(3-(cyclohexyloxy)phenyl)-4-(4-fluorophenyl)-4-hydroxy-1-piperidinecarboxamide HPLC retention time: 3.95 min;
MS (ESI, Pos. 20 V): 825 (2M+H)$^+$, 413 (M+H)$^+$

EXAMPLE 2(34)

4-cyclobutyl-N-(3-(cyclohexyloxy)phenyl)-4-hydroxy-1-piperidinecarboxamide

HPLC retention time: 3.93 min;
MS (ESI, Pos. 20 V): 745 (2M+H)$^+$, 373 (M+H)$^+$

EXAMPLE 2(35)

N-(3-(cyclohexyloxy)phenyl)-4-cyclopentyl-4-hydroxy-1-piperidinecarboxamide

HPLC retention time: 4.01 min;
MS (ESI, Pos. 20 V): 773 (2M+H)$^+$, 387 (M+H)$^+$

EXAMPLE 2(36)

4-tert-butyl-N-(3-(cyclohexyloxy)phenyl)-4-hydroxy-1-piperidinecarboxamide

HPLC retention time: 3.95 min;
MS (ESI, Pos. 20 V): 749 (2M+H)$^+$, 375 (M+H)$^+$

EXAMPLE 2(37)

4-butyl-N-(3-(cyclohexyloxy)phenyl)-4-hydroxy-1-piperidinecarboxamide

HPLC retention time: 4.00 min;
MS (ESI, Pos. 20 V): 749 (2M+H)$^+$, 375 (M+H)$^+$

EXAMPLE 2(38)

N-(3-(cyclohexyloxy)phenyl)-4-hydroxy-4-(3-methylbutyl)-1-piperidinecarboxamide

HPLC retention time: 4.10 min;
MS (ESI, Pos. 20 V): 777 (2M+H)$^+$, 389 (M+H)$^+$

EXAMPLE 2(39)

N-(3-(cyclohexyloxy)phenyl)-4-(cyclopentylmethyl)-4-hydroxy-1-piperidinecarboxamide HPLC retention time: 4.15 min;
MS (ESI, Pos. 20 V): 801 (2M+H)$^+$, 401 (M+H)$^+$

EXAMPLE 2(40)

N-(3-chlorophenyl)-4-(cyclopentylmethyl)-4-hydroxy-1-piperidinecarboxamide

HPLC retention time: 3.86 min;
MS (ESI, Pos. 20 V): 673 (2M+H)$^+$, 339, 337 (M+H)$^+$

EXAMPLE 2(41)

4-(cyclopentylmethyl)-N-(2,6-dichloro-4-pyridinyl)-4-hydroxy-1-piperidinecarboxamide HPLC retention time: 3.88 min;
MS (ESI, Pos. 20 V): 374, 372 (M+H)$^+$

EXAMPLE 2(42)

4-hydroxy-N-(3-phenoxyphenyl)-4-(1-propylbutyl-1-piperidinecarboxamide

HPLC retention time: 4.07 min;
MS (ESI, Pos. 20 V): 821 (2M+H)$^+$, 411 (M+H)$^+$, 393

EXAMPLE 2(43)

N-(3-fluoro-5-(trifluoromethyl)phenyl)-4-hydroxy-4-(1-propylbutyl)-1-piperidinecarboxamide HPLC retention time: 4.11 min;
MS (ESI, Pos. 20 V): 809 (2M+H)$^+$, 405 (M+H)$^+$, 387

EXAMPLE 2(44)

N-(3,5-difluorophenyl)-4-hydroxy-4-(1-propylbutyl-1-piperidinecarboxamide

HPLC retention time: 3.92 min;
MS (ESI, Pos. 20 V): 709 (2M+H)$^+$, 355 (M+H)$^+$

EXAMPLE 2(45)

N-(3-chlorophenyl)-4-hydroxy-4-(1-propylbutyl)-1-piperidinecarboxamide

HPLC retention time: 3.93 min;
MS (ESI, Pos. 20 V): 705 (2M+H)$^+$, 355, 353 (M+H)$^+$, 337, 335

EXAMPLE 2(46)

N-(3,5-dichlorophenyl)-4-hydroxy-4-(1-propylbutyl)-1-piperidinecarboxamide

HPLC retention time: 4.18 min;
MS (ESI, Pos. 20 V): 775, 773 (2M+H)$^+$, 391, 389, 387 (M+H)$^+$

EXAMPLE 2(47)

N-(2,6-dichloro-4-pyridinyl)-4-hydroxy-4-(1-propylbutyl)-1-piperidinecarboxamide HPLC retention time: 3.97 min;
MS (ESI, Pos. 20 V): 390, 388 (M+H)$^+$

EXAMPLE 2(48)

N-(3-(cyclopentyloxy)phenyl)-4-(1-ethylpropyl)-4-hydroxy-1-piperidinecarboxamide HPLC retention time: 3.85 min;
MS (ESI, Pos. 20 V): 749 (2M+H)$^+$, 375 (M+H)$^+$, 357

EXAMPLE 2(49)

N-(3-(cyclohexyloxy)phenyl)-4-(1-ethylpropyl)-4-hydroxy-1-piperidinecarboxamide

HPLC retention time: 3.96 min;
MS (ESI, Pos. 20 V): 777 (2M+H)$^+$, 389 (M+H)$^+$, 371

EXAMPLE 2(50)

N-(3,5-difluorophenyl)-4-(1-ethylpropyl)-4-hydroxy-1-piperidinecarboxamide

HPLC retention time: 3.67 min;
MS (ESI, Pos. 20 V): 653 (2M+H)$^+$, 327 (M+H)$^+$

EXAMPLE 2(51)

N-(3-chlorophenyl)-4-(1-ethylpropyl)-4-hydroxy-1-piperidinecarboxamide

HPLC retention time: 3.66 min;
MS (ESI, Pos. 20 V): 649 (2M+H)$^+$, 327, 325 (M+H)$^+$

EXAMPLE 2(52)

N-(2,6-dichloro-4-pyridinyl)-4-(1-ethylpropyl)-4-hydroxy-1-piperidinecarboxamide HPLC retention time: 3.68 min;
MS (ESI, Pos. 20 V): 362, 360 (M+H)$^+$

EXAMPLE 2(53)

N-(3,5-bis(trifluoromethyl)phenyl)-4-hydroxy-4-(2-methylphenyl)-1-piperidinecarboxamide HPLC retention time: 3.98 min;
MS (ESI, Pos. 20 V): 893 (2M+H)$^+$, 447 (M+H)$^+$, 429

EXAMPLE 2(54)

N-(3-fluoro-5-(trifluoromethyl)phenyl)-4-hydroxy-4-(2-methylphenyl)-1-piperidinecarboxamide HPLC retention time: 3.81 min;
MS (ESI, Pos. 20 V): 793 (2M+H)$^+$, 397 (M+H)$^+$, 379

EXAMPLE 2(55)

N-(3-(cyclohexyloxy)phenyl)-4-hydroxy-4-(3-methylphenyl)-1-piperidinecarboxamide HPLC retention time: 3.87 min;
MS (ESI, Pos. 20 V): 817 (2M+H)$^+$, 409 (M+H)$^+$, 391

EXAMPLE 2(56)

4-benzyl-N-(3-fluoro-5-(trifluoromethyl)phenyl)-4-hydroxy-1-piperidinecarboxamide HPLC retention time: 3.75 min;
MS (ESI, Pos. 20 V): 793 (2M+H)$^+$, 397 (M+H)$^+$, 379

EXAMPLE 2(57)

N-(3-chloro-5-fluorophenyl)-4-hydroxy-4-phenyl-1-piperidinecarboxamide

HPLC retention time: 3.63 min;
MS (ESI, Pos. 20 V): 697 (2M+H)$^+$, 351, 349 (M+H)$^+$, 333, 331

EXAMPLE 2(58)

N-(3-chloro-5-fluorophenyl)-4-hydroxy-4-(4-methylphenyl)-1-piperidinecarboxamide HPLC retention time: 3.70 min;
MS (ESI, Pos. 20 V): 725 (2M+H)$^+$, 365, 363 (M+H)$^+$, 347, 345

EXAMPLE 2(59)

N-(3-chloro-5-fluorophenyl)-4-hydroxy-4-(3-methylphenyl)-1-piperidinecarboxamide HPLC retention time: 3.71 min;
MS (ESI, Pos. 20 V): 725 (2M+H)$^+$, 365, 363 (M+H)$^+$, 347, 345

EXAMPLE 2(60)

N-(3-chloro-5-fluorophenyl)-4-cyclobutyl-4-hydroxy-1-piperidinecarboxamide

HPLC retention time: 3.60 min;
MS (ESI, Pos. 20 V): 653 (2M+H)$^+$, 329, 327 (M+H)$^+$, 311, 309

EXAMPLE 2(61)

N-(3-chloro-5-fluorophenyl)-4-cyclopentyl-4-hydroxy-1-piperidinecarboxamide

HPLC retention time: 3.71 min;
MS (ESI, Pos. 20 V): 681 (2M+H)$^+$, 343, 341 (M+H)$^+$

EXAMPLE 2(62)

4-tert-butyl-N-(3-chloro-5-fluorophenyl)-4-hydroxy-1-piperidinecarboxamide

HPLC retention time: 3.63 min;
MS (ESI, Pos. 20 V): 657 (2M+H)$^+$, 331, 329 (M+H)$^+$

EXAMPLE 2(63)

4-butyl-N-(3-chloro-5-fluorophenyl)-4-hydroxy-1-piperidinecarboxamide

HPLC retention time: 3.68 min;
MS (ESI, Pos. 20 V): 657 (2M+H)$^+$, 331, 329 (M+H)$^+$

EXAMPLE 2(64)

N-(3-chloro-5-fluorophenyl)-4-hydroxy-4-(3-methylbutyl)-1-piperidinecarboxamide

HPLC retention time: 3.80 min;
MS (ESI, Pos. 20 V): 685 (2M+H)$^+$, 345, 343 (M+H)$^+$

EXAMPLE 2(65)

N-(3-chloro-5-fluorophenyl)-4-hydroxy-4-(1-propylbutyl)-1-piperidinecarboxamide

HPLC retention time: 4.06 min;
MS (ESI, Pos. 20 V): 741 (2M+H)$^+$, 373, 371 (M+H)$^+$

EXAMPLE 2(66)

N-(3-chloro-5-fluorophenyl)-4-((ethylthio)methyl)-4-hydroxy-1-piperidinecarboxamide HPLC retention time: 3.55 min;
MS (ESI, Pos. 20 V): 693 (2M+H)$^+$, 349, 347 (M+H)$^+$, 331, 329

EXAMPLE 2(67)

N-(3-chloro-5-fluorophenyl)-4-hydroxy-4-(2-naphthyl)-1-piperidinecarboxamide

HPLC retention time: 3.82 min;
MS (ESI, Pos. 20 V): 797 (2M+H)$^+$, 401, 399 (M+H)$^+$, 383, 381

EXAMPLE 2(68)

4-benzyl-N-(3-chloro-5-fluorophenyl)-4-hydroxy-1-piperidinecarboxamide

HPLC retention time: 3.68 min;
MS (ESI, Pos. 20 V): 725 (2M+H)$^+$, 365, 363 (M+H)$^+$, 347, 345

EXAMPLE 2(69)

4-(4-bromophenyl)-4-hydroxy-N-(3-((trifluoromethyl)thio)phenyl)-1-piperidinecarbothioamide $^1$H-NMR (CDCl$_3$): δ 1.80 (m, 3 H), 2.15 (m, 2 H), 3.60 (m, 2 H), 4.52 (m, 2 H), 7.41 (m, 9 H);
TLC: Rf 0.50 (hexane:ethyl acetate=1:1)

EXAMPLE 2(70)

4-(4-bromophenyl)-4-hydroxy-N-(3-(trifluoromethoxy)phenyl)-1-piperidinecarboxamide HPLC retention time: 3.93 min;
MS (ESI, Pos. 20 V): 919, 917 (2M+H)$^+$, 461, 459 (M+H)$^+$, 443, 441

EXAMPLE 1(71)

4-hydroxy-4-isopropyl-N-(3-phenoxyphenyl)-1-piperidinecarboxamide

HPLC retention time: 3.75 min;
MS (ESI, Pos. 20 V): 709 (2M+H)$^+$, 355 (M+H)$^+$

EXAMPLE 2(72)

4-(cyclohexylmethyl)-4-hydroxy-N-(3-(trifluoromethyl)phenyl)-1-piperidinecarboxamide HPLC retention time: 4.02 min;
MS (ESI, Pos. 20V): 769 (2M+H)$^+$, 385 (M+H)$^+$

EXAMPLE 2(73)

4-(cyclohexylmethyl)-N-(3,5-dimethylphenyl)-4-hydroxy-1-piperidinecarboxamide

HPLC retention time: 3.97 min;
MS (ESI, Pos. 20V): 345 (M+H)$^+$

EXAMPLE 3(1) -3(264)

By the same procedure as described in Example 1 using the corresponding amine instead of amine prepared in Reference Example 2 and the corresponding isocyanate, isothiocyanate or activated ester of carboxylic acid instead of 3-phenoxyphenylisocyanate, the following compounds of the present invention were obtained.

EXAMPLE 3(1)

N-(3-chlorophenyl)-4-(4-chlorophenyl)-4-hydroxy-1-piperidinecarboxamide

EXAMPLE 3(2)

4-(4-bromophenyl)-4-hydroxy-N-(3-methylphenyl)-1-piperidinecarboxamide

EXAMPLE 3(3)

4-(4-bromophenyl)-4-hydroxy-N-(4-(trifluoromethyl)phenyl)-1-piperidinecarboxamide

EXAMPLE 3(4)

4-(4-bromophenyl)-N-(4-chlorophenyl)-4-hydroxy-1-piperidinecarboxamide

EXAMPLE 3(5)

4-(4-bromophenyl)-N-(4-ethoxyphenyl)-4-hydroxy-1-piperidinecarboxamide

EXAMPLE 3(6)

N,4-bis(4-bromophenyl)-4-hydroxy-1-piperidinecarboxamide

EXAMPLE 3(7)

4-(4-bromophenyl)-4-hydroxy-N-phenyl-1-piperidinecarbothioamide

EXAMPLE 3(8)

4-(4-bromophenyl)-4-hydroxy-N-(4-methoxyphenyl)-1-piperidinecarboxamide

EXAMPLE 3(9)

4-(4-bromophenyl)-N-(2-chlorophenyl)-4-hydroxy-1-piperidinecarbothioamide

EXAMPLE 3(10)

4-(4-bromophenyl)-4-hydroxy-N-(4-(methylthio)phenyl)-1-piperidinecarbothioamide

EXAMPLE 3(11)

methyl 3-(((4-(4-bromophenyl)-4-hydroxy-1-piperidinyl)carbonyl)amino)benzoate

EXAMPLE 3(12)

N-(3-bromophenyl)-4-(4-bromophenyl)-4-hydroxy-1-piperidinecarboxamide

EXAMPLE 3(13)

4-(4-bromophenyl)-N-(3-cyanophenyl)-4-hydroxy-1-piperidinecarboxamide

EXAMPLE 3(14)

4-(4-bromophenyl)-4-hydroxy-N-(3-phenoxyphenyl)-1-piperidinecarboxamide

EXAMPLE 3(15)

4-(4-bromophenyl)-4-hydroxy-N-(4-phenoxyphenyl)-1-piperidinecarboxamide

EXAMPLE 3(16)

4-(4-bromophenyl)-N-(3,5-difluorophenyl)-4-hydroxy-1-piperidinecarboxamide

EXAMPLE 3(17)

4-(4-bromophenyl)-N-(3,5-dimethylphenyl)-4-hydroxy-1-piperidinecarboxamide

EXAMPLE 3(18)

4-(4-bromophenyl)-N-(3,4-dichlorophenyl)-4-hydroxy-1-piperidinecarboxamide

EXAMPLE 3(19)

methyl 3-(((4-(4-chlorophenyl)-4-hydroxy-1-piperidinyl)carbonyl)amino)benzoate

EXAMPLE 3(20)

N-(3-bromophenyl)-4-(4-chlorophenyl)-4-hydroxy-1-piperidinecarboxamide

EXAMPLE 3(21)

4-(4-chlorophenyl)-N-(3-cyanophenyl)-4-hydroxy-1-piperidinecarboxamide

EXAMPLE 3(22)

ethyl 3-(((4-(4-chlorophenyl)-4-hydroxy-1-piperidinyl)carbonyl)amino)benzoate

EXAMPLE 3(23)

4-(4-chlorophenyl)-4-hydroxy-N-(3-(methylthio)phenyl)-1-piperidinecarboxamide

EXAMPLE 3(24)

4-(4-chlorophenyl)-4-hydroxy-N-(4-phenoxyphenyl)-1-piperidinecarboxamide

EXAMPLE 3(25)

N,4-bis(4-chlorophenyl)-4-hydroxy-1-piperidinecarboxamide

EXAMPLE 3(26)

N-(4-bromophenyl)-4-(4-chlorophenyl)-4-hydroxy-1-piperidinecarboxamide

EXAMPLE 3(27)

4-(4-chlorophenyl)-N-(3,5-difluorophenyl)-4-hydroxy-1-piperidinecarboxamide

EXAMPLE 3(28)

4-(4-chlorophenyl)-N-(3,4-dichlorophenyl)-4-hydroxy-1-piperidinecarboxamide

EXAMPLE 3(29)

4-(4-chlorophenyl)-N-(2,6-dichloro-4-pyridinyl)-4-hydroxy-1-piperidinecarboxamide

EXAMPLE 3(30)

N-(3-bromophenyl)-4-(4-fluorophenyl)-4-hydroxy 1-piperidinecarboxamide

EXAMPLE 3(31)

N-(3-ethylphenyl)-4-(4-fluorophenyl)-4-hydroxy-1-piperidinecarboxamide

EXAMPLE 3(32)

N-(3,4-dichlorophenyl)-4-(4-fluorophenyl)-4-hydroxy-1-piperidinecarboxamide

EXAMPLE 3(33)

4-hydroxy-N,4-bis(3-(trifluoromethyl)phenyl)-1-piperidinecarboxamide

EXAMPLE 3(34)

4-(2-fluorophenyl)-N-(3-(trifluoromethyl)phenyl)-1-piperidinecarboxamide

EXAMPLE 3(35)

N-(3,5-dimethylphenyl)-4-(2-fluorophenyl)-1-piperidinecarboxamide

EXAMPLE 3(36)

ethyl 3-(((4-(2-methylphenyl)-1-piperidinyl)carbonyl)amino)benzoate

EXAMPLE 3(37)

4-(2-methylphenyl)-N-(4-(methylthio)phenyl)-1-piperidinecarboxamide

EXAMPLE 3(38)

4-(3-fluorophenyl)-N-(3-(trifluoromethyl)phenyl)-1-piperidinecarboxamide

EXAMPLE 3(39)

4-(4-fluorophenyl)-N-(3-(trifluoromethyl)phenyl)-1-piperidinecarboxamide

EXAMPLE 3(40)

ethyl 3-(((4-(4-methylphenyl)-1-piperidinyl)carbonyl)amino)benzoate

EXAMPLE 3(41)

4-(4-methylphenyl)-N-(3-(trifluoromethyl)phenyl)-1-piperidinecarboxamide

EXAMPLE 3(42)

ethyl 3-(((4-(4-(methoxycarbonyl)phenyl)-1-piperidinyl)carbonyl)amino)benzoate

EXAMPLE 3(43)

methyl 4-(1-(((3-(trifluoromethyl)phenyl)amino)carbonyl)-4-piperidinyl)benzoate

EXAMPLE 3(44)

N-(3-bromophenyl)-4-hydroxy-4-phenyl-1-piperidinecarboxamide

EXAMPLE 3(45)

N-(3-ethylphenyl)-4-hydroxy-4-phenyl-1-piperidinecarboxamide

EXAMPLE 3(46)

N-(3,4-dichlorophenyl)-4-hydroxy-4-phenyl-1-piperidinecarboxamide

EXAMPLE 3(47)

4-hydroxy-4-(2-methylphenyl)-N-(3-phenoxyphenyl)-1-piperidinecarboxamide

EXAMPLE 3(48)

4-hydroxy-4-(3-methylphenyl)-N-(3-(trifluoromethyl)phenyl)-1-piperidinecarboxamide

EXAMPLE 3(49)

4-hydroxy-4-(3-methylphenyl)-N-(3-phenoxyphenyl)-1-piperidinecarboxamide

EXAMPLE 3(50)

N-(3,5-dichlorophenyl)-4-hydroxy-4-(3-methylphenyl)-1-piperidinecarboxamide

EXAMPLE 3(51)

N-(3,4-dichlorophenyl)-4-hydroxy-4-(3-methylphenyl)-1-piperidinecarboxamide

EXAMPLE 3(52)

N-(2,6-dichloro-4-pyridinyl)-4-hydroxy-4-(3-methylphenyl)-1-piperidinecarboxamide

EXAMPLE 3(53)

4-hydroxy-4-(4-methylphenyl)-N-(3-(trifluoromethyl)phenyl)-1-piperidinecarboxamide

EXAMPLE 3(54)

N-(2,6-dichloro-4-pyridinyl)-4-hydroxy-4-(4-methylphenyl)-1-piperidinecarboxamide

EXAMPLE 3(55)

N-(3,5-dichlorophenyl)-4-hydroxy-4-((6-methyl-3,4-dihydro-1 (2H)-quinolinyl)methyl)-1-piperidinecarboxamide

EXAMPLE 3(56)

tert-butyl 4-((1-(((3,5-dichlorophenyl)amino)carbonyl)-4-hydroxy-4-piperidinyl)methyl)-1-piperazine carboxylate

EXAMPLE 3(57)

4-butyl-N-(3-ethylphenyl)-4-hydroxy-1-piperidinecarboxamide

EXAMPLE 3(58)

N-(3-fluorophenyl)-4-hydroxy-4-methyl-1-piperidinecarboxamide

EXAMPLE 3(59)

N-(3-fluorophenyl)-4-hydroxy-4-propyl-1-piperidinecarboxamide

EXAMPLE 3(60)

N-(3-bromophenyl)-4-butyl-4-hydroxy-1-piperidinecarboxamide

EXAMPLE 3(61)

N-(3,5-dichlorophenyl)-4-hydroxy-4-propyl-1-piperidinecarboxamide

EXAMPLE 3(62)

4-hydroxy-4-methyl-N-(3-(trifluoromethyl)phenyl)-1-piperidinecarboxamide

EXAMPLE 3(63)

4-butyl-4-hydroxy-N-(3-(trifluoromethyl)phenyl)-1-piperidinecarboxamide

EXAMPLE 3(64)

4-ethyl-4-hydroxy-N-(3-(methylthio)phenyl)-1-piperidinecarboxamide

EXAMPLE 3(65)

N-(3-chlorophenyl)-4-hydroxy-4-methyl-1-piperidinecarboxamide

EXAMPLE 3(66)

N-(3,4-dichlorophenyl)-4-hydroxy-4-methyl-1-piperidinecarboxamide

EXAMPLE 3(67)

N-(3-chlorophenyl)-4-hydroxy-4-propyl-1-piperidinecarboxamide

EXAMPLE 3(68)

N-(3,4-dichlorophenyl)-4-hydroxy-4-propyl-1-piperidinecarboxamide

EXAMPLE 3(69)

4-butyl-N-(3-chlorophenyl)-4-hydroxy-1-piperidinecarboxamide

EXAMPLE 3(70)

4-butyl-N-(3,4-dichlorophenyl)-4-hydroxy-1-piperidinecarboxamide

EXAMPLE 3(71)

N-(2,6-dichloro-4-pyridinyl)-4-hydroxy-4-propyl-1-piperidinecarboxamide

EXAMPLE 3(72)

4-butyl-N-(2,6-dichloro-4-pyridinyl)-4-hydroxy-1-piperidinecarboxamide

EXAMPLE 3(73)

N-(3-ethylphenyl)-4-hydroxy-4-pentyl-1-piperidinecarboxamide

EXAMPLE 3(74)

N-(3-fluorophenyl)-4-hydroxy-4-pentyl-1-piperidinecarboxamide

EXAMPLE 3(75)

methyl 3-(((4-hexyl-4-hydroxy-1-piperidinyl)carbonyl)amino)benzoate

EXAMPLE 3(76)

N-(3-cyanophenyl)-4-hydroxy-4-pentyl-1-piperidinecarboxamide

EXAMPLE 3(77)

4-hydroxy-4-pentyl-N-(4-(trifluoromethyl)phenyl)-1-piperidinecarboxamide

EXAMPLE 3(78)

N-(3-cyanophenyl)-4-hexyl-4-hydroxy-1-piperidinecarboxamide

EXAMPLE 3(79)

ethyl 3-(((4-hydroxy-4-pentyl-1-piperidinyl)carbonyl)amino)benzoate

EXAMPLE 3(80)

ethyl 3-(((4-hexyl-4-hydroxy-1-piperidinyl)carbonyl)amino)benzoate

EXAMPLE 3(81)

N-(3,5-difluorophenyl)-4-hydroxy-4-pentyl-1-piperidinecarboxamide

EXAMPLE 3(82)

4-hydroxy-N-(3-(methylthio)phenyl)-4-pentyl-1-piperidinecarboxamide

EXAMPLE 3(83)

4-hexyl-4-hydroxy-N-(3-(methylthio)phenyl)-1-piperidinecarboxamide

EXAMPLE 3(84)

N-(3-chlorophenyl)-4-hydroxy-4-pentyl-1-piperidinecarboxamide

EXAMPLE 3(85)

N-(3-chlorophenyl)-4-hexyl-4-hydroxy-1-piperidinecarboxamide

EXAMPLE 3(86)

N-(2,6-dichloro-4-pyridinyl)-4-hydroxy-4-pentyl-1-piperidinecarboxamide

EXAMPLE 3(87)

N-(3,5-dichlorophenyl)-4-((ethyl(3-methylbenzoyl)amino)methyl)-4-hydroxy-1-piperidinecarboxamide

EXAMPLE 3(88)

N-(3,5-dichlorophenyl)-4-((ethyl(4-methylbenzoyl)amino)methyl)-4-hydroxy-1-piperidinecarboxamide

EXAMPLE 3(89)

N-(3,5-dichlorophenyl)-4-((ethyl(heptanoyl)amino)methyl)-4-hydroxy-1-piperidinecarboxamide

EXAMPLE 3(90)

N-(3,5-dichlorophenyl)-4-((ethyl(hexanoyl)amino)methyl)-4-hydroxy-1-piperidinecarboxamide

EXAMPLE 3(91)

N-(3,5-dichlorophenyl)-4-((ethyl((2E)-3-phenyl-2-propenoyl)amino)methyl)-4-hydroxy-1-piperidinecarboxamide

EXAMPLE 3(92)

N-(3,5-dichlorophenyl)-4-((ethyl(2-naphthoyl)amino)methyl)-4-hydroxy-1-piperidinecarboxamide

EXAMPLE 3(93)

4-(((3-chlorobenzoyl)(ethyl)amino)methyl)-N-(3,5-dichlorophenyl)-4-hydroxy-1-piperidinecarboxamide

EXAMPLE 3(94)

4-(((2,3-dichlorobenzoyl)(ethyl)amino)methyl)-N-(3,5-dichlorophenyl)-4-hydroxy-1-piperidinecarboxamide

EXAMPLE 3(95)

4-(((3-cyclopentylpropanoyl)(ethyl)amino)methyl)-N-(3,5-dichlorophenyl)-4-hydroxy-1-piperidinecarboxamide

EXAMPLE 3(96)

N-(3,5-dichlorophenyl)-4-(((2,4-difluorobenzoyl)(ethyl)amino)methyl)-4-hydroxy-1-piperidinecarboxamide

EXAMPLE 3(97)

4-(((cyclopentylacetyl)(ethyl)amino)methyl)-N-(3,5-dichlorophenyl)-4-hydroxy-1-piperidinecarboxamide

EXAMPLE 3(98)

N-(3,5-dichlorophenyl)-4-((((3,4-dimethoxyphenyl)acetyl)(ethyl)amino)methyl)-4-hydroxy-1-piperidinecarboxamide

EXAMPLE 3(99)

4-(((3-chloro-4-fluorobenzoyl)(ethyl)amino)methyl)-N-(3,5-dichlorophenyl)-4-hydroxy-1-piperidinecarboxamide

EXAMPLE 3(100)

N-(3,5-dichlorophenyl)-4-((ethyl(2-fluoro-5-(trifluoromethyl)benzoyl)amino)methyl)-4-hydroxy-1-piperidinecarboxamide

EXAMPLE 3(101)

N-(3,5-dichlorophenyl)-4-((ethyl(3-fluoro-4-(trifluoromethyl)benzoyl)amino)methyl)-4-hydroxy-1-piperidinecarboxamide

EXAMPLE 3(102)

N-(3,5-dichlorophenyl)-4-((ethyl((2E)-3-(3-(trifluoromethyl)phenyl)-2-propenoyl)amino)methyl)-4-hydroxy-1-piperidinecarboxamide

EXAMPLE 3(103)

N-(3,5-dichlorophenyl)-4-((ethyl(3-fluoro-4-methylbenzoyl)amino)methyl)-4-hydroxy-1-piperidinecarboxamide

EXAMPLE 3(104)

N-(3,5-dichlorophenyl)-4-((ethyl(4-(trifluoromethoxy)benzoyl)amino)methyl)-4-hydroxy-1-piperidinecarboxamide

EXAMPLE 3(105)

N-(3,5-dichlorophenyl)-4-((ethyl(((1R*,2R*)-2-phenylcyclopropyl)carbonyl)amino)methyl)-4-hydroxy-1-piperidinecarboxamide

EXAMPLE 3(106)

N-(3,5-dichlorophenyl)-4-((ethyl(2-fluoro-4-(trifluoromethyl)benzoyl)amino)methyl)-4-hydroxy-1-piperidinecarboxamide

EXAMPLE 3(107)

4-(4-bromophenyl)-4-hydroxy-N-(3-((3-methylbenzoyl)amino)phenyl)-1-piperidinecarboxamide

EXAMPLE 3(108)

4-(4-bromophenyl)-N-(3-((4-fluorobenzoyl)amino)phenyl)-4-hydroxy-1-piperidinecarboxamide

EXAMPLE 3(109)

4-(4-bromophenyl)-N-(3-(heptanoylamino)phenyl)-4-hydroxy-1-piperidinecarboxamide

EXAMPLE 3(110)

4-(4-bromophenyl)-4-hydroxy-N-(3-((2-methoxybenzoyl)amino)phenyl)-1-piperidinecarboxamide

EXAMPLE 3(111)

4-(4-bromophenyl)-N-(3-(hexanoylamino)phenyl)-4-hydroxy-1-piperidinecarboxamide

EXAMPLE 3(112)

4-(4-bromophenyl)-N-(3-((2-chlorobenzoyl)amino)phenyl)-4-hydroxy-1-piperidinecarboxamide

EXAMPLE 3(113)

4-(4-bromophenyl)-4-hydroxy-N-(3-(octanoylamino)phenyl)-1-piperidinecarboxamide

EXAMPLE 3(114)

4-(4-bromophenyl)-4-hydroxy-N-(3-((3-phenylpropanoyl)amino)phenyl)-1-piperidinecarboxamide

EXAMPLE 3(115)

4-(4-bromophenyl)-4-hydroxy-N-(3-((3-methoxybenzoyl)amino)phenyl)-1-piperidinecarboxamide

EXAMPLE 3(116)

4-(4-bromophenyl)-4-hydroxy-N-(3-((2-thienylcarbonyl)amino)phenyl)-1-piperidinecarboxamide

EXAMPLE 3(117)

4-(4-bromophenyl)-4-hydroxy-N-(3-((4-(trifluoromethyl)benzoyl)amino)phenyl)-1-piperidinecarboxamide

EXAMPLE 3(118)

4-(4-bromophenyl)-4-hydroxy-N-(3-((2-phenoxypropanoyl)amino)phenyl)-1-piperidinecarboxamide

EXAMPLE 3(119)

4-(4-bromophenyl)-N-(3-((3,4-dichlorobenzoyl)amino)phenyl)-4-hydroxy-1-piperidinecarboxamide

EXAMPLE 3(120)

4-(4-bromophenyl)-N-(3-((2,4-difluorobenzoyl)amino)phenyl)-4-hydroxy-1-piperidinecarboxamide

EXAMPLE 3(121)

4-(4-bromophenyl)-N-(3-((2,5-difluorobenzoyl)amino)phenyl)-4-hydroxy-1-piperidinecarboxamide

EXAMPLE 3(122)

4-(4-bromophenyl)-N-(3-((2-ethoxybenzoyl)amino)phenyl)-4-hydroxy-1-piperidinecarboxamide

EXAMPLE 3(123)

4-(4-bromophenyl)-N-(3-((4-cyanobenzoyl)amino)phenyl)-4-hydroxy-1-piperidinecarboxamide

EXAMPLE 3(124)

4-(4-bromophenyl)-4-hydroxy-N-(3-((3,5,5-trimethylhexanoyl)amino)phenyl)-1-piperidinecarboxamide

EXAMPLE 3(125)

N-(3-(((4-(4-bromophenyl)-4-hydroxy-1-piperidinyl)carbonyl)amino)phenyl)-2-pyridinecarboxamide

EXAMPLE 3(126)

4-(4-bromophenyl)-N-(3-((2,3-difluorobenzoyl)amino)phenyl)-4-hydroxy-1-piperidinecarboxamide

EXAMPLE 3(127)

4-(4-bromophenyl)-N-(3-(((2,5-dimethoxyphenyl)acetyl)amino)phenyl)-4-hydroxy-1-piperidinecarboxamide

EXAMPLE 3(128)

4-(4-bromophenyl)-N-(3-(((3,4-dimethoxyphenyl)acetyl)amino)phenyl)-4-hydroxy-1-piperidinecarboxamide

EXAMPLE 3(129)

4-(4-bromophenyl)-N-(3-(((cyclobutylcarbonyl)amino)phenyl)-4-hydroxy-1-piperidinecarboxamide

EXAMPLE 3(130)

4-(4-bromophenyl)-N-(3-((2-fluoro-5-(trifluoromethyl)benzoyl)amino)phenyl)-4-hydroxy-1-piperidinecarboxamide

EXAMPLE 3(131)

4-(4-bromophenyl)-N-(3-((5-fluoro-2-(trifluoromethyl)benzoyl)amino)phenyl)-4-hydroxy-1-piperidinecarboxamide

EXAMPLE 3(132)

4-(4-bromophenyl)-N-(3-((3-fluoro-4-(trifluoromethyl)benzoyl)amino)phenyl)-4-hydroxy-1-piperidinecarboxamide

EXAMPLE 3(133)

4-(4-bromophenyl)-N-(3-((3,5-dimethoxybenzoyl)amino)phenyl)-4-hydroxy-1-piperidinecarboxamide

EXAMPLE 3(134)

4-(4-bromophenyl)-N-(3-((2-fluoro-3-(trifluoromethyl)benzoyl)amino)phenyl)-4-hydroxy-1-piperidinecarboxamide

EXAMPLE 3(135)

4-(4-bromophenyl)-N-(3-((4-fluoro-2-(trifluoromethyl)benzoyl)amino)phenyl)-4-hydroxy-1-piperidinecarboxamide

EXAMPLE 3(136)

4-(4-bromophenyl)-N-(3-((2-((difluoromethyl)thio)benzoyl)amino)phenyl)-4-hydroxy-1-piperidinecarboxamide

EXAMPLE 3(137)

4-(4-bromophenyl)-4-hydroxy-N-(3-((4-(trifluoromethoxy)benzoyl)amino)phenyl)-1-piperidinecarboxamide

EXAMPLE 3(138)

4-(4-bromophenyl)-N-(3-((2-chloro-5-fluorobenzoyl)amino)phenyl)-4-hydroxy-1-piperidinecarboxamide

EXAMPLE 3(139)

4-(4-bromophenyl)-N-(3-((2-fluoro-4-(trifluoromethyl)benzoyl)amino)phenyl)-4-hydroxy-1-piperidinecarboxamide

EXAMPLE 3(140)

4-(4-bromophenyl)-4-hydroxy-N-(3-((2-(trifluoromethoxy)benzoyl)amino)phenyl)-1-piperidinecarboxamide

EXAMPLE 3(141)

N-(3,5-dichlorophenyl)-4-hydroxy-4-isopropyl-1-piperidinecarboxamide

EXAMPLE 3(142)

methyl 3-(((4-(cyclohexylmethyl)-4-hydroxy-1-piperidinyl)carbonyl)amino)benzoate

EXAMPLE 3(143)

N-(3-bromophenyl)-4-(cyclohexylmethyl)-4-hydroxy-1-piperidinecarboxamide

EXAMPLE 3(144)

ethyl 3-(((4-(cyclohexylmethyl)-4-hydroxy-1-piperidinyl)carbonyl)amino)benzoate

EXAMPLE 3(145)

4-(cyclohexylmethyl)-4-hydroxy-N-(3-(methylthio)phenyl)-1-piperidinecarboxamide

EXAMPLE 3(146)

N-(3-chlorophenyl)-4-(cyclohexylmethyl)-4-hydroxy-1-piperidinecarboxamide

EXAMPLE 3(147)

4-(cyclohexylmethyl)-N-(3-ethylphenyl)-4-hydroxy-1-piperidinecarboxamide

EXAMPLE 3(148)

4-(cyclohexylmethyl)-4-hydroxy-N-(4-phenoxyphenyl)-1-piperidinecarboxamide

EXAMPLE 3(149)

4-(cyclohexylmethyl)-N-(3,5-dichlorophenyl)-4-hydroxy-1-piperidinecarboxamide

EXAMPLE 3(150)

4-(cyclohexylmethyl)-N-(3,4-dichlorophenyl)-4-hydroxy-1-piperidinecarboxamide

EXAMPLE 3(151)

N-(3-bromophenyl)-4-((ethylthio)methyl)-4-hydroxy-1-piperidinecarboxamide

EXAMPLE 3(152)

4-((ethylthio)methyl)-4-hydroxy-N-(3-methoxyphenyl)-1-piperidinecarboxamide

EXAMPLE 3(153)

4-((ethylthio)methyl)-4-hydroxy-N-(3-(trifluoromethyl)phenyl)-1-piperidinecarboxamide

EXAMPLE 3(154)

N-(3-chlorophenyl)-4-((ethylthio)methyl)-4-hydroxy-1-piperidinecarboxamide

EXAMPLE 3(155)

4-((ethylthio)methyl)-4-hydroxy-N-(3-methylphenyl)-1-piperidinecarboxamide

EXAMPLE 3(156)

N-(3-ethylphenyl)-4-((ethylthio)methyl)-4-hydroxy-1-piperidinecarboxamide

EXAMPLE 3(157)

4-((ethylthio)methyl)-N-(3-fluorophenyl)-4-hydroxy-1-piperidinecarboxamide

EXAMPLE 3(158)

4-((ethylthio)methyl)-4-hydroxy-N-(3-phenoxyphenyl)-1-piperidinecarboxamide

EXAMPLE 3(159)

4-((ethylthio)methyl)-4-hydroxy-N-(4-phenoxyphenyl)-1-piperidinecarboxamide

EXAMPLE 3(160)

N-(3,5-dimethylphenyl)-4-((ethylthio)methyl)-4-hydroxy-1-piperidinecarboxamide

EXAMPLE 3(161)

N-(2,6-dichloro-4-pyridinyl)-4-((ethylthio)methyl)-4-hydroxy-1-piperidinecarboxamide

EXAMPLE 3(162)

N-(3-bromophenyl)-4-tert-butyl-4-hydroxy-1-piperidinecarboxamide

EXAMPLE 3(163)

ethyl 3-(((4-tert-butyl-4-hydroxy-1-piperidinyl)carbonyl)amino)benzoate

EXAMPLE 3(164)

4-tert-butyl-4-hydroxy-N-(3-(trifluoromethyl)phenyl)-1-piperidinecarboxamide

EXAMPLE 3(165)

4-tert-butyl-4-hydroxy-N-(3-(methylthio)phenyl)-1-piperidinecarboxamide

EXAMPLE 3(166)

4-tert-butyl-N-(3-chlorophenyl)-4-hydroxy-1-piperidinecarboxamide

EXAMPLE 3(167)

4-tert-butyl-4-hydroxy-N-(3-methylphenyl)-1-piperidinecarboxamide

EXAMPLE 3(168)

4-tert-butyl-N-(3-ethylphenyl)-4-hydroxy-1-piperidinecarboxamide

EXAMPLE 3(169)

4-tert-butyl-4-hydroxy-N-(4-phenoxyphenyl)-1-piperidinecarboxamide

EXAMPLE 3(170)

4-tert-butyl-N-(3,5-dichlorophenyl)-4-hydroxy-1-piperidinecarboxamide

EXAMPLE 3(171)

4-tert-butyl-N-(3,5-dimethylphenyl)-4-hydroxy-1-piperidinecarboxamide

EXAMPLE 3(172)

4-tert-butyl-N-(3,4-dichlorophenyl)-4-hydroxy-1-piperidinecarboxamide

EXAMPLE 3(173)

methyl 3-(((4-cyclopentyl-4-hydroxy-1-piperidinyl)carbonyl)amino)benzoate

EXAMPLE 3(174)

4-cyclopentyl-4-hydroxy-N-(3-methoxyphenyl)-1-piperidinecarboxamide

EXAMPLE 3(175)

N-(3-cyanophenyl)-4-cyclopentyl-4-hydroxy-1-piperidinecarboxamide

EXAMPLE 3(176)

ethyl 3-(((4-cyclopentyl-4-hydroxy-1-piperidinyl)carbonyl)amino)benzoate

EXAMPLE 3(177)

4-cyclopentyl-4-hydroxy-N-(3-(methylthio)phenyl)-1-piperidinecarboxamide

EXAMPLE 3(178)

4-cyclopentyl-4-hydroxy-N-(3-methylphenyl)-1-piperidinecarboxamide

EXAMPLE 3(179)

4-cyclopentyl-N-(3-fluorophenyl)-4-hydroxy-1-piperidinecarboxamide

EXAMPLE 3(180)

4-cyclopentyl-4-hydroxy-N-(4-phenoxyphenyl)-1-piperidinecarboxamide

EXAMPLE 3(181)

4-cyclopentyl-4-hydroxy-N-(4-(trifluoromethyl)phenyl)-1-piperidinecarboxamide

EXAMPLE 3(182)

4-cyclopentyl-N-(3,5-difluorophenyl)-4-hydroxy-1-piperidinecarboxamide

EXAMPLE 3(183)

N-(3-bromophenyl)-4-hydroxy-4-(5-methyl-2-pyridinyl)-1-piperidinecarboxamide

EXAMPLE 3(184)

4-hydroxy-N-(3-methoxyphenyl)-4-(5-methyl-2-pyridinyl)-1-piperidinecarboxamide

EXAMPLE 3(185)

N-(3-cyanophenyl)-4-hydroxy-4-(5-methyl-2-pyridinyl)-1-piperidinecarboxamide

EXAMPLE 3(186)

4-hydroxy-4-(5-methyl-2-pyridinyl)-N-(3-(trifluoromethyl)phenyl)-1-piperidinecarboxamide

EXAMPLE 3(187)

N-(3-ethylphenyl)-4-hydroxy-4-(5-methyl-2-pyridinyl)-1-piperidinecarboxamide

EXAMPLE 3(188)

N-(3-fluorophenyl)-4-hydroxy-4-(5-methyl-2-pyridinyl)-1-piperidinecarboxamide

EXAMPLE 3(189)

4-hydroxy-4-(5-methyl-2-pyridinyl)-N-(4-phenoxyphenyl)-1-piperidinecarboxamide

EXAMPLE 3(190)

N-(3,5-dimethylphenyl)-4-hydroxy-4-(5-methyl-2-pyridinyl)-1-piperidinecarboxamide

EXAMPLE 3(191)

N-(3,4-dichlorophenyl)-4-hydroxy-4-(5-methyl-2-pyridinyl)-1-piperidinecarboxamide

EXAMPLE 3(192)

N-(2,6-dichloro-4-pyridinyl)-4-hydroxy-4-(5-methyl-2-pyridinyl)-1-piperidinecarboxamide

EXAMPLE 3(193)

N-(3,5-dichlorophenyl)-4-hydroxy-4-(diethylaminocarbonyl)-1-piperidinecarboxamide

EXAMPLE 3(194)

N-(3,5-dichlorophenyl)-4-hydroxy-4-(1-piperidinylcarbonyl)-1-piperidinecarboxamide

EXAMPLE 3(195)

4-benzyl-N-(3,5-bis(trifluoromethyl)phenyl)-4-hydroxy-1-piperidinecarboxamide

EXAMPLE 3(196)

N-(3,5-bis(trifluoromethyl)phenyl)-4-(4-chloro-3-(trifluoromethyl)phenyl)-4-hydroxy-1-piperidinecarboxamide

EXAMPLE 3(197)

N-(3,5-bis(trifluoromethyl)phenyl)-4-tert-butyl-4-hydroxy-1-piperidinecarboxamide

EXAMPLE 3(198)

N-(3,5-bis(trifluoromethyl)phenyl)-4-((ethylthio)methyl)-4-hydroxy-1-piperidinecarboxamide

EXAMPLE 3(199)

4-benzyl-4-hydroxy-N-(3-(trifluoromethyl)phenyl)-1-piperidinecarboxamide

EXAMPLE 3(200)

4-benzyl-N-(3,5-dichlorophenyl)-4-hydroxy-1-piperidinecarboxamide

EXAMPLE 3(201)

N-(3-chlorophenyl)-4-hydroxy-4-(3-methylbutyl)-1-piperidinecarboxamide

EXAMPLE 3(202)

4-cyclopropyl-4-hydroxy-N-(3-(trifluoromethyl)phenyl)-1-piperidinecarboxamide

EXAMPLE 3(203)

N-(3-chlorophenyl)-4-cyclobutyl-4-hydroxy-1-piperidinecarboxamide

EXAMPLE 3(204)

4-cyclobutyl-4-hydroxy-N-(4-phenoxyphenyl)-1-piperidinecarboxamide

EXAMPLE 3(205)

4-hydroxy-4-(2-naphthyl)-N-(3-phenoxyphenyl)-1-piperidinecarboxamide

EXAMPLE 3(206)

N-(3-chlorophenyl)-4-hydroxy-4-(2-naphthyl)-1-piperidinecarboxamide

EXAMPLE 3(207)

4-hydroxy-4-(1-naphthyl)-N-(3-phenoxyphenyl)-1-piperidinecarboxamide

EXAMPLE 3(208)

4-hydroxy-4-(1-naphthyl)-N-(3-(trifluoromethyl)phenyl)-1-piperidinecarboxamide

EXAMPLE 3(209)

N-(3,5-dichlorophenyl)-4-hydroxy-4-(1-naphthyl)-1-piperidinecarboxamide

EXAMPLE 3(210)

N-(3-fluoro-5-(trifluoromethyl)phenyl)-4-hydroxy-4-(5-methyl-2-pyridinyl)-1-piperidinecarboxamide

EXAMPLE 3(211)

N-(3-fluoro-5-(trifluoromethyl)phenyl)-4-hydroxy-4-(3-(trifluoromethyl)phenyl)-1-piperidinecarboxamide

EXAMPLE 3(212)

N-(3-fluoro-5-(trifluoromethyl)phenyl)-4-hydroxy-4-(2-naphthyl)-1-piperidinecarboxamide

EXAMPLE 3(213)

4-((ethylthio)methyl)-N-(3-fluoro-5-(trifluoromethyl)phenyl)-4-hydroxy-1-piperidinecarboxamide

EXAMPLE 3(214)

N-(3-(cyclopentyloxy)phenyl)-4-hydroxy-4-phenyl-1-piperidinecarboxamide

EXAMPLE 3(215)

4-(4-bromophenyl)-N-(3-(cyclopentyloxy)phenyl)-4-hydroxy-1-piperidinecarboxamide

EXAMPLE 3(216)

N-(3-(cyclopentyloxy)phenyl)-4-(4-fluorophenyl)-4-hydroxy-1-piperidinecarboxamide

EXAMPLE 3(217)

4-cyclobutyl-N-(3-(cyclopentyloxy)phenyl)-4-hydroxy-1-piperidinecarboxamide

EXAMPLE 3(218)

4-cyclopentyl-N-(3-(cyclopentyloxy)phenyl)-4-hydroxy-1-piperidinecarboxamide

EXAMPLE 3(219)

4-tert-butyl-N-(3-(cyclopentyloxy)phenyl)-4-hydroxy-1-piperidinecarboxamide

EXAMPLE 3(220)

4-butyl-N-(3-(cyclopentyloxy)phenyl)-4-hydroxy-1-piperidinecarboxamide

EXAMPLE 3(221)

4-(cyclopentylmethyl)-N-(3-(cyclopentyloxy)phenyl)-4-hydroxy-1-piperidinecarboxamide

EXAMPLE 3(222)

N-(3-(cyclopentyloxy)phenyl)-4-hydroxy-4-(1-propylbutyl)-1-piperidinecarboxamide

EXAMPLE 3(223)

N-(3-(cyclohexyloxy)phenyl)-4-hydroxy-4-(1-propylbutyl)-1-piperidinecarboxamide

EXAMPLE 3(224)

4-hydroxy-4-(1-propylbutyl)-N-(3-(trifluoromethyl)phenyl)-1-piperidinecarboxamide

EXAMPLE 3(225)

N-(3,5-bis(trifluoromethyl)phenyl)-4-hydroxy-4-(1-propylbutyl)-1-piperidinecarboxamide

EXAMPLE 3(226)

N-(3-(cyclopentyloxy)phenyl)-4-hydroxy-4-(3-methylphenyl)-1-piperidinecarboxamide

EXAMPLE 3(227)

N-(3-(cyclopentyloxy)phenyl)-4-hydroxy-4-(4-methylphenyl)-1-piperidinecarboxamide

EXAMPLE 3(228)

N-(3-(cyclohexyloxy)phenyl)-4-hydroxy-4-(4-methylphenyl)-1-piperidinecarboxamide

EXAMPLE 3(229)

N-(3-chloro-5-fluorophenyl)-4-hydroxy-4-(5-methyl-2-pyridinyl)-1-piperidinecarboxamide

EXAMPLE 3(230)

N-(3-chloro-5-fluorophenyl)-4-hydroxy-4-(2-methylphenyl)-1-piperidinecarboxamide

EXAMPLE 3(231)

N-(3-chloro-5-fluorophenyl)-4-cyclopropyl-4-hydroxy-1-piperidinecarboxamide

EXAMPLE 3(232)

N-(3-chloro-5-fluorophenyl)-4-hydroxy-4-(1-naphthyl)-1-piperidinecarboxamide

EXAMPLE 3(233)

4-phenyl-N-(3-(trifluoromethyl)phenyl)-1-piperidinecarboxamide

EXAMPLE 3(234)

4-(4-bromophenyl)-N-(2,6-dichloro-4-pyridinyl)-4-hydroxy-1-piperidinecarboxamide

EXAMPLE 3(235)

4-(4-bromophenyl)-1-((3-(trifluoromethyl)phenyl)
acetyl)-4-piperidinol

EXAMPLE 3(236)

4-(4-bromophenyl)-4-hydroxy-N-(3-(trifluoromethyl)phenyl)-1-piperidinecarbothioamide

EXAMPLE 3(237)

N-(3,5-dichlorophenyl)-4-hydroxy-4-(5-methyl-2-pyridinyl)-1-piperidinecarboxamide

EXAMPLE 3(238)

N-(3,5-dichlorophenyl)-4-hydroxy-4-(6-methoxy-2-pyridinyl)-1-piperidinecarboxamide

EXAMPLE 3(239)

N-(3,5-dichlorophenyl)-4-(ethoxymethyl)-4-hydroxy-1-piperidinecarboxamide

EXAMPLE 3(240)

4-(butoxymethyl)-N-(3,5-dichlorophenyl)-4-hydroxy-1-piperidinecarboxamide

EXAMPLE 3(241)

4-((benzyloxy)methyl)-N-(3,5-dichlorophenyl)-4-hydroxy-1-piperidinecarboxamide

EXAMPLE 3(242)

N-(3,5-dichlorophenyl)-4-hydroxy-4-(isopropoxymethyl)-1-piperidinecarboxamide

EXAMPLE 3(243)

4-hydroxy-4-pentyl-N-(3-phenoxyphenyl)-1-piperidinecarboxamide

EXAMPLE 3(244)

4-hexyl-4-hydroxy-N-(3-phenoxyphenyl)-1-piperidinecarboxamide

EXAMPLE 3(245)

N-(3,5-dichlorophenyl)-4-hexyl-4-hydroxy-1-piperidinecarboxamide

EXAMPLE 3(246)

N-(2,6-dichloro-4-pyridinyl)-4-hexyl-4-hydroxy-1-piperidinecarboxamide

EXAMPLE 3(247)

4-hydroxy-N-(3-phenoxyphenyl)-4-propyl-1-piperidinecarboxamide

EXAMPLE 3(248)

4-(4-bromophenyl)-4-hydroxy-N-(3-nitrophenyl)-1-piperidinecarboxamide

EXAMPLE 3(249)

ethyl 3-(((4-(4-bromophenyl)-4-hydroxy-1-piperidinyl)carbonyl)amino)benzoate

EXAMPLE (250)

4-butyl-4-hydroxy-N-(3-(trifluoromethoxy)phenyl)-1-piperidinecarboxamide

EXAMPLE 3(251)

N-(3-benzoylphenyl)-4-butyl-4-hydroxy-1-piperidinecarboxamide

EXAMPLE 3(252)

4-(4-bromophenyl)-4-hydroxy-N-(3-vinylphenyl)-1-piperidinecarboxamide

EXAMPLE 3(253)

N-(3-benzoylphenyl)-4-(4-bromophenyl)-4-hydroxy-1-piperidinecarboxamide

EXAMPLE 3(254)

4-(4-bromophenyl)-4-hydroxy-N-(3-(phenoxymethyl)phenyl)-1-piperidinecarboxamide

EXAMPLE 3(255)

N-(3-(benzyloxy)phenyl)-4-butyl-4-hydroxy-1-piperidinecarboxamide

EXAMPLE 3(256)

N-(3-(benzyloxy)phenyl)-4-(4-bromophenyl)-4-hydroxy-1-piperidinecarboxamide

EXAMPLE 3(257)

4-(4-bromophenyl)-4-hydroxy-N-(3-((phenylsulfonyl)amino)phenyl)-1-piperidinecarboxamide

EXAMPLE 3(258)

4-butyl-4-hydroxy-N-(3-(phenoxymethyl)phenyl)-1-piperidinecarboxamide

EXAMPLE 3(259)

4-hydroxy-4-(5-methyl-2-pyridinyl)-N-(3-phenoxyphenyl)-1-piperidinecarboxamide

EXAMPLE 3(260)

4-hydroxy-4-(2-naphthyl)-N-(3-(trifluoromethyl)phenyl)-1-piperidinecarboxamide

EXAMPLE 3(261)

4-sec-butyl-4-hydroxy-N-(3-(trifluoromethyl)phenyl)-1-piperidinecarboxamide

EXAMPLE 3(262)

4-hydroxy-4-(1-methylbutyl)-N-(3-(trifluoromethyl)phenyl)-1-piperidinecarboxamide

EXAMPLE 3(263)

N-(3,5-dimethylphenyl)-3-(4-(4-(trifluoromethoxy)phenyl)-1-piperazinyl)-1-azetidinecarboxamide

EXAMPLE 3(264)

3-(4-(4-(trifluoromethoxy)phenyl)-1-piperazinyl)-N-(3-(trifluoromethyl)phenyl)-1-azetidinecarboxamide

BIOLOGICAL EXAMPLE 1

Evaluation of Antagonistic Activity for EDG-5 by Monitoring Concentration Change of Intracellular Calcium Ion Chinese hamster ovary (CHO) cells overexpressed human EDG-5 gene were cultured in Ham's F12 medium (GIBCO BRL) containing 10% FBS (fetal bovine serum), penicillin/streptomycin, and blasticidin (5 μg/ml). Cultured cells were incubated in a Fura2 (5 μM)-AM solution [Ham's F12 medium containing FBS (10%), HEPES buffer (20 mM, pH7.4), and probenecid (2.5 mM)] at 37° C. for 60 minutes. Then they were washed once with a Hank's solution (2.5 mM) containing probenecid and immersed into the same solution. A plate was set on a fluorescent drug screening system, and the concentration of intracellular calcium ion was measured for 30 seconds with no stimulation. A solution of a compound (dimethyl sulfoxide (DMSO) solution of 1 nM to 10 μM at the final concentration) to be tested was added. After lapse of 5 minutes, S1P (final concentration: 100 nM) was added, the concentration of intracellular calcium ion before and after the addition was measured every 3 seconds (excitation wave length: 340 nm and 380 nm; fluorescent wave length: 500 nm).

The antagonistic activity for EDG-5 was calculated as an inhibition rate (%) by the following equation, wherein the peak value of S1P (final concentration: 100 nM) in a well into which DMSO instead of compound was added was regarded as a control value (A), and in the cells treated with the compound the difference value (B) between the value before addition of the compound and that after the addition was obtained and compared with the control value.

Inhibition rate (%)=$((A-B)/A) \times 100$

In addition, the evaluation of antagonist for EDG-1 and EDG-3 was carried out using cells which overexpressed human EDG-1 or EDG-3 and using the above mentioned method.

As a result, the compound of the present invention showed specifically antagonistic activity for EDG-5 at under 10 μM. For example, the IC50 value of N-(1H-1,3-dimethyl-4-isopropylpyrazolo[3,4-b]pyridin-6-yl)amino-N'-(3,5-dichloropyridin-4-yl)urea (hereinafter, referred to as compound 1) is 0.5 μM for EDG-5 and above 10 μM for EDG-1 and EDG-3. In addition, the IC50 value of 4-(4-bromophenyl)-4-hydroxy-N-(3-(trifluoromethyl)phenyl)-1-piperidinecarboxamide (the compound described in Example 1(57), hereinafter, referred to as compound 2) is 0.4 μM for EDG-5 and above 10 μM for EDG-1 and EDG-3.

BIOLOGICAL EXAMPLE 2

The Inhibitory Activity for EDG-5 Antagonist of Vasoconstrictor Action of Canine Removed Basilar Artery by S1P The removed basilar arteries of euthanized male beagle (12 months old) was immersed in Krebs-Henseleit solution [112 mmol/L sodium chloride, 5.9 mmol/L potassium chloride, 2.0 mmol/L calcium chloride, 1.2 mmol/L magnesium chloride, 1.2 mmol/L monobasic sodium phosphate, 25.0 mmol/L sodium hydrogen carbonate $NaHCO_3$, 11.5 mmol/L glucose, saturated by mixed gas (95% $O_2$+5% $CO_2$)]. They were divided by 3-4 mm with ophthalmic scissors and made as ringed samples. Made ringed tissues were hung in magnus tube (volume: 10 mL) filled with Krebs-Henseleit solution [37±1° C., aerated with mixed gas (95% $O_2$+5% $CO_2$)] using a hook. Next, they were loaded with 1 g resting tension stabilized for about 60 minutes, then constrictive movement was recorded on a recorder through strain compression amplifier (AP-601G, Nihon Kohden) from Force displacement transducer (FD pickup TB-611T). Serotonin (1 μM) is used as positive control for constriction action. After that, S1P (10 μM) adding, vasoconstrictive action was measured. As a result, serotonin and S1P constricted basilar arteries.

Figure 2:
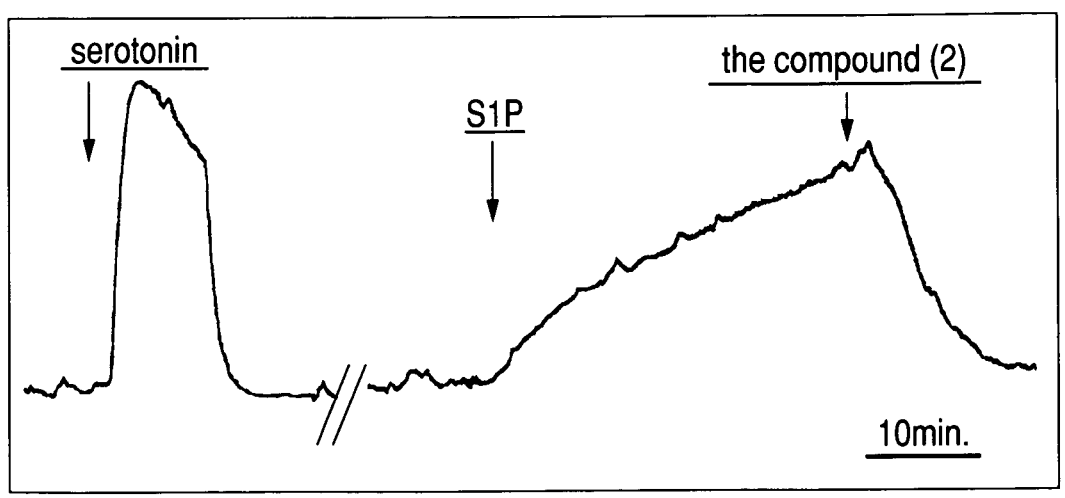
FIG. 2 is a graph showing the suppression of vasoconstrictor action of canine removed basilar artery by S1P by 10 μM of the compound (2) of the present invention.

After 20 minutes S1P adding, test compounds (each 10 μM of compound (1) and compound (2) described in above mentioned Biological Example 1) added and we examined inhibitory effect on vasoconstrictive action by S1P. As a result, test compounds having EDG-5 antagonist activity inhibited vasoconstrictive action by S1P. On the other hand, test compounds having EDG-1 and/or EDG-3 did not show inhibitory effect. The results show FIG. 1 and FIG. 2.

In addition, the compounds except compound (1) and compound (2) having EDG-5 antagonist activity showed vasoconstrictive inhibitory effect as same effect as compound (1) and compound (2). Further, compound (1) and compound (2) showed inhibitory effect on rabbit vasoconstrictive action by S1P.

BIOLOGICAL EXAMPLE 3

Figure 3:
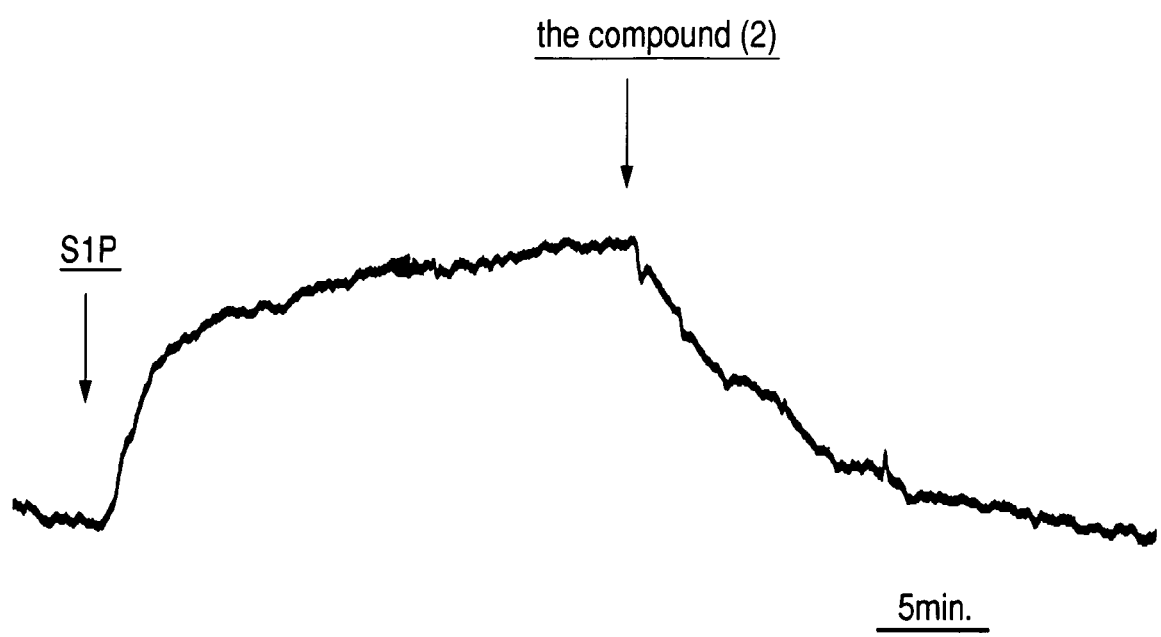
FIG. 3 is a graph showing the suppression of vasoconstrictor action of rat removed basilar artery by S1P by 3 μM of the compound (2) of the present invention.
Figure 4:
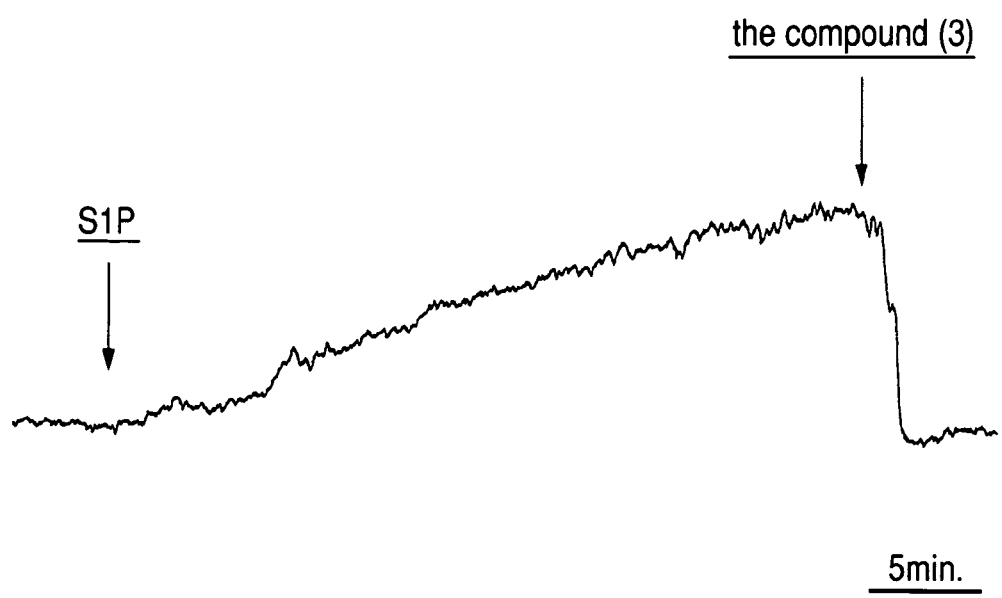
FIG. 4 is a graph showing the suppression of vasoconstrictor action of rat removed basilar artery by S1P by 3 μM of the compound (3) of the present invention.

Effect of EDG-5 Antagonist on Vasoconstrictor Action of Rat Removed Basilar Artery Basilar arteries were removed from male rat (CD(SD)IGS, male, Charles River Japan, Inc., 8 weeks old-10 weeks old, 350-450 g) and quickly immersed in cooled Krebs-Henseleit solution. Removed basilar arteries were divided by about 3 mm width with ophthalmic scissors and made as ringed samples. Samples hung in micro tissue organ bath (MTOB-1: Preimetech Corp.) filled with Krebs-Henseleit solution (37° C.). They were loaded with about 0.2 g resting tension stabilized for about 60 minutes, and then constrictive movement was recorded on a recorder (linearcoda WR3320: Graphtec Corp.) through strain compression amplifier (AP-601G, Nihon Kohden) from micro tissue organ bath. As a result of examination of effect of compound (2) and N-(2,6-dichloro-4-piridinyl)-2-(4-isopropyl-1,3-dimethyl-1H-pyrazolo[3,4-b]pyridin-6-yl)hydrazinecarboxamide (hereinafter referred to as compound (3)), we confirmed inhibitory effect of same compounds. The results show FIG. 3 and FIG. 4.

BIOLOGICAL EXAMPLE 4

Figure 5:
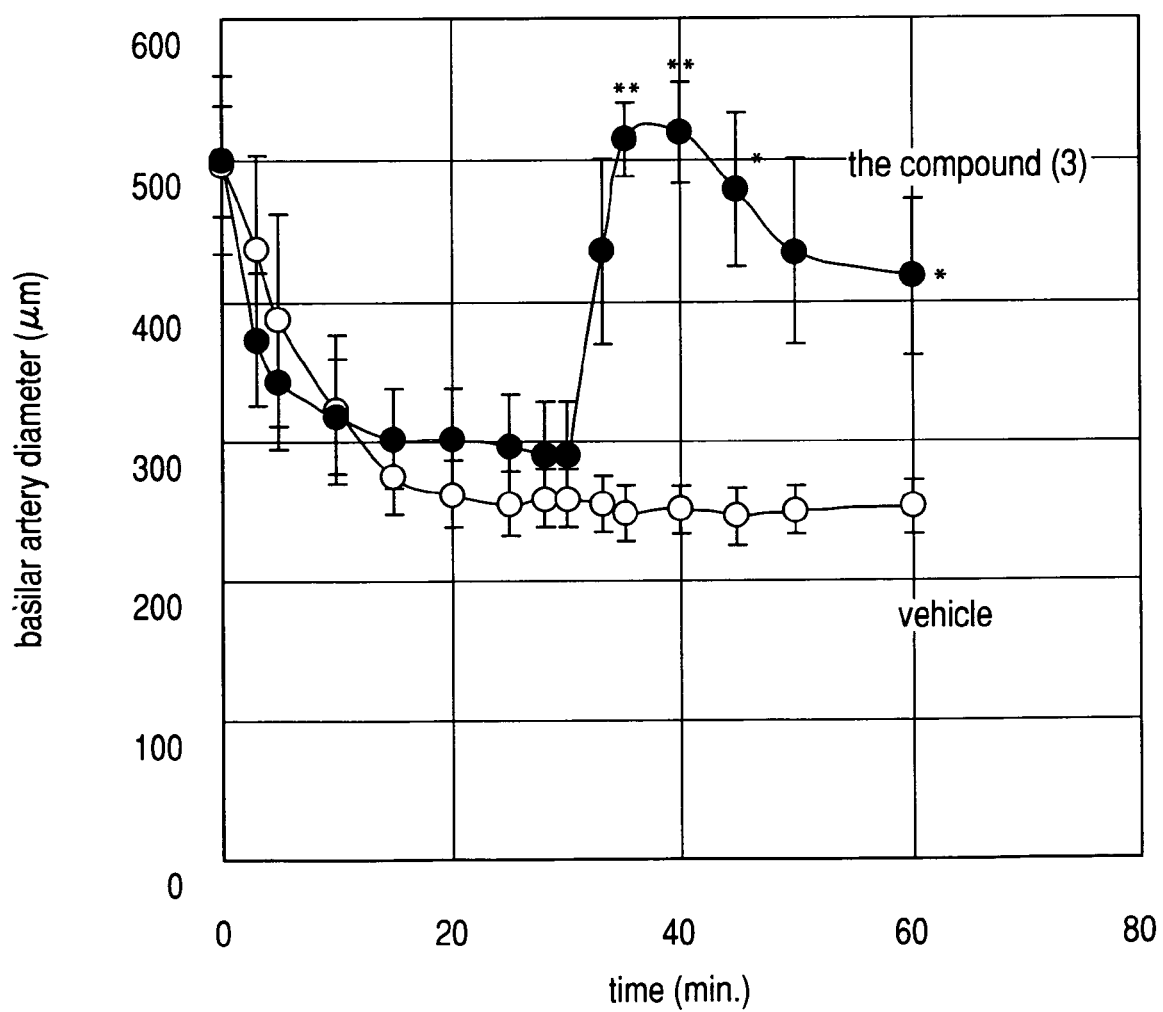
FIG. 5 is a graph showing the suppression of vasoconstrictor action of rat removed basilar artery by S1P by the compound (3) of the present invention.

Effect of EDG-5 Antagonist in Measurement System of Vasoconstrictor Action of Rat Basilar Artery Induced by S1P Rat (CD(SD)IGS, male, Charles River Japan Inc., 11 weeks old-13 weeks old, 400-550 g) was anesthetized by injection of urethane (1.2 g/kg, s.c.), incised scalp of occipital for administration of S1P into cisterna and then fixed to dorsal position. Rat was inserted into trachea with catheter and then, cut down with esophagus, and skull at the base of brain was exposed. Under the stereomicroscope, craniotomy was carefully operated with electric drill and scorper forceps. We made basilar artery expose, and it was done in the condition which arachnoid was left, and coating on basilar artery was exfoliated, and could be observed. Observation and image capture of basilar artery were performed using the stereomicroscope (Olympus Optics Inc., SZH-10) and charge-coupled device (CCD) camera (FUJIFILM, HC-2500) connected with it. Macscope (MITANI Corp.) was used as an Image capture software. Before administration of S1P into cisterna, shooting around basilar artery was performed more than three times and we confirmed that length of diameter was constant. Vasoconstrictor action of basilar artery was induced by administration of S1P into cisterna. After 30 minutes administration of S1P, compound (3) (10 μg/100 μL/rat, i.c.) was administered. Shooting of basilar artery was performed at 3, 5, 10, 15, 20, 25, 28, 30, 33, 35, 40, 45, 50, 60 minutes after administration of S1P into cisterna. Diameter of basilar artery was measured by selecting from an area having no branch in the center of basilar artery. The diameter was calculated by comparing with the length of micrometer (0.2 mm, 0.01 mm scale) shooted in the same condition. Adobe Photoshop (Version 5.0J) was used for analysis. The diameter of basilar artery (pre-value, 0 min) before S1P administration used mean for shooting three times. The calculation of percentage of basilar artery diameter was calculated by dividing diameter after the S1P administration by a pre-value. The t-test was used for statistical test (*:$p<0.05$, :$p<0.01$ vs. vehicle). The results show FIG. 5**. The compound (3) inhibited vasoconstrictor action of basilar artery by S1P.

BIOLOGICAL EXAMPLE 5

Figure 6:
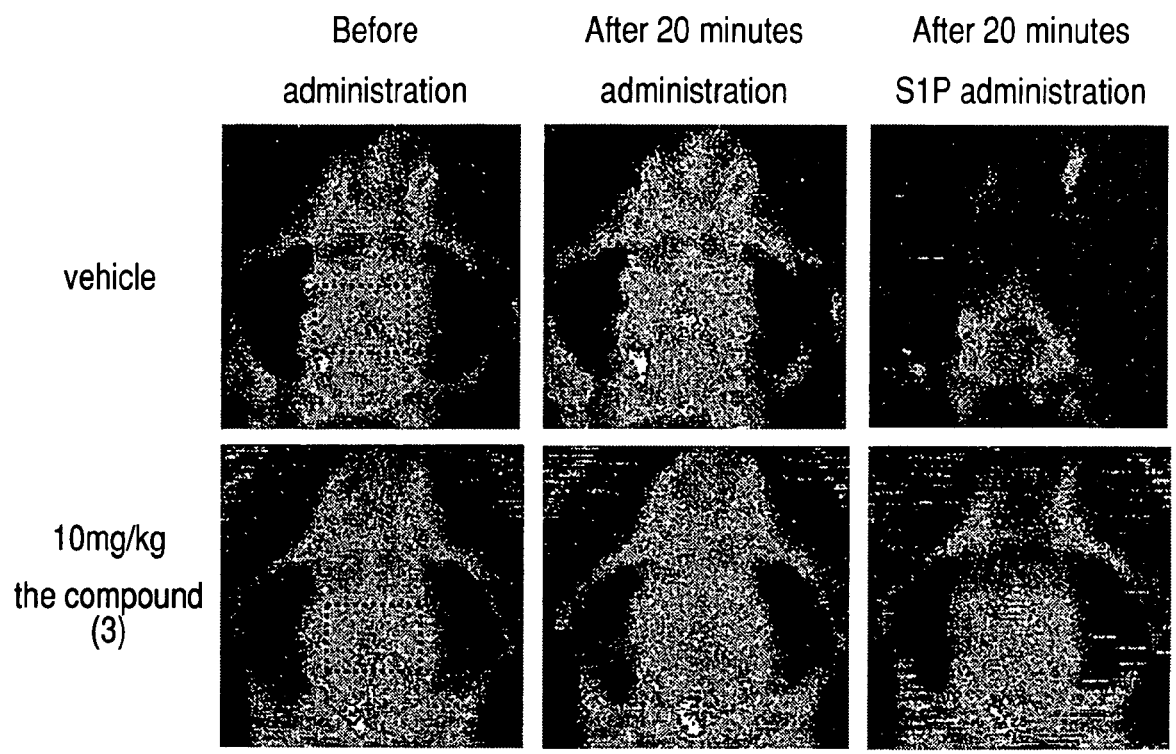
FIG. 6 is a photograph showing the suppression of degradation of rat dural blood flow by S1P by the compound (3) of the present invention.

Effect of EDG-5 Antagonist in Measurement System of Decrease of Dural Blood Flow Induced by S1P Rat (CD(SD)IGS, male, Charles River Japan Inc., 10 weeks old-13 weeks old, 450-520 g) was anesthetized by injection of urethane (1.2 g/kg, s.c.), placed in the femoral vein with catheter (polyethylene tube SP10; I.D. 0.28 mm, O.D. 0.61 mm: Natsume Seisakusho Co. Ltd.) for compounds administration, and then blood flow to brain through only vertebral artery was made to happen by tying both sides of common carotid arteries. Next, the scalp was cut open and the head region was exposed in order to measure dural blood flow and administer into cisterna. In addition, the trachea was placed with catheter (polyethylene tube; size 7.9: Hibiki) and it connected to the artificial respirator. The measurement of dural blood flow was performed to transmit with 1a ser light to skull using Moon Laser Doppler Imager (Moor LDI) [about 11cm distant from measuring object, about 150 dots both of XY measurement resolution, scanning about 2.8×2.8 cm area (150dots/2.8 cm)]. In addition, measurement condition involved in flux calculation (FLUX; relative value) such as sensitivity -gain etc., was integrated within all experiment. The images of blood flow were captured through the capture software, moor LDI Measurement V3.08, and image data was treated with analyzed software, moor LDI Image Processing V3.08. Blood flow was stabilized by administration through femoral vein at dosage of 10 mg/kg of compound (3) or with vehicle (0.1% (v/v) DMSO/rat plasma). And then, S1P was administered into cisterna and in succession blood flow measurement was performed. The dosage of S1P was 300 μg/kg and the dosage capacity was 100 μL/rat. Measurement was performed before administration of vehicle or compound (3), after 20 minutes administration of vehicle or compound (3) and after 20 minutes administration of S1P. The results show FIG. 6. The compound (3) inhibited decrease of dural blood flow by S1P.

BIOLOGICAL EXAMPLE 6

Inhibitory Effect of EDG-5 Antagonist in Measurement System of Vasoconstrictor Action of Canine Renal Artery by S1P The removed renal arteries of euthanized male beagle (12 months old) was immersed in Krebs-Henseleit solution [112 mmol/L sodium chloride, 5.9 mmol/L potassium chloride, 2.0 mmol/L calcium chloride, 1.2 mmol/L magnesium chloride, 1.2 mmol/L monobasic sodium phosphate, 25.0 mmol/L sodium hydrogen carbonate $NaHCO_3$, 11.5 mmol/L glucose, saturated by mixed gas (95% $O_2$+5% $CO_2$)]. They were divided by 3-4 mm with ophthalmic scissors and made as ringed samples. Made ringed tissues were hung in magnus tube (volume: 10 mL) filled with Krebs-Henseleit solution [37±1° C., aerated with mixed gas (95% $O_2$+5% $CO_2$)] using a hook. Next, they were loaded with 1 g resting tension stabilized for about 60 minutes, then constrictive movement was recorded on a recorder through strain compression amplifier (AP-601G, Nihon Kohden) from Force displacement transducer (FD pickup TB-611T). Serotonin (1 μM) is used as positive control for constriction action. After that, S1P (10 μM) adding, vasoconstrictive action was measured. As a result, serotonin and S1P constricted renal arteries.

Figure 7:
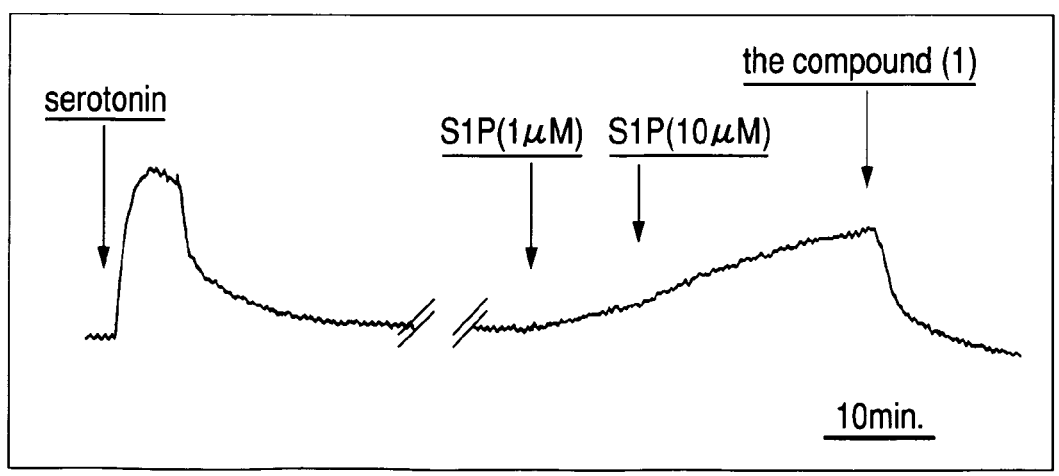
FIG. 7 is a graph showing the suppression of vasoconstrictor action of canine removed renal artery by S1P by 10 μM of the compound (1) of the present invention.
Figure 8:
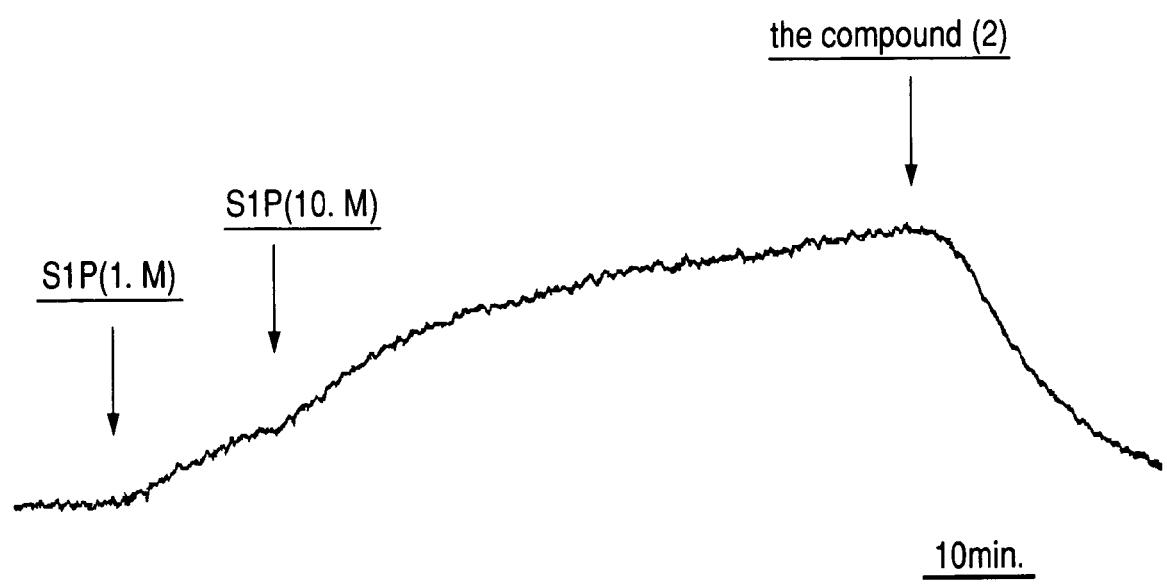
FIG. 8 is a graph showing the suppression of vasoconstrictor action of canine removed renal artery by S1P by 10 μM of the compound (2) of the present invention.

After 40 minutes S1P (1 μM) adding, test compounds (each 10 μM of compound (1) and compound (2) added and we examined inhibitory effect on vasoconstrictive action by S1P. As a result, test compounds having EDG-5 antagonist activity inhibited vasoconstrictive action of renal arteries by S1P. On the other hand, test compounds having EDG-1 and/or EDG-3 did not show inhibitory effect. The results show FIG. 7 and FIG. 8.

In addition, the compounds except the above mentioned compounds showed vasoconstrictive inhibitory effect as same effect. Further, the above mentioned compounds showed inhibitory effect on rabbit vasoconstrictive action of renal artery by S1P.

The removed thoracic aorta of euthanized SD rat (7-13 weeks old) was immersed in Krebs-Henseleit solution [112 mmol/L sodium chloride, 5.9 mmol/L potassium chloride, 2.0 mmol/L calcium chloride, 1.2 mmol/L magnesium chloride, 1.2 mmol/L monobasic sodium phosphate, 25.0 mmol/L sodium hydrogen carbonate $NaHCO_3$, 11.5 mmol/L glucose, saturated by mixed gas (95% $O_2$+5% $CO_2$)]. They were divided by 3-4 mm with ophthalmic scissors and made as vortical samples. Made samples were hung in magnus tube (volume: 10 mL) filled with Krebs-Henseleit solution [37±1° C., aerated with mixed gas (95% $O_2$+5% $CO_2$)] using a hook. Next, they were loaded with 0.5 g resting tension stabilized for about 60 minutes, then constrictive movement was recorded on a recorder through strain compression amplifier (AP-601G, Nihon Kohden) from Force displacement transducer (FD pickup TB-611T). Sympathetic nerve stimulant, phenylephrine, (10 μM) is used as positive control for constriction action. After that, S1P (10 μM) adding, vasoconstrictive action was measured. As a result, phenylephrine and S1P constricted rat thoracic aorta.

Figure 9:
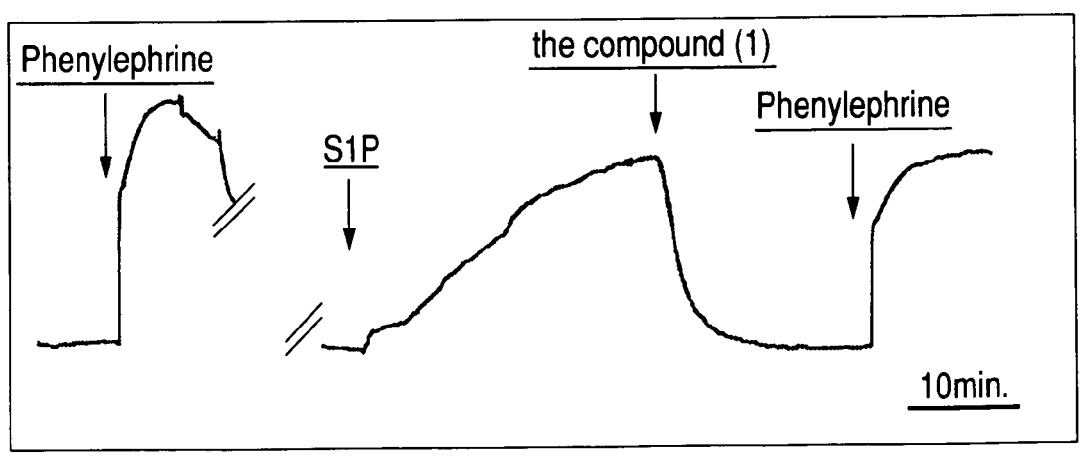
FIG. 9 is a graph showing the suppression of vasoconstrictor action of rat removed thoracic aorta by S1P by 10 μM of the compound (1) of the present invention and not showing the suppression of vasoconstrictor action of rat removed thoracic aorta by phenylephrine.

After an hour S1P adding, test compounds [10 μM of compound (1)] added and we examined inhibitory effect on vasoconstrictive action by S1P. As a result, test compounds having EDG-5 antagonist activity did not inhibit vasoconstrictive action of thoracic aorta by phenylephrine but specifically inhibited vasoconstrictive action of thoracic aorta by S1P. On the other hand, test compounds having EDG-1 and/or EDG-3 did not show inhibit vasoconstrictive action by phenylephrine and S1P. The results show FIG. 9.

In addition, the compounds having EDG-5 antagonist activity except the compound (1) showed vasoconstrictive inhibitory effect as same effect as the compound (1). Further, the compounds (1) showed inhibitory effect on vasoconstrictive action of rabbit and canine thoracic aorta by S1P.

BIOLOGICAL EXAMPLE 8

EDG-5 Antagonist Activity on Increase of Rat Blood Pressure by S1P

Male SD Rat (8 weeks old-10 weeks old) was anesthetized by injection of pentobarbital sodium (50 mg/mL/kg), after midline incision in the cervical region, trachea was exposed by exfoliation of tracheal muscle layer and cannula made of polyethylene was inserted into trachea. Next, catheter made of polyethylene was inserted into the common carotid artery and the common jugular vein. Catheter inserted into the common carotid artery was connected to the piezotransducer and the blood pressure was recorded on the recorder through strain compression amplifier. After the above mentioned operation was finished, in the case of the spinal chord was broken, the spinal chord was broken by insertion of stainless pole into the spinal chord cavity. After the spinal chord was broken, tracheal cannula was immediately connected into the artificial breathing device for small animals and artificial ventilation was performed under the conditions of a ventilatory volume 6 mL/kg and velocity 60 times/min. After then, S1P was administered and we confirmed blood pressure was increased. Next, test drug (the compound (3)) and vehicle intraperitoneally injected into the rat and inhibitory activity on the increase action of blood pressure by S1P was observed. As a result, the compound (3) inhibited the increase of blood pressure by S1P.

BIOLOGICAL EXAMPLE 9

EDG-5 Antagonist Activity on the Blood Pressure of SHR Rat

Figure 10:
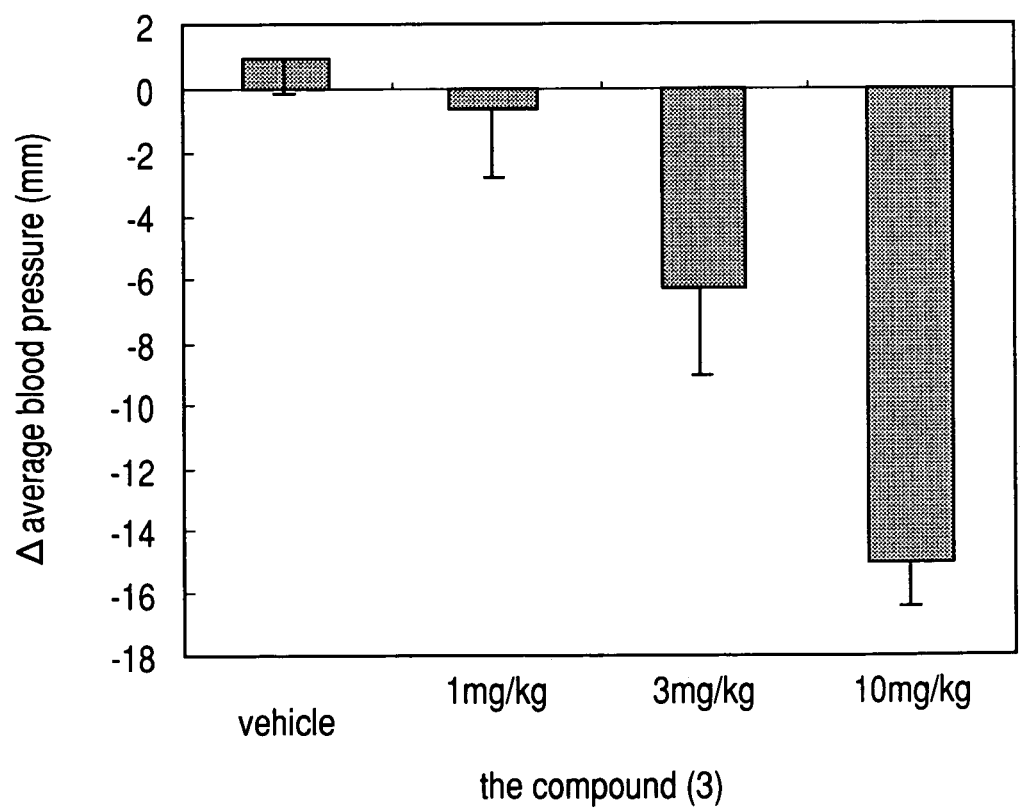
FIG. 10 is a graph showing the antihypertensive effect of elevation of blood pressure in SHR rat by the compound (3) of the present invention.

Rat (SHR/Crj, male, Charles River Japan Inc., 12 weeks old-13 weeks old) was anesthetized by ether, and then rat was fixed in the dorsal position on the laboratory table. Cannula filled with physiologic saline containing heparin was inserted into the femoral artery and cannula filled with physiologic saline was inserted into the femoral vein, respectively. After finish of the operation, rat was fixed in the ballmancage and left at rest until the awakening. The artery cannula was connected to the piezotransducer (DX-100, Nihon Kohden) and the blood pressure was measured through strain compression amplifier(AP-601G, Nihon Kohden). After about 30 minutes from confirming awakening of rat, the blood pressure was measured for additional 30 minutes and then, the compound (3) (1 mg/kg, 3 mg/kg, and 10 mg/kg, i.v.) or vehicle (10% DMSO/plasma) was administered intravenously. After administration, blood pressure was measured for more than 30 minutes. The results show FIG. 10. The compound (3) showed antihypertensive effects dose-independently on SHR rat under the awakening. In contrast, the compound (3) had little effect on the heart rate.

BIOLOGICAL EXAMPLE 10

Effect of EDG-5 Antagonist on Vasoconstrictor Action of Removed Rabbit Coronary Artery The heart was removed from Male rabbit (NZ White, a bout 2 kg) under anesthesia and immersed into cooled Krebs-Henseleit solution. After that, coronary artery was cut out, heart muscle and fat tissue connected around the heart were removed and ringed samples were made. Samples hung in micro tissue organ bath (MTOB-1: Preimetech Corp.) filled with Krebs-Henseleit solution (37° C.) or magnus tube, they were loaded with about 0.2 g-0.5 g resting tension stabilized for about 60 minutes, and then constrictive movement was recorded on a recorder (linearcoda WR3320: Graphtec Corp.) through strain compression amplifier (AP-601G, Nihon Kohden). As a result of activity of the compound (3) on constriction by S1P, inhibitory activity of the same compound was confirmed.

BIOLOGICAL EXAMPLE 11

Effect on the Removed Rat Heart (Langendorff Heart) by S1P

Figure 11:
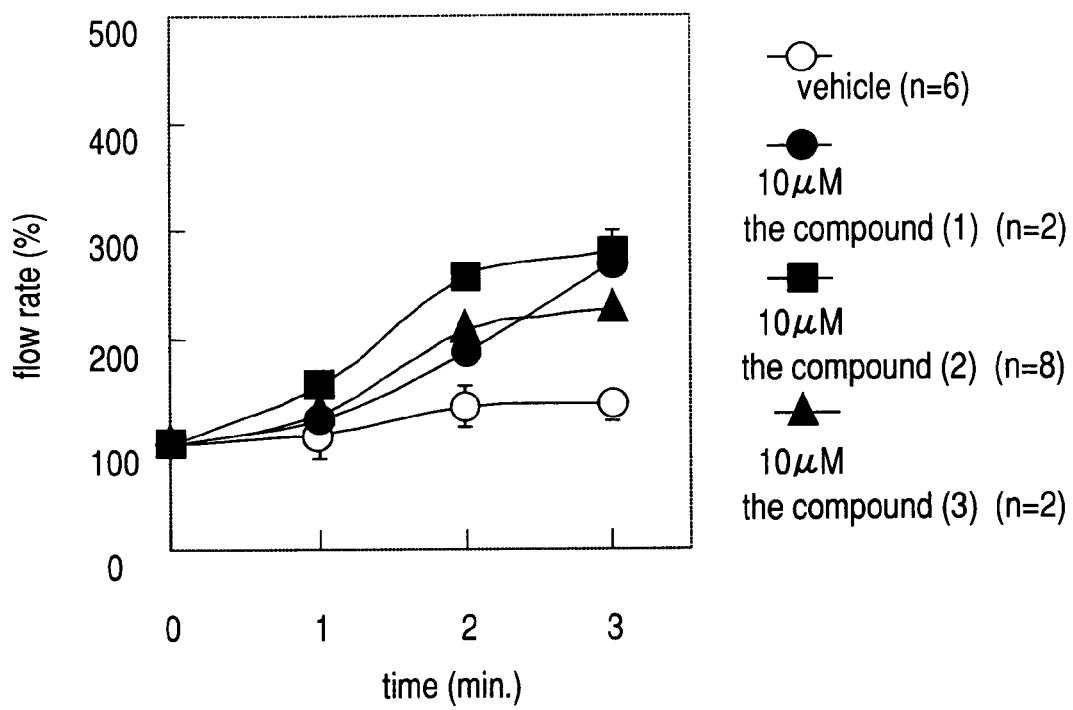
FIG. 11 is a graph showing the flow rate increased effect of rat removed heart by the compound (1), (2) or (3) of the present invention.

Rat (CD(SD)IGS, male, Charles River Japan Inc., 8 weeks old-10 weeks old, 300-450 g) was anesthetized by diethylether, opened the abdominal cavity, injected intravenously with heparin and then, exsanguinated to death. The heart was quickly removed by opening the chest cavity and the removed heart was immersed into cooled Krebs-Henseleit solution. The tissues were trimmed away under the cooling, aortic arches were inserted into the heart functional measuring equipment and fixed with sutures without leaking out. The rat heart function was measured using the heart functional measuring equipment (model IPH-W2, Labo-support). The equipment was used in the Langendorff Heart mode (non-working heart mode) and load was 68-70 mmHg. Pacing did not perform and Krebs-Henseleit solution (37° C.) was used as nutrient solution. Catheter filled with physiological saline was inserted into the left ventricle, the catheter was connected to the piezotransducer (DX-100, Nihon Kohden) and the left ventricle pressure (LVP) was measured through strain compression amplifier (AP-601G, Nihon Kohden). Heart rate was calculated using LVP data with the heart rate measuring equipment (AT-601G, Nihon Kohden) and dLVP/dt was calculated with differential processor (EQ-641G, Nihon Kohden). Probes of electromagnetic flowmeter (model FF-020T, inside diameter 2 mm, Nihon Kohden) were set on the way to the passage of nutrient solution and the flow rate of nutrient solution (corresponding the blood flow rate of coronary artery) was measured using electromagnetic flowmeter (MFV-3100, Nihon Kohden). Administration of S1P and the compounds was performed by injection of dilution with nutrient solution into the passage of nutrient solution using infusion pump. The injection rate of drug solution was set as the flow rate of nutrient solution before starting of administration. S1P dose-dependently decreased the contractive force of heart muscle. Using the above mentioned model, effect of EDG-5 antagonist on heart function was examined. The results show FIG. 11. EDG-5 antagonist, the compound (1), the compound (2) and the compound (3) increased the flow rate of nutrient solution. In addition, they increased contractive force of heart muscle at the same time. They showed little effect on heart rate. The results suggested that EDG-5 antagonist independently had effects of relaxing the coronary blood vessels and improving the cardiac ischemia condition. The data was not shown and the experiment using removed right artrium (with pacemaker) did not suggest that S1P had little effect on contractive force of heart muscle and heart rate. It was considered that S1P had no direct chronotropic action and inotropic action on pacemaker and heart muscle and S1P had lowering effect on heart function by contracting the coronary blood vessels and ischemia.

BIOLOGICAL EXAMPLE 12

Effect of EDG-5 Antagonist on Constriction of the Removed Rabbit Vein

Figure 12:
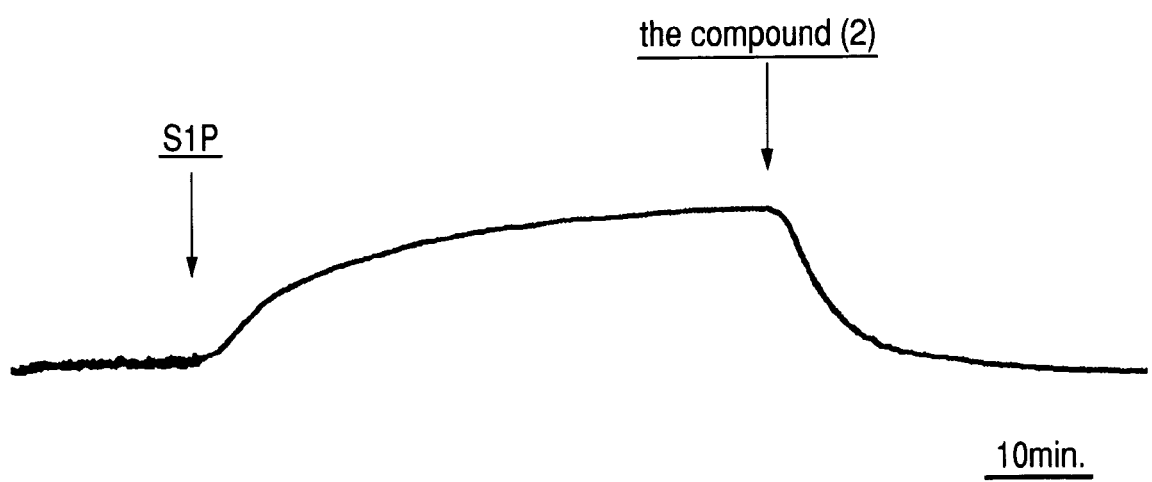
FIG. 12 is a graph showing the suppression of vasoconstrictor action of rat removed vein by the compound (2) of the present invention.

The portal vein/mesenteric vein was removed form male rabbit (NZ White, about 2 kg) under anesthesia and vertical sample of width 2-3 mm and length 3-4 mm was made. Made samples were hung in magnus tube (volume: 5 mL) filled with Krebs-Henseleit solution (37° C.) using a hook. They were loaded with 0.5 g resting tension stabilized for about 60 minutes, then constrictive movement was recorded on a recorder (linear recorder WR3320: Graphtec Corp.) through strain compression amplifier (AP-601G, Nihon Kohden) from Force displacement transducer (FD pickup TB-611T). The results show FIG. 12. As a result of the examination of effect of the compound (2) on contraction of vein by S1P, inhibitory effect of the same compound was confirmed.

FORMULATION EXAMPLE 1

The following components were admixed in a conventional method, punched out to give 100 tablets each containing 50 mg or active ingredient.
N-(1H-1,3,4-trimethylpyrazolo[3,4-b]pyridin-6-yl)amino-N'-(3-chlorophenyl)urea (5.0 g)
carboxy methyl cellulose calcium (disintegrator) (0.2 g)
magnesium stearate (lubricant) (1.0 g)
microcrystalline cellulose (4.7 g)

FORMULATION EXAMPLE 2

The following components were admixed in a conventional method. The solution was sterilized in a conventional method, filled in ampoules 5 mL each and freeze-dried in a conventional method to give 100 ampoules each containing 20 mg of active ingredient.
N-(1H-1,3,4-trimethylpyrazolo[3,4-b]pyridin-6-yl)amino-N'-(3-chlorophenyl)urea (2.0 g)
mannitol (20 g)
distilled water (1000 mL)

FORMULATION EXAMPLE 3

The following components were admixed in a conventional method, punched out to give 100 tablets each containing 50 mg of active ingredient.
4-(4-bromophenyl)-4-hydroxy-N-(3-(trifuloromethyl)phenyl)-1-piperidinecarboxamide (5.0 g)
carboxymethyl cellulose calcium (disintegrator) (0.2 g)
magnesium stearate (lubricant) (1.0 g)
microcrystalline cellulose (4.7 g)

FORMULATION EXAMPLE 4

The following components were admixed in a conventional method. The solution was sterilized in a conventional method, filled in ampoules 5 mL each and freeze-dried in a conventional method to give 100 ampoules each containing 20 mg of active ingredient.
4-(4-bromophenyl)-4-hydroxy-N-(3-(trifuloromethyl)phenyl)-1-piperidinecarboxamide (2.0 g)
mannitol (20 g)
distilled water (1000 mL)

The invention claimed is:
1. A compound represented by formula (I):

wherein:
A represents

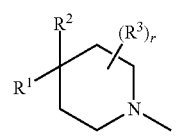

wherein $R^1$ represents
(1) benzene or pyridine optionally substituted with (1) halogen, (2) alkyl, (3) halo alkyl, or (4) alkoxy;
(2) C1-6 alkyl optionally substituted with (1) C1-4 alkylthio, (2) C3-7 cycloalkyl, or (3) heterocycl;
(3) C3-7 cycloalkyl; and
(4) naphthyl,
$R^2$ represents hydroxy or C1-6 alkoxy,
$R^3$ is absent, and
r represents 0,
X represents a single bond,
Y represents —CO—,
Z represents a nitrogen atom optionally substituted with C1-6 alkyl,
B represents benzene, or pyridine, optionally with 1-5 substituent(s) selected from (1) alkyl optionally substituted with halogen atom, (2) alkenyl optionally with a substituent(s), (3) alkynyl optionally with a substituent(s), (4) carbocyclic ring optionally with a substituent(s), (5) heterocyclic ring optionally with a substituent(s), (6) hydroxyl optionally with a substituent(s), (7) thiol optionally with a substituent(s), (8) amino optionally with a substituent(s), (9) carbamoyl optionally with a substituent(s), (10) sulfamoyl optionally with a substituent(s), (11) carboxyl, (12) alkoxycarbonyl, (13) sulfo, (14) sulfino, (15) phosphono, (16) nitro, (17) cyano, (18) amidino, (19) imino, (20) —B(OH)$_2$, (21) halogen atom, (22) alkysulfinyl, (23) aromatic ring sulfinyl, (24) alkylsulfonyl, (25) aromatic ring sulfonyl, (26) acyl, (27) oxo, (28) thioxo, and (29) (C1-6 alkoxyimino) methyl,
with proviso that B represents neither 3-(2-diisopropylamino)ethoxy-4-methoxyphenyl group, 1-isopropyl-4-(2-methoxyphenyl)piperidine group, an unsubstituted benzene group, nor a benzene substituted with a halogen atom when $R^1$ is a benzene,
or a pharmaceutically acceptable salt thereof.
2. The compound according to claim 1, wherein $R^2$ is hydroxy.
3. The compound according to claim 1, wherein $R^1$ is alkyl optionally substituted with (1) C1-4 alkylthio, (2) C3-7 cycloalkyl, or (3) heterocyclyl.
4. The compound according to claim 3, wherein B represents benzene, or pyridine, substituted with 1 or more substituent(s) selected from (1) alkyl optionally substituted with halogen atom, (2) alkenyl potionally with a substituent(s), (3) alknyl optionally with a substituent(s), (4) carbocyclic ring optionally with a substituent(s), (5) heterocyclic ring optionally with a substituent(s), (6) hydroxyl optionally with a substituent(s), (7) thiol optionally with a substituent(s), (8) amino optionally with a substituent(s), (9) carbamoyl optionally with a substituent(s), (10) sulfamoyl optionally with a substituent(s), (11) carboxyl, (12) alkoxycarbonyl, (13) sulfo, (14) sulfino, (15) phosphono, (16) nitro, (17) cyano, (18) amidino, (19) imino, (20) —B(OH)$_2$, (21) halogen atom, (22) alkysulfinyl, (23) aromatic ring sulfinyl, (24) alkylsulfonyl, (25) aromatic ring sulfonyl, (26) acyl, (27) oxo, (28) thioxo, and (29) (C1-6 alkoxyimino) methyl.

5. The compound according to claim 4, wherein B has at least 2 substituents with the following structure

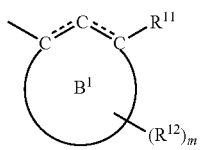

wherein $B^1$ represents benzene,
$R^{11}$ and $R^{12}$ each represents a substituent selected from (1) alkyl optionally substituted with halogen atom, (2) alkenyl optionally with a substituent(s), (3) alkynyl optionally with a substituent(s), (4) carbocyclic ring optionally with a substituent(s), (5) heterocyclic ring optionally with a substituent(s), (6) hydroxyl optionally with a substituent(s), (7) thiol optionally with a substituent(s), (8) amino optionally with a substituent(s), (9) carbamoyl optionally with a substituent(s), (10) sulfamoyl optionally with a substituent(s), (11) carboxyl, (12) alkoxycarbonyl, (13) sulfo, (14) sulfino, (15) phosphono, (16) nitro, (17) cyano, (18) amidino, (19) imino, (20) —B(OH)$_2$, (21) halogen atom, (22) alkysulfinyl, (23) aromatic ring sulfinyl, (24) alkylsulfonyl, (25) aromatic ring sulfonyl, (26) acyl, (27) oxo, (28) thioxo, and (29) (C1-6alkoxyimino) methyl, and
m represents an integer of 1-4.

6. The compound according to claim 1, wherein B represents benzene, or pyridine, substituted with 1 or more substituent(s) selected from (1) alkyl optionally substituted with halogen atom, (2) alkenyl optionally with a substituent(s), (3) alkynyl optionally with a substituent(s), (4) carbocyclic ring optionally with a substituent(s), (5) heterocyclic ring optionally with a substituent(s), (6) hydroxyl optionally with a substituent(s), (7) thiol optionally with a substituent(s), (8) amino optionally with a substituent(s), (9) carbamoyl optionally with a substituent(s), (10) sulfamoyl optionally with a substituent(s), (11) carboxyl, (12) alkoxycarbonyl, (13) sulfo, (14) sulfino, (15) phosphono, (16) nitro, (17) cyano, (18) amidino, (19) imino, (20) —B(OH)$_2$, (21) halogen atom, (22) alkysulfinyl, (23) aromatic ring sulfinyl, (24) alkylsulfonyl, (25) aromatic ring sulfonyl, (26) acyl, (27) oxo, (28) thioxo, and (29) (C1-6 alkoxyimino) methyl.

7. The compound according to claim 6, wherein B has at least 2 substituents with the following structure

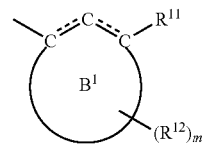

wherein $B^1$ represents benzene,
$R^{11}$ and $R^{12}$ each represents a substituent selected from (1) alkyl optionally substituted with halogen atom, (2) alkenyl optionally with a substituent(s), (3) alkynyl optionally with a substituent(s), (4) carbocyclic ring optionally with a substituent(s), (5) heterocyclic ring optionally with a substituent(s), (6) hydroxyl optionally with a substituent(s), (7) thiol optionally with a substituent(s), (8) amino optionally with a substituent(s), (9) carbamoyl optionally with a substituent(s), (10) sulfamoyl optionally with a substituent(s), (11) carboxyl, (12) alkoxycarbonyl, (13) sulfo, (14) sulfino, (15) phosphono, (16) nitro, (17) cyano, (18) amidino, (19) imino, (20) —B(OH)$_2$, (21) halogen atom, (22) alkysulfinyl, (23) aromatic ring sulfinyl, (24) alkylsulfonyl, (25) aromatic ring sulfonyl, (26) acyl, (27) oxo, (28) thioxo, and (29) (C1-6alkoxyimino) methyl, and
m represents an integer of 1-4.

* * * * *